(12) United States Patent
Arigon et al.

(10) Patent No.: US 8,815,853 B2
(45) Date of Patent: Aug. 26, 2014

(54) PYRIMIDINONE DERIVATIVES, PREPARATION THEREOF AND PHARMACEUTICAL USE THEREOF

(75) Inventors: Jerome Arigon, Paris (FR); Maurice Brollo, Paris (FR); Jacques Clement, Paris (FR); Romain Combet, Paris (FR); Florence Durand, Paris (FR); Youssef El Ahmad, Paris (FR); Jean-Robert Labrosse, Paris (FR); Jean-Philippe Letallec, Paris (FR); Baptiste Ronan, Paris (FR)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 13/996,866

(22) PCT Filed: Dec. 22, 2011

(86) PCT No.: PCT/EP2011/073874
§ 371 (c)(1),
(2), (4) Date: Jun. 21, 2013

(87) PCT Pub. No.: WO2012/085244
PCT Pub. Date: Jun. 28, 2012

(65) Prior Publication Data
US 2013/0289031 A1    Oct. 31, 2013

(30) Foreign Application Priority Data

Dec. 23, 2010  (FR) ...................... 10 61194
Dec. 23, 2010  (FR) ...................... 10 61197

(51) Int. Cl.
| | | |
|---|---|---|
| C07D 413/14 | (2006.01) |
| C07D 487/04 | (2006.01) |
| A61K 31/5377 | (2006.01) |
| A61K 31/519 | (2006.01) |
| C07D 487/10 | (2006.01) |
| C07D 233/44 | (2006.01) |
| C07D 239/12 | (2006.01) |
| C07D 239/34 | (2006.01) |

(52) U.S. Cl.
CPC ............ C07D 487/10 (2013.01); C07D 413/14 (2013.01); A61K 31/5377 (2013.01); A61K 31/519 (2013.01); C07D 233/44 (2013.01); C07D 239/12 (2013.01); C07D 239/34 (2013.01); C07D 487/04 (2013.01)
USPC ...................... 514/233.2; 544/117

(58) Field of Classification Search
CPC .............. C07D 487/04; C07D 413/14; A61K 31/5377; A61K 31/519
USPC ...................... 514/233.2; 544/117
See application file for complete search history.

(56) References Cited

U.S. PATENT DOCUMENTS

| 2012/0142679 A1 | 6/2012 | Brolio et al. |
| 2012/0208810 A1 | 8/2012 | Bacque et al. |

FOREIGN PATENT DOCUMENTS

| WO | WO 01/53266 A1 | 7/2001 |
| WO | WO 02/18386 A1 | 3/2002 |
| WO | WO 03/027116 A2 | 4/2003 |
| WO | WO 2004/016607 A1 | 2/2004 |
| WO | WO 2008/148074 A2 | 12/2008 |
| WO | WO 2009/093972 A1 | 7/2009 |
| WO | WO 2011/001112 A1 | 1/2011 |
| WO | WO 2011/001113 A2 | 1/2011 |

OTHER PUBLICATIONS

Cancer and Metastasis Reviews (1998), 17(1), 91-106.*
Science (1999), vol. 286, 531-537.*
Anja Apel, et al., Blocked Autophagy Sensitizes Resistant Carcinoma Cells to Radiation Therapy, Cancer Res, (Mar. 1, 2008), vol. 68, No. 5, pp. 1485-1494.
Anu Gupta, et al., Autophagy inhibition an antimalarials promote cell death in gastrointestinal stromal tumor (GIST), PNAS, (Aug. 10, 2010), vol. 107, No. 32, pp. 14333-14338.
Sergey B. Aliabiev, et al., A Convenient Synthesis of Novel Substituted Isoxazolo (5,4-d) Pyrimidines, Letters in Organic Chemistry, (2007), vol. 4, pp. 273-280.
Alejandro Vazquez-Martin, et al., Autophagy Facilitates the Development of Breast Cancer Resistance to the Anti-HER2 Monoclonal Antibody Trastuzumab, PLoS One, (Jul. 16, 2009), vol. 4, Issue 7, pp. 1-13.
Beth Levine, et al., Autophagy in the Pathogenesis of Disease, Cell, (Jan. 11, 2008), vol. 132, pp. 27-42.

(Continued)

*Primary Examiner* — Rebecca Anderson
(74) *Attorney, Agent, or Firm* — Scully, Scott, Murphy & Presser, P.C.

(57) ABSTRACT

The invention relates to novel products of formula (Ia) or (Ib):

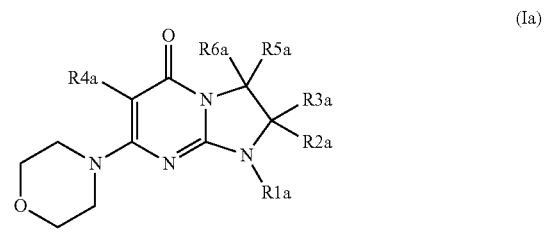

(Ia)

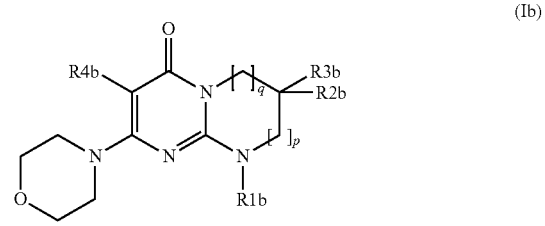

(Ib)

these products being in all the isomeric forms and salts as drugs, notably as anticancer drugs.

14 Claims, No Drawings

(56) References Cited

OTHER PUBLICATIONS

Bart Vanhaesebroeck, et al., The emerging mechanisms of isoform-specific PI35 signalling, Molecular Cell Biology, (May 2010), vol. 11, pp. 329-341.

El-Sayed A.M. Badawey, et al., Nonsteroidal antiinflammatory agents—Part 1: Antiinflammatory, analgesic and antipyretic activity of some new 1-(pyrimidin-2-yl)-3-pyrazolin-5-ones and 2-(pyrimidin-2-yl)-1,2,4,5,6,7-hexahydro-3H-indazol-3-ones, Eur. J. Med. Chem., (1998), vol. 33, pp. 349-661.

Florent Huguenot, et al., Concise Synthesis of Enantiopure a-Trifluoromethyl Alaninse, Diamines, and Amino Alcohols via the Strecker-type Reaction, J. Org. Chem., (Sep. 1, 2006), vol. 71, pp. 7075-7078.

Johannes A. Burkhard, et al., Oxetanes as Versatile Elements in Drug Discovery and Synthesis, Angew. Chem. Int. Ed., (Nov. 22, 2010), vol. 49, pp. 9052-9067.

Bao Hoang, et al., Effect of autophagy on multiple myeloma cell viability, Mol Cancer Ther, (Jul. 2009), vol. 8, No. 7, pp. 1974-1984.

Isabelle Vergne, et al., The role of PI3P phosphatases in the regulation of autophagy, FEBS Letters, (Apr. 2, 2010), vol. 584, pp. 1313-1328.

Jie Li, et al., Inhibition of autophagy augments 5-fluorouracil chemotherapy in human colon cancer in vitro and in vivo model, European Journal of Cancer, (Jul. 2010), vol. 46, pp. 1900-1909.

Jennifer S. Carew, et al., Targeting autophagy augments the anticancer activity of the histone deacetylase inhibitor SAHA to overcome Bcr-Abl-mediated drug resistance, Blood, (Jul. 1, 2007), vol. 110, No. 1, pp. 313-322.

Julia S. Samaddar, et al., A role for macroautophagy in protection against 4-hydroxytamoxifen-induced cell death and the development of antiestrogen resistance, Mol Cancer Ther, (Sep. 2008), vol. 7, No. 9, pp. 2977-2987.

Noboru Mizushima, et al., Autophagy fights disease through cellular self-digestion, Nature, (Feb. 28, 2008), vol. 451, No. 28, pp. 1069-1075.

Nina Raben, et al., Suppression of autophagy permits successful enzyme replacement therapy in a lysosomal storage disorder-murine Pompe disease, Autophagy, (Nov. 16, 2010), vol. 6, No. 8, pp. 1078-1089.

Johannes A. Burkhard, et al., Synthesis and Structural Analysis of a New Class of Azaspiro[3.3]heptanes as Building Blocks for Medicinal Chemistry, Organic Letters, (May 7, 2010), vol. 12, No. 9, pp. 1944-1947.

Qi-Wen Fan, et al., Akt and Autophagy Cooperate to Promote Survival of Drug-Resistant Glioma, Sci Signal., (Nov. 9, 2010), vol. 3, Issue 147, pp. 1-11.

Sharon A. Tooze, et al., The origin of the autophagosomal membrane, Nature Cell Biology, (Sep. 2010), vol. 12, No. 9, pp. 831-835.

Pauline C. Ting, et al., Substituted 1,3-Dihydro-2H-pyrrolo[2-3-b]pyridin-2-ones as Potential Antiinflammatory Agents, J. Med. Chem., (Oct. 1990), vol. 33, No. 10, pp. 2697-2706.

Xinquen Li, et al., The Epidermal Growth Factor Receptor Antibody Cetuximab Induces Autophagy in Cancer Cells by Downregulating HIF-1a and Bcl-2 and Activating the Beclin 1/hVps34 Complex, Cancer Res, (Jul. 15, 2010), vol. 70, No. 14, pp. 5942-5952.

Ayako Yamashita, et al., Improved Procedures for Preparation of Racemic Capreomycidine, Synthetic Communications, (2004), vol. 34, No. 5, pp. 795-803.

Zhaoju Wu, et al., Autophagy Blockade Sensitizes Prostate Cancer Cells towards Src Family Kinase Inhibitors, Genes & Cancer, (Jan. 2010), vol. 1, No. 1, pp. 40-49.

Zhifen Yang, et al., Eaten alive: a history of macroautophagy, Nature Cell Biology, (Sep. 2010), vol. 12, No. 9, pp. 814-822.

Verheijen, Jeroen C., et al., "Phosphatidylinositol 3-kinase (PI3K) inhibitors as anticancer drugs," Drugs of the Future, Prous Sceience, Es, Jun. 1, 2007, vol. 32, No. 6, pp. 537-547.

International Search Report dated Jan. 27, 2012 issued in PCT/EP2011/073874.

\* cited by examiner

PYRIMIDINONE DERIVATIVES, PREPARATION THEREOF AND PHARMACEUTICAL USE THEREOF

The present invention relates to novel chemical compounds (2,3-dihydro-1H-imidazo{1,2-a}pyrimidin-5-one and 1,2,3,4-tetrahydro-pyrimido{1,2-a}pyrimidin-6-one), derived from pyrimidinones, to their preparation method, to the novel intermediates obtained, to their application as drugs, to pharmaceutical compositions containing them and to a novel use of such derivatives.

The present invention thus also relates to the use of said derivatives for preparing a drug intended for treating humans.

More particularly, the invention relates to novel derivatives of pyrimidinones and to their pharmaceutical use for preventing and treating diseases which may be modulated by the inhibition of the Vps34/PIK3C3 route. Vps34/PIK3C3 is a key actor of autophagy. Vps34/PIK3C3 is also involved in the phenomena of endocytosis and phagocytosis (B. Vanhaesebroeck et al. Nat Rev Mol Cell Biol 2010).

The inhibition and the regulation of the Vps34/PIK3C3 route are notably a new action mechanism for treating a large number of cancer diseases including solid and liquid tumors.

Role of the Vps34/PIK3C3 Route

The signaling route Vps34/PIK3C3 is a complex network which regulates multiple cell functions, such as autophagy, endocytoses and phagocytoses (B. Vanhaesebroeck et al. Nat Rev Mol Cell Biol 2010). This signaling route is a significant target in the treatment of cancer since the autophagy, endocytosis and phagocytosis phenomena are altered in human tumors.

The lipid kinase PI3K of class III (Vps34/PIK3C3) forms a heterodimer with the protein Vps15. Vps15 is myristoylated, thus allowing the complex Vps34/Vps15 to be anchored in the membranes. This heterodimer is again found in various multiprotein complexes, thereby highlighting its various biological functions (B. Vanhaesebroeck et al. Nat Rev Mol Cell Biol 2010). Vps34/PIK3C3 phosphorylates phosphatidylinositol (PI) in position 3 of the inositol in order to obtain phosphatidylinositol 3-phosphate (PI3P). PI3P is a secondary messenger. Myotubularin phosphatase lipids (MTM) dephosphorylate the PI3P on position 3. Among the 16 MTMs described, the proteins MTMR3, 6, 7, 14 (JUMPY) would be involved in the inhibition of the formation of autophagosomes and therefore of autophagy (I. Vergne FEBS Lett 2010).

Role of Vps34/PIK3C3 in Autophagy

The PI3P formed by Vps34/PIK3C3 is a key secondary messenger in the formation of autophagosomes via the recruitment of proteins such as WIPI, DFCP1 and Alfy (S. Tooze et al., Nat Cell Biol 2010). The autophagosomes formed will then merge with lysosomes allowing degradation of the constituents of the cytoplasm (organelles, proteins with long lifetimes . . . ) (Z. Yang et al. Nat Cell Biol 2010).

Autophagy is a cell survival mechanism allowing the cell to survive in a stress situation, such as for example facing a metabolic stress. In the case of cancer, autophagy is involved in the resistance of the tumoral cells facing environmental stresses such as: hypoxia, oxidative stresses, deficiency of nutrients, but also facing therapeutic stresses: treatments with anti-cancer agents, ionizing radiations. Further, this signaling route is a major factor for resistance to chemotherapy, radiotherapy and target therapies such as the inhibitors of EGFR, HER2 or Bcr-Abl of example (Q W. Fan et al., Since signaling 2010, A. Gupta et al. PNAS 2010, X Li et al. Cancer Res 2010, A Vazquez-Martin et al. PLos One 2009, Z. Wu et al. Genes Cancer 2010).

Role of Vps34/PIK3C3 in Endocytosis

At the level of the endosomes, PI3P allows recruitment of molecules such as EEA1, HRS and ESCRT, thus leading to the merging of endocytic vesicles. The protein Vps34/PIK3C3 was described as being involved in endosomal traffic of certain transmembrane receptors such as the tyrosine kinase receptors (receptor to EGF, to PDGF), the receptor to transferrin for example (B. Vanhaesebroeck et al. Nat Rev Mol Cell Biol 2010).

Role of Vps34/PIKC3 in Phagocytosis

The PI3P is also generated at the membranes of the phagosomes. The role of the Vps34/PIKC3 protein does not seem to be involved in the initiation of the membranes of the phagosomes, but in the maturation of the phagosomes. Finally, the PI3P formed by the Vps34/PI3KC3 protein would be involved in the activation of NADPH oxidase at the phagosome (B. Vanhaesebroeck et al. Nat Rev Mol Cell Biol 2010).

Morpholino-pyrimidinone derivatives, inhibitors of kinases are known to one skilled in the art.

The application WO2008/148074 describes products which have an mTOR inhibitory activity. These products are pyrido[1,2-a]pyrimidin-4-ones which differ from the products of the present invention because of their entirely aromatic nature and of their substitutions.

Application WO2008/064244 describes the application of the products TGX-221 and TGX-155, inhibitors of PI3Kβ, useful for treating cancer and notably breast cancer. These products are pyrido[1,2-a]pyrimidin-4-ones described earlier in applications WO2004/016607 and WO2001/053266 which differ from the products of the present invention because of their entirely aromatic nature and of their substitutions.

Applications WO2006/109081, WO2006/109084 and WO2006/126010 describe products, inhibitors of DNA-PK, useful for treating deficient ATM cancers. These products are pyrido[1,2-a]pyrimidin-4-ones which differ from the products of the present invention because of their entirely aromatic nature and of their substitutions.

Application WO2003/024949 describes products, inhibitors of DNA-PK, useful for treating deficient ATM cancers. These products are pyrido[1,2-a]pyrimidin-4-ones which differ from the products of the present invention because of their entirely aromatic nature and of their substitutions.

The object of the present invention is products of formula (Ia):

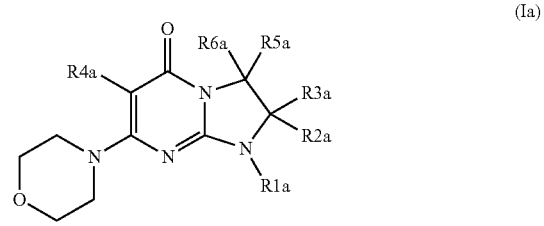

(Ia)

wherein:

R1a represents a linear or branched alkyl, alkenyl or alkynyl radical, a cycloalkyl radical or a heterocycloalkyl radical, containing from 1 to 7 carbon atoms, all these radicals being optionally substituted with one or several radicals either identical or different selected from halogen atoms and the radicals R7a, —S(O)xa-R7a with xa representing the integer 0, 1 or 2, —SO$_2$NR5aR7a, —CN, —OR5a, —NR5aR6a, —NR5a-

COR7a, —NR5a-CO₂—R7a, —NR5a-SO₂—R7a, —NHCONR5aR6a, —COR7a, —CO₂R5a and —CONR5aR6a;

R2a represents a hydrogen atom, an alkyl radical or a cycloalkyl;

R3a represents an alkyl radical, a cycloalkyl radical or a phenyl optionally substituted with one or several radicals either identical or different selected from halogen atoms and radicals —OR5a and —NR5aR6a;

R2a and R3a may optionally form with the carbon atom to which they are bound a cyclic radical containing 3 to 10 members and optionally one or several other heteroatoms selected from O, S and —NR5a, this cyclic radical being optionally substituted with one or several radicals either identical or different, selected from halogen atoms, oxo, R5a, —OR5a and —NR5aR6a radicals;

R4a represents a hydrogen atom, an alkyl radical, a halogen atom or a —CN radical;

with R5a and R6a either identical or different representing a hydrogen atoms or an alkyl, a cycloalkyl or heterocycloalkyl radical and R7a, either identical or different from R5a and R6a, represents and alkyl, cycloalkyl or heterocycloalkyl radical, the alkyl, cycloalkyl, heterocycloalkyl radicals above which R5a, R6a and R7a may represent, being themselves optionally substituted with one or several radicals, either identical or different, selected from halogen atoms, —OR8a and —NR8aR9a with R8a and R9a either identical or different representing a hydrogen atoms or an alkyl, cycloalkyl or heterocycloalkyl radical;

said products of formula (Ia) being in all the racemic, enantiomeric and diastereoisomeric possible is0meric forms, as well as addition salts with inorganic and organic acids or with inorganic and organic bases of said products of formula (Ia).

The cyclic radical which R2a and R3a may optionally form on the one hand, and which R5a and R6a may form on the other hand, with the carbon atom to which they are bound, as defined above, may thus represent a carbocyclic (spirocycloalkyl) radical such as the spirocyclopropyl, cyclobutyl, cyclopentyl or cyclohexyl radical or further represent a heterocyclic radical such as for example the oxetane radical, all these radicals being optionally substituted as defined above.

The object of the present invention is notably the products of formula (Ia) as defined above wherein:

R1a represents a linear or branched alkyl radical, a cycloalkyl radical or a heterocycloalkyl radical, containing from 1 to 6 carbon atoms, the alkyl radical being optionally substituted with one or several radicals, either identical or different, selected from halogen atoms and hydroxyl, alkoxy, O-cycloalkyl, cycloalkyl, heterocycloalkyl and —S(O)xa-alkyl radicals with xa representing the integer 0, 1 or 2;

the latter alkyl, alkoxy and —S(O)xa-alkyl radicals being themselves optionally substituted with one or several radicals, either identical or different, selected from halogen atoms;

R2a represents a hydrogen atom or an alkyl radical;

R3a represents a hydrogen atom or an alkyl radical optionally substituted with one or several halogen atoms;

R5a represents a hydrogen atom or an alkyl radical;

R6a represents a hydrogen atom or an alkyl radical optionally substituted with one or several halogen atoms;

R2a and R3a on the one hand and R5a and R6a on the other hand, may optionally form, respectively with the carbon atoms to which they are bound, a cyclic radical containing from 3 to 7 members and optionally an oxygen atom, this cyclic radical being optionally substituted with one or several radicals, either identical or different, selected from halogen atoms, alkyl, hydroxyl, oxo, alkoxy, NH₂; NHalk and N(alk)₂ radicals;

it being understood that R2a, R3a, R5a and R6a are such that R2a and R3a or else R5a and R6a represent two hydrogen atoms;

R4a represents a hydrogen atom, an alkyl radical or a halogen atom;

said products of formula (Ia) being in all the racemic, enantiomeric and diastereoisomeric possible isomeric forms, as well as addition salts with inorganic and organic acids or with inorganic and organic bases of said products of formula (Ia).

The object of the present invention is thus products of formula (Ia) as defined above wherein R5a and R6a represent two hydrogen atoms and R2a and R3a are selected from the values defined above or else form a cyclic radical with the carbon atom to which they are bound, as indicated above.

The object of the present invention is thus the products of formula (Ia) as defined above wherein R2a and R3a represent two hydrogen atoms and R5a and R6a are selected from the values defined above or else from a cyclic radical with the carbon atoms to which they are bound, as indicated above.

The object of the present invention is notably the products of formula (Ia) as defined above wherein:

R1a represents a linear or branched alkyl radical, or a cycloalkyl radical, the alkyl radical being optionally substituted with one or several radicals, either identical or different, selected from halogen atoms and hydroxyl, alkoxy, cycloalkyl and —S(O)₂-alkyl radicals;

the latter alkyl, alkoxy and —S(O)₂-alkyl radicals, being themselves optionally substituted with one or several radicals, either identical or different, selected from halogen atoms;

R2a represents a hydrogen atom or an alkyl radical;

R3a represents an alkyl radical optionally substituted with one or several radicals, identical or different, selected from halogen atoms;

R2a and R3a may optionally form with the carbon atom to which they are bound, a cyclic radical containing from 3 to 5 members;

R4a represents a hydrogen atom, an alkyl radical or a halogen atom;

R5a and R6a represent two hydrogen atoms, said products or formula (Ia) being in all the racemic, enantiomeric and diastereoisomeric possible isomeric forms, as well as addition salts with inorganic and organic acids or with inorganic and organic bases of said products of said formula (Ia).

Most particularly, the object of the present invention is the products of formula (Ia) as defined above, having the following formulae:

(2S)-1-(2-Ethylbutyl)-2-methyl-7-(morpholin-4-yl)-2-(trifluoromethyl)-2,3-dihydroimidazo[1,2-a]pyrimidin-5(1H)-one (2S)-1-Cyclopropyl-2-methyl-7-(morpholin-4-yl)-2-(trifluoromethyl)-2,3-dihydroimidazo[1,2-a]pyrimidin-5(1H)-one (2S)-1-Cyclopentyl-2-methyl-7-(morpholin-4-yl)-2-(trifluoromethyl)-2,3-dihydroimidazo[1,2-a]pyrimidin-5(1H)-one (S)-1-(2-Isopropoxy-ethyl)-2-methyl-7-(morpholin-4-yl)-2-(trifluoromethyl)-2,3-dihydroimidazo[1,2-a]pyrimidin-5(1H)-one (S)-1-(2-Hydroxy-2-methyl-propyl)-2-methyl-7-(morpholin-4-yl)-2-(trifluoromethyl)-2,3-dihydroimidazo[1,2-a]pyrimidin-5(1H)-one (S)-1-(2-Methoxy-2-methyl-propyl)-2-methyl-7-(morpholin-4-yl)-2-(trifluoromethyl)-2,3-dihydroimidazo[1,2-a]pyrimidin-5(1H)-one 1-(2-Isopropoxyethyl)-2,2-dimethyl-7-(morpholin-4-yl)-2,3-dihydroimidazo[1,2-a]pyrimidin-5(1H)-one 1'-(2-Methoxyethyl)-7'-morpholin-4-ylspiro[cyclopentane-1,2'-imidazo[1,2-a]pyrimidin]-5'-one 1-(2-Isopropoxyethyl)-7'-morpholin-4-ylspiro[cyclopentane-1,2'-imidazo[1,2-a]pyrimidin]-5'-one as well as addition salts with inorganic and organic acids or with inorganic and organic bases of said products of formula (Ia).

The object of the present invention is also products of formula (Ib):

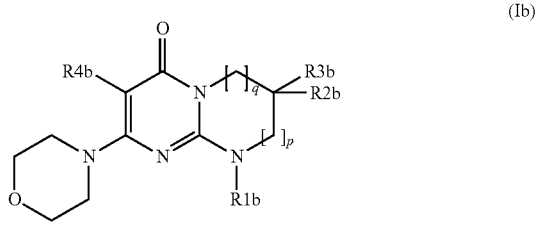

wherein:
p=0 or 1 and q=1 or 2 such that:
if p=0 then q=2;
if p=1 then q=1
R1b represents linear or branched alkyl, alkenyl, or alkynyl radicals, a cycloalkyl radical or a heterocycloalkyl radical, containing from 1 to 7 carbon atoms, all these radicals being optionally substituted with one or several radicals, either identical or different, selected from halogen atoms and the radicals R7b, —S(O)xb-R7b with xb representing the integer 0, 1 or 2, —SO₂NR5bR7b, —CN, —OR5b, —NR5bR6b, —NR5b-COR7b, —NR5b-CO₂—R7b, —NR5b-SO₂—R7b, —NHCONR5bR6b, —COR7b, —CO₂R5b and —CONR5bR6b;
R2b represents a hydrogen atom, an alkyl radical or a cycloalkyl radical;
R3b represents and alkyl radical, a cycloalkyl or phenyl radical optionally substituted with one or several radicals, either identical or different, selected from halogen atoms and from —OR5b and —NR5bR6b radicals;
R2b and R3b may optionally form with the carbon atom to which they are bound, a cyclic radical containing from 3 to 20 members and optionally one or several other heteroatoms selected from O, S and —NR5b, this cyclic radical being optionally substituted with one or several radicals, either identical or different, selected from halogen atoms, oxo, R5b, —OR5b and —NR5bR6b radicals;
R4b represents a hydrogen atom, an alkyl radical, a halogen atom or a —CN radical;
with R5b and R6b, either identical or different, representing a hydrogen atom or an alkyl, cycloalkyl or heterocycloalkyl radical
and R7b, either identical or different from R5b and R6b, representing an alkyl, cycloalkyl or heterocycloalkyl radical, the above alkyl, cycloalkyl, heterocycloalkyl radicals which are R5b and R6b and R7b may represent, being themselves optionally substituted with one or several radicals, either identical or different, selected from halogen atoms, —OR8b et —NR8bR9b with R8b and R9b, either identical or different, representing a hydrogen atom or an alkyl, cycloalkyl, or heterocycloalkyl radical;

said products of formula (Ib) being in all the racemic, enantiomeric and diastereoisomeric possible isomeric forms, as well as addition salts with inorganic and organic acids or with inorganic and organic bases of said products of formula (Ib).

The cyclic radicals which R2b and R3b may optionally form with the carbon atoms to which they are bound, as defined above, may thus represent a carbocyclic (spirocycloalkyl) radical such as the cyclopropyl, cyclobutyl, cyclopentyl or cyclohexyl radical, or further represent a heterocyclic radical such as for example the oxetane radical, all these radicals being optionally substituted as defined above.

The object of the present invention is notably the products of formula (Ib) as defined above, wherein:
p=1 and q=1
R1b represents a linear or branched alkyl radical, a cycloalkyl radical or a heterocycloalkyl radical, containing from 1 to 6 carbon atoms, the alky radical being optionally substituted with one or several radicals, either identical or different, selected from halogen atoms and hydroxyl, alkoxy, —O-cycloalkyl, cycloalkyl, heterocycloalkyl and —(O)xb-alkyl radicals with xb representing the integer 0, 1 or 2;
the latter alkyl, alkoxy and —S(O)xb-alkyl radicals being themselves optionally substituted with one or several radicals, either identical or different, selected from halogen atoms;
R2b represents a hydrogen atom or an alkyl radical;
R3b represents an alkyl radical optionally substituted with one or several halogen atoms;
R2b and R3b may optionally form with the carbon atom to which they are bound, a cyclic radical containing from 3 to 7 members and optionally an oxygen atom, this cyclic radical being optionally substituted with one or several radicals, either identical or different, selected from halogen atoms, alkyl, hydroxyl, oxo, alkoxy, —NH₂; —NHalk and —N(alk)₂ radicals;
R4b represents a hydrogen atom, an alkyl radical or a halogen atom;
said products or formula (Ib) being in all the racemic, enantiomeric and diastereoisomeric possible isomeric forms, as well as addition salts with inorganic and organic acids or with inorganic and organic bases of said products of formula (Ib).

The object of the present invention is notably products of formula (Ib) as defined above wherein:
p=1 and q=1
R1b represents a linear or branched alkyl radical, or a cycloalkyl radical, the alkyl radical being optionally substituted with one or several identical or different radicals, selected from halogen atoms and hydroxyl, alkoxy, cycloalkyl and —S(O)₂-alkyl radicals;
the latter alkyl, alkoxy and —S(O)xb-alkyl radicals, being themselves optionally substituted with one or several radicals, either identical or different, selected from halogen atoms;
R2b represents a hydrogen atom or an alkyl radical;
R3b represents an alkyl radical optionally substituted with one or several radicals, either identical or different, selected from halogen atoms;
R2b and R3b may optionally form with the carbon atom to which they are bound, a cyclic radical containing from 3 to 5 members;
R4b represents a hydrogen atom, an alkyl radical or a halogen atom;
said products of formula (IB) being in all the racemic, enantiomeric and diastereoisomeric possible isomeric forms, as well as addition salts with inorganic and organic acids or with inorganic and organic bases of said products of formula (Ib).

Most particularly, the object of the present invention is the products of formula (Ib) as defined above having the following formulae:

(8S)-9-(2-Ethylbutyl)-2-(morpholin-4-yl)-8-(trifluoromethyl)-6,7,8,9-tetrahydro-4H-pyrimido[1,2-a]pyrimidin-4-one (8S)-9-(Cyclopropylmethyl)-2-(morpholin-4-yl)-8-(trifluoromethyl)-6,7,8,9-tetrahydro-4H-pyrimido[1,2-a]pyrimidin-4-one (8S)-9-Cyclopentyl-2-(morpholin-4-yl)-8-(trifluoromethyl)-6,7,8,9-tetrahydro-4H-pyrimido[1,2-a]pyrimidin-4-one (8S)-9-(2-Hydroxyethyl)-2-(morpholin-4-yl)-8-(trifluoromethyl)-6,7,8,9-tetrahydro-4H-pyrimido[1,2-a]pyrimidin-4-one (S)-9-(2-Isopropoxy-ethyl)-2-(morpholin-4-yl)-8-trifluoromethyl-6,7,8,9-tetrahydro-4H-pyrimido[1,2-a]pyrimidin-4-one (S)-2-(Morpholin-4-yl)-9-[2-(2,2,2-trifluoro-ethoxy)-ethyl]-8-(trifluoromethyl)-6,7,8,9-tetrahydro-4H-pyrimido[1,2-a]pyrimidin-4-one (8S)-3-Fluoro-9-(2-isopropoxy-ethyl)-2-(morpholin-4-yl)-8-(trifluoromethyl)-6,7,8,9-tetrahydro-4H-pyrimido[1,2-a]pyrimidin-4-one (8S)-9-(2-Hydroxy-2-methylpropyl)-2-(morpholin-4-yl)-8-(trifluoromethyl)-6,7,8,9-tetrahydro-4H-pyrimido[1,2-a]pyrimidin-4-one (S)-9-(2-Hydroxy-2-methyl-propyl)-3-methyl-2-(morpholin-4-yl)-8-trifluoromethyl-6,7,8,9-tetrahydro-4H-pyrimido[1,2-a]pyrimidin-4-one (S)-9-(2-Methoxy-2-methyl-propyl)-2-(morpholin-4-yl)-8-trifluoromethyl-6,7,8,9-tetrahydro-4H-pyrimido[1,2-a]pyrimidin-4-one (8S)-8-Methyl-2-(morpholin-4-yl)-9-(2-(propan-2-yloxy)ethyl)-8-(trifluoromethyl)-6,7,8,9-tetrahydro-4H-pyrimido[1,2-a]pyrimidin-4-one (8R)-8-Methyl-2-(morpholin-4-yl)-9-(2-(propan-2-yloxy)ethyl)-8-(trifluoromethyl)-6,7,8,9-tetrahydro-4H-pyrimido[1,2-a]pyrimidin-4-one 9-(2-Methoxyethyl)-8,8-dimethyl-2-(morpholin-4-yl)-6,7,8,9-tetrahydro-4H-pyrimido[1,2-a]pyrimidin-4-one 9-(2-Isopropoxyethyl)-8,8-dimethyl-2-(morpholin-4-yl)-6,7,8,9-tetrahydro-4H-pyrimido[1,2-a]pyrimidin-4-one 9-(2-Methoxyethyl)-7,7-dimethyl-2-(morpholin-4-yl)-6,7,8,9-tetrahydro-4H-pyrimido[1,2-a]pyrimidin-4-one 9-(2-Isopropoxyethyl)-7,7-dimethyl-2-(morpholin-4-yl)-6,7,8,9-tetrahydro-4H-pyrimido[1,2-a]pyrimidin-4-one 1'-(2-Isopropoxyethyl)-8'-(morpholin-4-yl)-1',2'-dihydrospiro[cyclopropane-1,3'-pyrimido[1,2-a]pyrimidin]-6'-one (8S)-9-(2-Methanesulfonyl-ethyl)-2-morpholin-4-yl-8-trifluoromethyl-6,7,8,9-tetrahydro-pyrimido[1,2-a]pyrimidin-4-one as well as the addition salts with the inorganic and organic acid or with the inorganic and organic bases of said products of formula (Ib).

In the products of formula (Ia) or (Ib):

the term of alkyl radical (or alk) refers to linear and branched radicals containing from 1 to 10 carbon atoms such as, methyl, ethyl, propyl, isopropyl, butyl, isobutyl, sec-butyl, tert-butyl, pentyl, isopentyl, hexyl, isohexyl and also heptyl, octyl, nonyl and decyl linear or branched position isomers: alkyl radicals containing from 1 to 6 carbon atoms and more particularly alkyl radicals containing from 1 to 4 carbon atoms are preferred from the list above;

the term of alkenyl radical refers to linear and branched radicals containing from 2 to 10 carbon atoms, selected from the alkyl radicals defined above containing one or several double bonds such as allyl, but-3-enyl, pent-4-enyl, as well as their linear or branched position isomers: the allyl and but-3-enyl radicals are preferred;

the term of alkynyl radical refers to linear and branched radicals containing from 2 to 10 carbon atoms selected from the alkyl radicals defined above containing one or several triple bounds such as propargyl, but-3-ynyl, pent-4-ynyl as well as their linear or branched position isomers: the propargyl and but-3-ynyl radicals are preferred;

the term of alkoxy radical refers to linear and branched radicals, containing from 1 to 10 carbon atoms, methoxy, ethoxy, propoxy, isopropoxy, butoxy, either linear, secondary or tertiary, pentoxy or hexoxy as well as their linear or branched position isomers: alkoxy radicals containing from 1 to 4 carbon atoms are preferred from the list above;

the term of alkylthio or —S(O)x-alkyl radical refers to linear radicals and if necessary branched radicals, wherein the alkyl remainder has the definition indicated above for the alkyl radical; —S(O)x-alkyl thus notably represents —S(O)xmethyl, —S(O)xethyl, —S(O)xpropyl, —S(O)xisopropyl, —S(O)xbutyl, either linear, secondary or tertiary, —S(O)xpentyl or —S(O)xhexyl as well as their linear or branched position isomers, —S(O)x-alkyl radicals containing from 1 to 4 carbon atoms are preferred from the list above;

the term of halogen atom refers to chlorine, bromine, iodine or fluorine atoms and preferably chlorine, bromine or fluorine atoms.

the term of cycloalkyl radical refers to a saturated carbocyclic radical containing from 3 to 10 carbon atoms and thus notably refers to cyclopropyl, cyclobutyl, cyclopentyl and cyclohexyl radicals and most particularly the cyclopropyl, cyclopentyl and cyclohexyl radicals;

in the —O-cycloalkyl radical, wherein the cycloalkyl remainder is as defined above;

the term of heterocycloalkyl radical thus refers to a monocyclic or bicyclic carbocyclic radical, containing from 3 to 10 members interrupted by one or several heteroatoms, either identical or different, selected from oxygen, nitrogen or sulfur atoms: for example mention may be made of morpholinyl, thiomorpholinyl, homomorpholinyl, aziridyl, azetidyl, piperazinyl, piperidyl, homopiperazinyl, pyrrolidinyl, imidazolidinyl, pyrazolidinyl, tetrahydrofuryl, tetrahydrothienyl, tetrahydropyrane, oxodihydropyridazinyl, radicals or further oxetanyl radical, all these radicals being optionally substituted; mention may notably be made of morpholinyl, thiomorpholinyl, homomorpholinyl, piperazinyl, piperidyl, homopiperazinyl or further pyrrolidinyl radicals.

The compounds of formula (Ia) or (Ib) may include one or several asymmetrical centers. They may therefore exist as enantiomers or diastereoisomers. These enantiomers, diastereoisomers, as well as their mixtures, including racemic mixtures, are part of the invention;

The compounds of formula (Ia) or (Ib) may include one or several E/Z type stereochemistries on double bonds or cis/trans bonds on non-aromatic rings. These different stereoisomers as well as their mixture are part of the invention;

The compounds of formula (Ia) or (Ib) may exist as a salt, such salts are part of the invention;

these salts may be prepared with pharmaceutically acceptable acids or bases (P. Stahl, C. Wermuth; Handbook of pharmaceutical salts; Wiley Ed.), but other salts for example obtained by purification or isolation of compounds of formula (Ia) or (Ib) are part of the invention.

It may be recalled that stereoisomery may be defined in its broad sense as isomery of compounds having the same structural formulae, but for which the different groups are positioned differently in space, such as notably in mono-substituted cyclohexanes, for which the substituent may be in an axial or equatorial position, and the different possible rotational conformations of the derivatives of ethane. However, there exists another type of stereoisomery, due to different spatial arrangements of set substituents, either on double bonds, or on rings, which are often called geometrical isomery or cis-trans isomery. The term of stereoisomers is used in the present application in its broadest sense and therefore relates to the whole of the compounds indicated above.

The object of the present invention is further any method for preparing products of formulae (Ia) and (Ib) as defined above.

The products according to the invention may be prepared from conventional organic chemistry methods.

The object of the present invention is thus notably a method for synthesizing products of formula (Ia) as defined above, described in the general scheme 1a.

Preparation of Compounds of Formula (Ia)

The general scheme 1a below is illustrative of the methods used for preparing the products of formula (Ia). As such, they should not be a limitation of the scope of the invention, as regards the claimed methods for preparing the compounds.

The products of formula (Ia) as defined above according to the present invention may thus be notably prepared according to the method described in the general scheme 1a.

The object of the present invention is thus also the method for preparing products of formula (Ia) according to the general scheme 1a as defined hereafter.

General Scheme 1a:

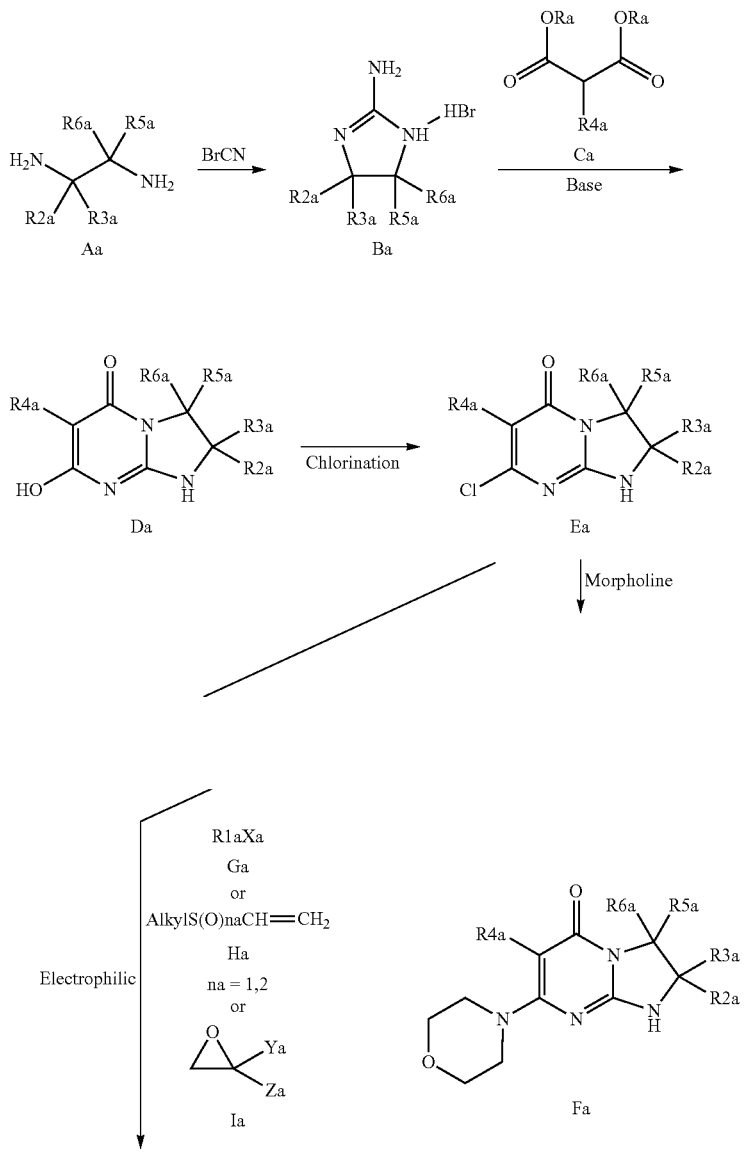

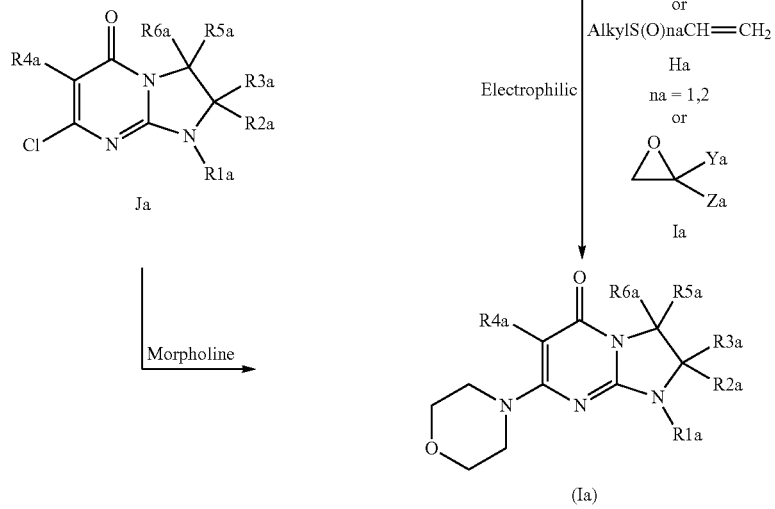
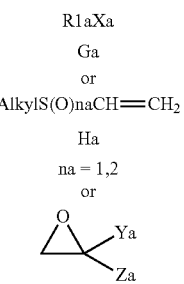
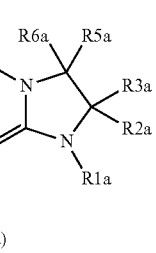

wherein the substituents R1a, R2a, R3a, R4a, R5a and R6a have the meanings indicated above for the products of formula (Ia).

In the General Scheme 1a:

The diamines Aa are either commercial or prepared in an achiral, chiral or racemic version, according to the methods known to one skilled in the art such as those notably according to the method described by Brigaud, T. et al. in J. Org. Chem. 2006, 71(18), 7075-7078, when R2a=CF$_3$ and R3a=Me or by analogy with this same reference for the other values of R2a and R3a as defined above.

Alternatively, the diamines Aa may be obtained according to methods known to one skilled in the art such as notably by a Strecker type reaction between a ketone and an amine in the presence of trimethylsilyl cyanide followed by reduction of the nitrile group into an amine as for example reported by Larock, Richard, C. et al. in Comprehensive Organic Transformations A Guide to Functional Group Preparations at VCH.

The guanidines Ba are either commercial or for example prepared by reaction of a diamine Aa and of cyanogen bromide in a solvent such as water or acetonitrile, at a temperature comprised between 0° C. and the boiling point of the solvent, according to the conditions for example described by Gallet, T. et al. (EP1340761 2003).

The compounds Da may notably be obtained by fusion of a guanidine Ba with a dialkyl malonate (preferably diethyl malonate) Ca, in the presence of a base such as sodium methylate, at a temperature comprised between 0° C. and 150° C., as for example described by Badawey E.-S. A. M. et al. (Eur J Med Chem, 1998, 33(5), 349-361.

The compounds Ea may be notably obtained from a compound Da by treatment with a chlorination agent such as phosphorus oxychloride, in the absence of a solvent, at a temperature comprised between 20° C. and 150° C., or in the presence of a solvent such as dichloroethane, at a temperature comprised between 20° C. and the boiling temperature of the solvent, such as for example under the conditions described by Yamashita, A. et al. (Syn. Commun. (2004), 34(5), 795-803)

The compounds Fa may notably be obtained from a compound Ea by reaction with morpholine, in the absence of solvent, at a temperature comprised between 20° C. and 150° C., or in the presence of a solvent such as acetonitrile, at a temperature comprised between 20° C. and the reflux temperature of the solvent, either in the presence or not of a base such as sodium carbonate, for example, as for example described by Aliabiev S. B. (Lett. Org. Chem. (2007), 4(4), 273-280).

The compounds (Ia) may be notably obtained by reaction between a compound Fa and an electrophilic agent.

The compounds (Ia) may notably be obtained for example by an alkylation reaction by adding a compound Ga (R1a-Xa with R1a representing a linear or branched or cyclic or heterocyclic alkyl radical as defined above and Xa=Cl, Br, I, OMs, OTs or OTf in the case of an alkylation) onto a mixture of a compound Fa and of a base such as an excess of sodium hydride or cesium carbonate, in a solvent such as tetrahydrofurane, N,N-dimethylformamide or acetonitrile, at a temperature comprised between 0° C. and 200° C., as for example described by Ting P. C. et al. (J. Med. Chem. (1990), 33(10), 2697-2706) in the case of an alkylation reaction.

Alternatively, the compounds (Ia) may for example be obtained by an addition reaction of the Michael type of a compound Fa on a compound Ha (alkylS(O)naCH=CH$_2$ as defined above with na=1, 2), in the presence of a base such as potassium phosphate or cesium carbonate for example, in a solvent such as acetonitrile, at a temperature comprised between 0° C. and 200° C., following by analogy the procedure as described by Wallace, Eli M. et al. (US2004/116710 A1) and Wallace, Eli M. et al. (US2003/232869 A1) and Ishikawa, T. et al. (US2009/233937 A1) for example.

Alternatively, the compounds (Ia) may for example be obtained by an alkylation reaction by adding a compound Ia (epoxyethylene disubstituted in position 1 with substituents Ya, Za representing a hydrogen or a linear alkyl radical as defined above, preferably methyl) onto a mixture of a compound Fa and of a base such as excess cesium or potassium carbonate, in a solvent such as tetrahydrofurane, N,N-dimethylformamide, N,N-dimethylacetamide or acetonitrile, at a temperature comprised between 0° C. and 200° C., as for example described by Maekawa, T. et al. (US2010/197683, WO2010/87515) for example.

Alternatively, the compounds (Ia) may for example be obtained from a compound Ja by reaction with morpholine, in the absence of solvent at a temperature comprised between 20° C. and 120° C., or in presence of a solvent such as acetonitrile, at a temperature comprised between 20° C. and the reflux temperature of the solvent, as for example described by Aliabiev S. B. (Lett. Org. Chem. (2007), 4(4), 273-280.

The compounds Ja may notably be obtained by an alkylation reaction by adding a compound Ga (R1a-Xa with R1a representing a linear or branched or cyclic or heterocyclic alkyl radical as defined above and Xa=Cl, Br, I, OMs, OTs or OTf in the case of an alkylation) onto a mixture of a compound Ea and of a base such as sodium hydride or excess cesium carbonate, in a solvent such as tetrahydrofurane, N,N-dimethylformamide or acetonitrile, at a temperature comprised between 0° C. and 200° C., as for example described by Ting P. C. et al. (J. Med. Chem. (1990), 33(10), 2697-2706) in the case of the alkylation reaction.

Alternatively, the compounds Ja may be notably obtained by an addition reaction of the Michael type of a compound Ea onto a compound Ha (alkylS(O)naCH=CH$_2$ as defined above with na=1, 2), in the presence of a base such as potassium phosphate or cesium carbonate for example, in a solvent such as acetonitrile, at a temperature comprised between 0° C. and 200° C., by following by analogy the procedure as described by Wallace, Eli M. et al. (US2004/116710 A1) and Wallace, Eli M. et al. (US2003/232869 A1) and Ishikawa, T. et al. (US2009/233937 A1) for example.

Alternatively, the compounds Ja may for example be obtained by an alkylation reaction by addition of a compound Ia (epoxyethylene disubstituted in position 1 with substituents Ya,Za representing a hydrogen or a linear alkyl radical as defined above, preferably a methyl) on a mixture of a compound Fa and of a base such as excess cesium or potassium carbonate, in a solvent such as tetrahydrofurane, N,N-dimethylformamide, N,N-dimethylacetamide or acetonitrile, at a temperature comprised between 0° C. and 200° C., by analogy with the procedure as described by Maekawa, T. et al. (US2010/197683, WO2010/87515) for example.

In the cases when R2a is different from R3a and if the synthesis is not stereoselective, the enantiomers or the possible diastereoisomers of the synthesis intermediates or of the compounds (Ia) may be separated by chromatography on a chiral support.

The following examples of products of formula (Ia) illustrate the invention without however limiting it.

Among the starting products of formula Aa, Ba, Ca, Ga, Ha or Ia, some are known and may either be obtained commercially or according to usual methods known to one skilled in the art as for example described by Larock, Richard, C. et al. in Comprehensive Organic Transformations A Guide to Functional Group Preparations at VCH, for example from commercial products.

It is understood for one skilled in the art that, for applying the methods according to the invention described earlier, it may be necessary to introduce protective groups for functions as for example described by Greene, Theodora W. et al. in Protective Groups in Organic Synthesis at Wiley-Interscience.

It may be noted that it is possible, if desired and if necessary, to subject intermediate products or products of formula (Ia), thereby obtained with the methods indicated above, in order to obtain other intermediates or other products of formula (Ia), to one or several transformation reactions known to one skilled in the art as for example described by Larock, Richard, C. et al. in Comprehensive Organic Transformations A Guide to Functional Group Preparations at VCH.

The object of the present invention is also a method for synthesizing products of formula (Ib) defined above, described in the general scheme 1b.

Preparation of Compounds of Formula (Ib)

The general scheme 1b below is illustrative of the methods used for preparing the products of formula (Ib). As such, they cannot be a limitation of the scope of the invention, as regards the methods for preparing the claimed compounds.

The products of formula (Ib) as defined above according to the present invention may thus be notably prepared according to the method described in the general scheme 1b.

The object of the present invention is thus also the method for preparing products of formula (Ib) according to the general scheme 1b as defined hereafter.

General Scheme 1b:

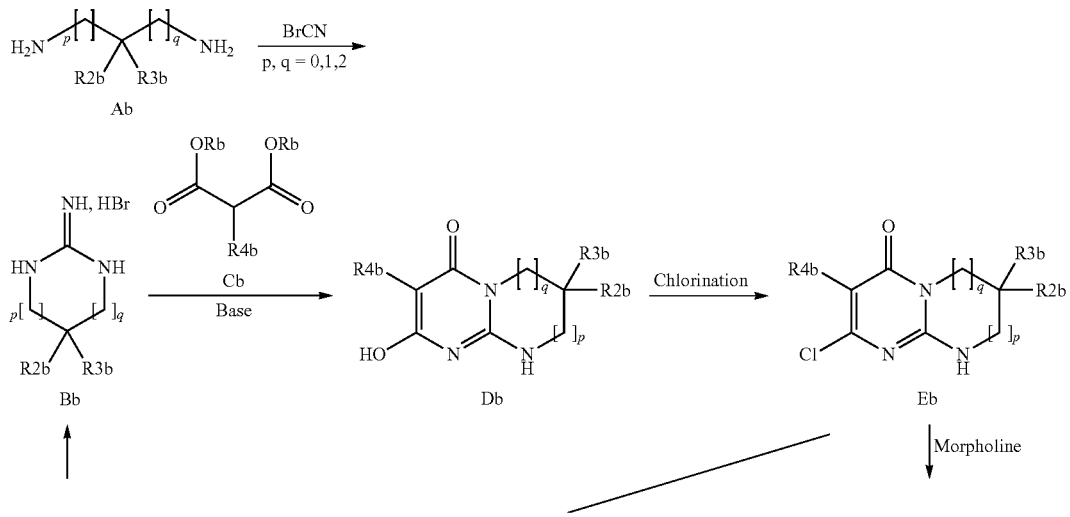

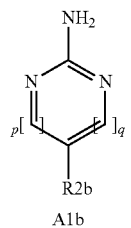

A1b

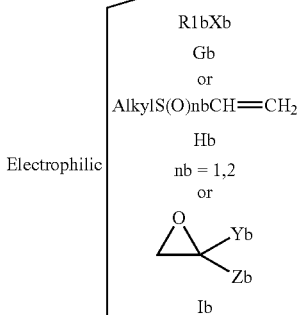

Ib

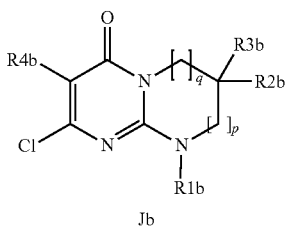

Jb

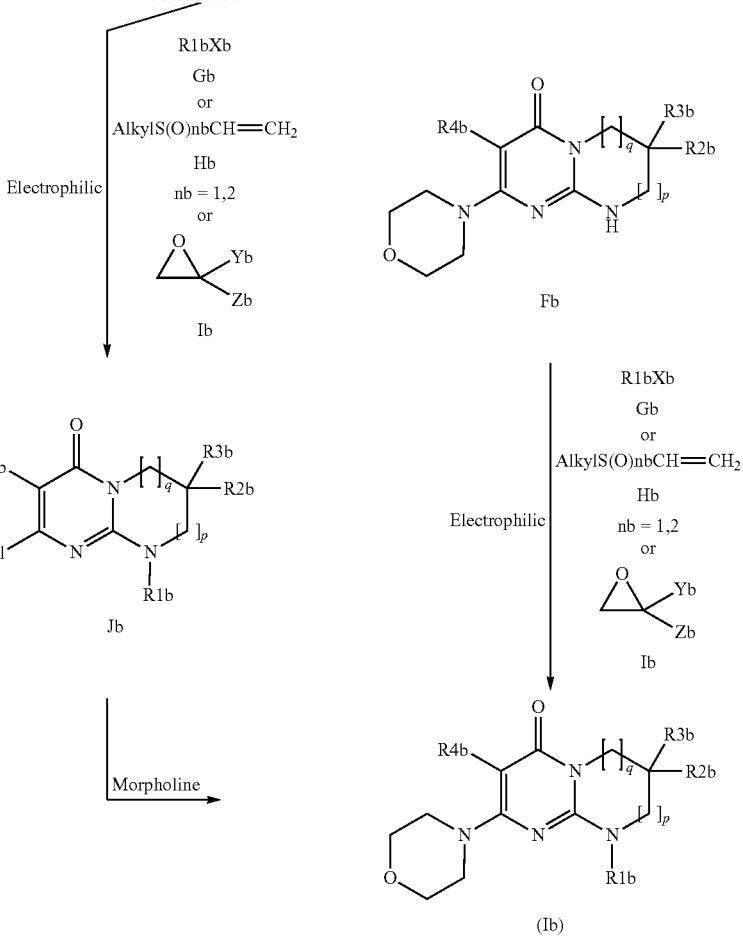

(Ib)

wherein the substituents p, q, R1b, R2b, R3b and R4b have the meanings indicated above for the products of formula (Ib).

In the General Scheme 1b:

The diamines Ab are either commercial or prepared in an achiral, chiral or racemic version, according to methods known to one skilled in the art such as notably by analogy and in approval with the method described by Brigaud, T. et al. in J. Org. Chem. 2006, 71(18), 7075-7078, for the values of R2b and R3b as defined above.

Alternatively, the diamines Ab may be obtained according to methods known to one skilled in the art such as notably by analogy with literature as for example reported by Carreira, E. M. et al. in Angew. Chem. Int. Ed. 2010, 49, 9052-9067 and in Organic Letters 2010, 1944-1947, for the values of R2b and R3b as defined above.

Alternatively, the symmetrical diamines Ab are either commercial or prepared according to methods known to one skilled in the art such as notably from commercial symmetric diols by transformation of the hydroxyl groups into a leaving group such as halides or mesylates or tosylates followed by double substitution with a nitrogen-containing reagent as for example described by Larock, Richard, C. et al. in Comprehensive Organic Transformations A Guide to Functional Group Preparations at VCH, for the values of R2b and R3b as defined above.

The guanidines Bb (p=0, q=2) are either commercial or prepared from A1b according to methods known to one skilled in the art such as notably according to the methods described in Lochead, A. W. et al. (EP1460076 2002), Lochead, A. W. et al. (EP1340761 2003), Lochead, A. W. et al. (EP1454909 2004) and Lochead, A. W. et al. (WO2005058908 2005) or by analogy with this same reference in the other cases.

The guanidines Bb may be notably obtained by reaction of a diamine Ab and of cyanogen bromide in a solvent such as water or acetonitrile, at a temperature comprised between 0° C. and a boiling point of the solvent, according to the conditions described for example by Gallet, T. et al. (EP1340761 2003).

The compounds Db may notably be obtained by fusion of a guanidine Bb with a dialkyl malonate (preferably diethyl malonate) Cb, in the presence of a base such as sodium methylate, at a temperature comprised between 0° C. and 150° C., as for example described by Badawey E.-S. A. M. et al. (Eur J Med Chem, 1998, 33(5), 349-361.

The compounds Eb may be notably obtained from a compound Db by treatment with a chlorination agent such as phosphorus oxychloride, in the absence of solvent, at a temperature comprised between 20° C. and 150° C., or in the presence of a solvent such as dichloroethane, at a temperature comprised between 20° C. and the boiling point of the solvent, such as for example under the conditions described by Yamashita, A. et al. (Syn. Commun. (2004), 34(5), 795-803)

The compounds Fb may be notably obtained from a compound Eb by reaction with morpholine, in the absence of a solvent, at a temperature comprised between 20° C. and 150° C., or in the presence of a solvent such as acetonitrile, at a temperature comprised between 20° C. and the reflux temperature of the solvent, either in the presence or not of a base such as sodium carbonate, for example, as for example as described by Aliabiev S. B. (Lett. Org. Chem. (2007), 4(4), 273-280).

The compounds (Ib) may notably be obtained by reaction between a compound Fb and an electrophilic agent.

The compounds (Ib) may notably be obtained for example by an alkylation reaction by addition of a compound Gb (R1b-Xb with R1b representing a linear or branched or cyclic or heterocyclic alkyl radical as defined above and Xb=Cl, Br, I, OMs, OTs or OTf in the case of an alkylation) onto a mixture of a compound Fb and of a base such as sodium hydride or excess cesium carbonate, in a solvent such as tetrahydrofurane, N,N-dimethylformamide or acetonitrile, at a temperature comprised between room temperature and 200° C., as for example described by Ting P. C. et al. (J. Med. Chem. (1990), 33(10), 2697-2706) in the case of an alkylation reaction.

Alternatively, the compounds (Ib) may for example be obtained by an addition reaction of the Michael type of a compound Fb onto a compound Hb (alkylS(O)nbCH=CH$_2$ as defined above with nb=1, 2), in the presence of a base such as potassium phosphate or cesium carbonate for example, in a solvent such as acetonitrile, at a temperature comprised between 0° C. and 200° C., while following by analogy the procedure as described by Wallace, Eli M. et al. (US2004/116710 A1) and Wallace, Eli M. et al. (US2003/232869 A1) and Ishikawa, T. et al. (US2009/233937 A1) for example.

Alternatively, the compounds (Ib) may for example be obtained by an alkylation reaction by adding a compound Ib (epoxyethylene disubstituted in position 1 with substituents Yb,Zb representing a hydrogen or a linear alkyl radical as defined above, preferably a methyl) onto a mixture of a compound Fb and of a base such as excess cesium or potassium carbonate, in a solvent such as tetrahydrofurane, N,N-dimethylformamide, N,N-dimethylacetamide or acetonitrile, at a temperature comprised between 0° C. and 200° C., as for example described by Maekawa, T. et al. (US2010/197683, WO2010/87515) for example.

Alternatively, the compounds (Ib) may for example be obtained from a compound Jb by reaction with morpholine, in the absence of a solvent, at a temperature comprised between 20° C. and 120° C., or in the presence of a solvent such as acetonitrile, at a temperature comprised between 20° C. and the reflux temperature of the solvent, either in the presence or not of a base such as sodium carbonate for example, as for example described by Aliabiev S. B. (Lett. Org. Chem. (2007), 4(4), 273-280.

The compounds Jb may notably be obtained by an alkylation reaction by adding a compound Gb (R1b-Xb with R1b representing a linear or branched or cyclic or heterocyclic alkyl radical as defined above and Xb=Cl, Br, I, OMs, OTs or OTf in the case of an alkylation) onto a mixture of a compound Eb and of a base such as sodium hydride or excess cesium carbonate, in a solvent such as tetrahydrofurane, N,N-dimethylformamide or acetonitrile, at a temperature comprised between 0° C. and 200° C., as for example described by Ting P. C. et al. (J. Med. Chem. (1990), 33(10), 2697-2706) in the case of the alkylation reaction.

Alternatively, the compounds Jb may notably be obtained by an addition reaction of the Michael type of a compound Eb on a compound Hb (alkylS(O)nbCH=CH$_2$ as defined above with nb=1, 2), in the presence of a base such as potassium phosphate or cesium carbonate for example, in a solvent such as acetonitrile, at a temperature comprised between 0° C. and 200° C., while following by analogy the procedure as described by Wallace, Eli M. et al. (US2004/116710 A1) and Wallace, Eli M. et al. (US2003/232869 A1) and Ishikawa, T. et al. (US2009/233937 A1) for example.

Alternatively, the compounds Jb may for example be obtained by an alkylation reaction by adding a compound Ib (epoxyethylene disubstituted in position 1 with substituents Yb,Zb representing a hydrogen or a linear alkyl radical as defined above, (preferably a methyl) onto a mixture of a compound Fb and of a base such as excess cesium or potassium carbonate, in a solvent such as tetrahydrofurane, N,N-dimethylformamide, N,N-dimethylacetamide or acetonitrile, at a temperature comprised between 0° C. and 200° C., by analogy with the procedure as described by Maekawa, T. et al. (US2010/197683, WO2010/87515) for example.

In the cases when R2b is different from R3b and if a synthesis is not stereoselective, the enantiomers or the possible diastereoisomers of the synthesis intermediates or of the compounds (Ib) may be separated by chromatography on a chiral support.

The following examples of products of formula (Ib) illustrate the invention without however limiting it.

Among the starting products of formula Ab, Bb, Cb, Gb, Hb or Ib, some are known and may be obtained either commercially or according to the usual methods known to one skilled in the art as for example described by Larock, Richard, C. et al. in Comprehensive Organic Transformations A Guide to Functional Group Preparations at VCH, for example from commercial products.

It is understood for one skilled in the art that, for applying the methods according to the invention described earlier, it may be necessary to introduce protective groups for functions as for example described by Greene, Theodora W. et al. in Protective Groups in Organic Synthesis at Wiley-Interscience.

It may be noted that if desired and if necessary it is possible to subject intermediate products or products of formula (Ib), thereby obtained by the methods indicated above, in order to obtain other intermediates or other products of formula (Ib), to one or several transformation reactions known to one skilled in the art as for example described by Larock, Richard, C. et al. in Comprehensive Organic Transformations A Guide to Functional Group Preparations at VCH.

The products of formula (Ia) or (Ib) as defined above as well as their addition salts with acids have interesting pharmacological properties notably because of their inhibitory properties for kinases as this is indicated above.

The products of the present invention are notably useful for anti-tumoral therapies.

The products of the invention may thus also increase the therapeutic effects of currently used anti-tumoral agents.

The products of the invention may thus also increase the therapeutic effects of currently used radiotherapies.

These properties justify their application in therapeutics and the object of the invention is particularly as a drug, the products of formula (Ia) or (Ib) as defined above, said products of formula (Ia) or (Ib) being under all the racemic, enantiomeric and diastereoisomeric possible isomeric forms, as well as addition salts with inorganic and organic acids or with inorganic and organic bases which are pharmaceutically acceptable, of said products of formula (Ia) or (Ib).

The object of the invention is most particularly as drugs, the products of formula (Ia) having the following formulae:
- (2S)-1-(2-Ethylbutyl)-2-methyl-7-(morpholin-4-yl)-2-(trifluoromethyl)-2,3-dihydroimidazo[1,2-a]pyrimidin-5(1H)-one
- (2S)-1-Cyclopropyl-2-methyl-7-(morpholin-4-yl)-2-(trifluoromethyl)-2,3-dihydroimidazo[1,2-a]pyrimidin-5(1H)-one
- (2S)-1-Cyclopentyl-2-methyl-7-(morpholin-4-yl)-2-(trifluoromethyl)-2,3-dihydroimidazo[1,2-a]pyrimidin-5(1H)-one
- (S)-1-(2-Isopropoxy-ethyl)-2-methyl-7-(morpholin-4-yl)-2-(trifluoromethyl)-2,3-dihydroimidazo[1,2-a]pyrimidin-5(1H)-one
- (S)-1-(2-Hydroxy-2-methyl-propyl)-2-methyl-7-(morpholin-4-yl)-2-(trifluoromethyl)-2,3-dihydroimidazo[1,2-a]pyrimidin-5(1H)-one
- (S)-1-(2-Methoxy-2-methyl-propyl)-2-methyl-7-(morpholin-4-yl)-2-(trifluoromethyl)-2,3-dihydroimidazo[1,2-a]pyrimidin-5(1H)-one
- 1-(2-Isopropoxyethyl)-2,2-dimethyl-7-(morpholin-4-yl)-2,3-dihydroimidazo[1,2-a]pyrimidin-5(1H)-one
- 1'-(2-Methoxyethyl)-7'-morpholin-4-ylspiro[cyclopentane-1,2'-imidazo[1,2-a]pyrimidin]-5'-one
- 1'-(2-Isopropoxyethyl)-7'-morpholin-4-ylspiro[cyclopentane-1,2'-imidazo[1,2-a]pyrimidin]-5'-one as well as pharmaceutically acceptable addition salts with inorganic and organic acids or with inorganic and organic bases of the products of formula (Ia).

The object of the invention is most particularly, as drugs, the products of formula (Ib) having the following formulae:
- (8S)-9-(2-Ethylbutyl)-2-(morpholin-4-yl)-8-(trifluoromethyl)-6,7,8,9-tetrahydro-4H-pyrimido[1,2-a]pyrimidin-4-one
- (8S)-9-(Cyclopropylmethyl)-2-(morpholin-4-yl)-8-(trifluoromethyl)-6,7,8,9-tetrahydro-4H-pyrimido[1,2-a]pyrimidin-4-one
- (8S)-9-Cyclopentyl-2-(morpholin-4-yl)-8-(trifluoromethyl)-6,7,8,9-tetrahydro-4H-pyrimido[1,2-a]pyrimidin-4-one
- (8S)-9-(2-Hydroxyethyl)-2-(morpholin-4-yl)-8-(trifluoromethyl)-6,7,8,9-tetrahydro-4H-pyrimido[1,2-a]pyrimidin-4-one
- (S)-9-(2-Isopropoxy-ethyl)-2-(morpholin-4-yl)-8-trifluoromethyl-6,7,8,9-tetrahydro-4H-pyrimido[1,2-a]pyrimidin-4-one
- (S)-2-(Morpholin-4-yl)-9-[2-(2,2,2-trifluoro-ethoxy)-ethyl]-8-(trifluoromethyl)-6,7,8,9-tetrahydro-4H-pyrimido[1,2-a]pyrimidin-4-one
- (8S)-3-Fluoro-9-(2-isopropoxy-ethyl)-2-(morpholin-4-yl)-8-(trifluoromethyl)-6,7,8,9-tetrahydro-4H-pyrimido[1,2-a]pyrimidin-4-one
- (8S)-9-(2-Hydroxy-2-methylpropyl)-2-(morpholin-4-yl)-8-(trifluoromethyl)-6,7,8,9-tetrahydro-4H-pyrimido[1,2-a]pyrimidin-4-one
- (S)-9-(2-Hydroxy-2-methyl-propyl)-3-methyl-2-(morpholin-4-yl)-8-trifluoromethyl-6,7,8,9-tetrahydro-4H-pyrimido[1,2-a]pyrimidin-4-one
- (S)-9-(2-Methoxy-2-methyl-propyl)-2-(morpholin-4-yl)-8-trifluoromethyl-6,7,8,9-tetrahydro-4H-pyrimido[1,2-a]pyrimidin-4-one
- (8S)-8-Methyl-2-(morpholin-4-yl)-9-(2-(propan-2-yloxy)ethyl)-8-(trifluoromethyl)-6,7,8,9-tetrahydro-4H-pyrimido[1,2-a]pyrimidin-4-one
- (8R)-8-Methyl-2-(morpholin-4-yl)-9-(2-(propan-2-yloxy)ethyl)-8-(trifluoromethyl)-6,7,8,9-tetrahydro-4H-pyrimido[1,2-a]pyrimidin-4-one
- 9-(2-Methoxyethyl)-8,8-dimethyl-2-(morpholin-4-yl)-6,7,8,9-tetrahydro-4H-pyrimido[1,2-a]pyrimidin-4-one
- 9-(2-Isopropoxyethyl)-8,8-dimethyl-2-(morpholin-4-yl)-6,7,8,9-tetrahydro-4H-pyrimido[1,2-a]pyrimidin-4-one
- 9-(2-Methoxyethyl)-7,7-dimethyl-2-(morpholin-4-yl)-6,7,8,9-tetrahydro-4H-pyrimido[1,2-a]pyrimidin-4-one
- 9-(2-Isopropoxyethyl)-7,7-dimethyl-2-(morpholin-4-yl)-6,7,8,9-tetrahydro-4H-pyrimido[1,2-a]pyrimidin-4-one
- 1'-(2-Isopropoxyethyl)-8'-(morpholin-4-yl)-1',2'-dihydro-spiro[cyclopropane-1,3'-pyrimido[1,2-a]pyrimidin]-6'-one
- (8S)-9-(2-Methanesulfonyl-ethyl)-2-morpholin-4-yl-8-trifluoromethyl-6,7,8,9-tetrahydro-pyrimido[1,2-a]pyrimidin-4-one as well as pharmaceutically acceptable addition salts with inorganic and organic acids or with inorganic and organic bases of said products of formula (Ib).

The invention also relates to pharmaceutical compositions containing as an active ingredient at least one of the products of formula (Ia) or (Ib) as defined above or a pharmaceutically acceptable salt of this product or a prodrug of this product and if necessary, a pharmaceutically acceptable carrier.

The invention thus extends to the pharmaceutical compositions containing as an active ingredient, at least one of the drugs as defined above.

Such pharmaceutical compositions of the present invention may also if necessary contain active ingredients of other antimitotic drugs such as notably those based on taxol, cisplatine, DNA intercalating agents and other agents.

These pharmaceutical compositions may be administered via a buccal route, via a parenteral route or via a local route as a topical application on the skin and the mucosas or by injection via an intravenous or intramuscular route.

These compositions may be solid or liquid and appear in all the pharmaceutical forms currently used in human medicine such as for example simple or sugar-coated tablets, pills, tablets, gelatine capsules, drops, granules, injectable preparations, pomades, creams or gels; they are prepared according to the usual method. The active ingredient may be incorporated therein to excipients customarily used in these pharmaceutical compositions, such as talcum, gum arabic, lactose, starch, magnesium stearate, cocoa butter, carriers either aqueous or not, fats of animal or vegetable origin, paraffinic derivatives, glycol, various wetting agents, dispersants or emulsifiers, preservatives.

The usual dosage, variable according to the product used, the treated subject and the relevant disease, may for example be from 0.05 to 5 g per day for adults, or preferably from 0.1 to 2 g per day.

The object of the present invention is also the use of products of formula (Ia) or (Ib) as defined above for preparing a drug intended for treating or preventing a disease characterized by the disruption of the activity of a protein or of a lipid kinase.

Such a drug may notably be intended for treating or preventing a disease in a mammal.

The object of the present invention is notably the use of a product of formula (Ia) or (Ib) as defined earlier for preparing a drug intended for preventing or treating diseases related to uncontrolled proliferation.

The object of the present invention is thus most particularly the use of a product of formula (Ia) or (Ib) as defined above for preparing a drug intended for treating or preventing diseases in oncology and notably intended for treating cancers. The object of the present invention is products of formula (Ia) or (Ib) as defined above for their use for treating solid or liquid tumors.

The mentioned products of the present invention may notably be used for treating primary tumors and/or metastases in particular in gastric, liver, kidney, ovarian, colon, prostate, endometrium, lung cancers (NSCLC and SCLC), glioblastomas, thyroid, bladder, breast cancers, in melanoma, in lymphoid or myeloid hematopoietic tumors in sarcomas, in cancers of the brain, of the larynx, of the lymphatic system, cancers of bones and of the pancreas, in harmartomas.

The object of the present invention is also the use of products of formula (Ia) or (Ib) as defined above for preparing drugs intended for chemotherapy of cancers. The object of the present invention is therefore the products of formulae (Ia) and (Ib) as defined above for their use for chemotherapy of cancers, either alone or as a combination. The products of the present application may notably be administered alone or as a combination with chemotherapy or radiotherapy or further as a combination for example with other therapeutic agents. Such therapeutic agents may be currently used anti-tumoral agents.

A therapeutic benefit may notably be expected by administering the products of the present application in combinations with various target therapies. These targeted therapies are notably the following: i) targeted therapies inhibiting kinases or pseudo-kinases like EGFR, HER2, HER3, PI3K, AKT, mTOR, Bcr-Abl, Kit, PDGFR, Src (Q W. Fan et al., Since signaling 2010, A. Gupta et al. PNAS 2010, X Li et al. Cancer Res 2010, A Vazquez-Martin et al. PLos One 2009, Z. Wu et al. Genes Cancer 2010) ii) the targeted therapies inhibiting the receptor for estrogen, the proteasome, the HDAC protein (J S Samaddar et al. Mol Cancer Ther 2008, B; Hoang et al. Mol Cancer Ther 2009, J S Carew et al. Blood 2007). A therapeutic effect may also be expected by combining the products of the present application with chemotherapy agents such as camptothecin, 5-FU for example; or else in combination with radiotherapy (J Li et al. Eur J of Cancer 2010, A. Appel et al. Cancer Res. 2008).

The object of the present invention is notably the use of a product of formula (Ia) or (Ib) as defined above for preparing a drug intended for preventing or treating lysosomal diseases such as type II glycogenosis (or Pompe's disease), Danon's disease, for example (N. Raben et al., Autophagy 2010, B. Levine et al. Cell 2008, N. Mizushima et al. Nature 2008). Such drugs intended for treating lysosomal diseases may be used alone or as a combination for example with other therapeutic agents.

The object of the present invention is also the use of a product of formula (Ia) or (Ib) as defined above for preparing a drug intended for preventing or treating X-linked myotubular myopathies, Charcot-Marie-Tooth's diseases; where mutations of the protein from the family of myotubularins have been described (I. Vergne et al., FEBS Lett., 2010). The object of the present invention is thus the use as defined above in which said products of formula (Ia) or (Ib) are alone or combined.

Among these cancers, the treatment of solid or liquid tumors is of interest in the treatment of cancers which resist cytotoxic agents.

The products of the present application may notably be administered alone or as a combination with chemotherapy or radiotherapy or further as a combination with other therapeutic agents for example.

Such therapeutic agents may be commonly used anti-tumoral agents.

As inhibitors of kinases, mention may be made of butyrolactone, flavopiridol, 2(2-hydroxyethylamino)-6-benzylamino-9-methylpurine called olomucin, sorafenib, imatinib, erlotinib, gefitinib and Lapatinib.

Thus the present application notably relates to the products of formulae (Ia) or (Ib) as defined above for their use for treating cancers.

Thus the present application notably relates to the products of formulae (Ia) or (Ib) as defined above for their use for treating sold or liquid tumors.

Thus the present application notably relates to the products of formulae (Ia) or (Ib) as defined above for their use for treating cancers which resist cytotoxic agents.

Thus the present application notably relates to the products of formulae (Ia) or (Ib) as defined above for their use for treating primary tumors and/or metastases in particular in gastric, liver, kidney, ovarian, colon, prostate, lung cancers (NSCLC and SCLC), glioblastomas, thyroid, bladder, breast cancers, in melanoma, in lymphoid or myeloid hematopoietic tumors, in sarcomas, in cancers of the brain, larynx, lymphatic system, cancers of the bones and of the pancreas, in harmartomas.

Thus the present application notably relates to the products of formulae (Ia) or (Ib) as defined above, for their use for chemotherapy of cancers.

Thus the present application notably relates to the products of formulae (Ia) or (Ib) as defined above, for their use for chemotherapy of cancers alone or as a combination.

Thus the present application notably relates to the products of formulae (Ia) or (Ib) as defined above, for their use for treating lysosomal diseases such as type II glycogenosis (or Pompe's disease) or Danon's disease.

Thus the present application notably relates to the products of formulae (Ia) or (Ib) as defined above, for their use for treating X-linked myotubular myopathies, Charcot-Marie-Tooth diseases.

The object of the present invention as novel industrial products is the synthesis intermediates of formulae Da, Ea, Fa et Ja as defined above and recalled hereafter:

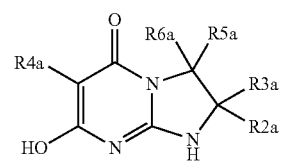

Da

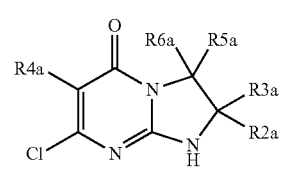

Ea

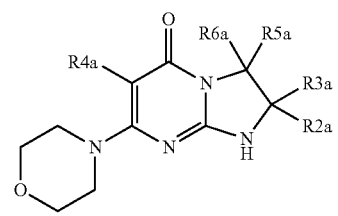

Fa

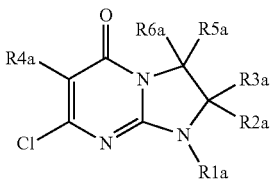

Ja wherein R1a, R2a, R3a, R4a, R5a and R6a have the definitions indicated above for the products of formula (Ia).

The object of the present invention is also as novel industrial products, the synthesis intermediates of formula Db, Eb, Fb and Jb as defined above and recalled hereafter:

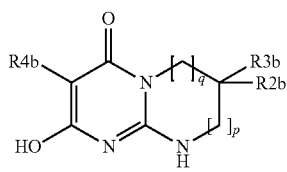

Db

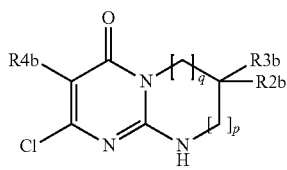

Eb

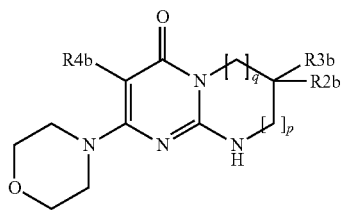

Fb

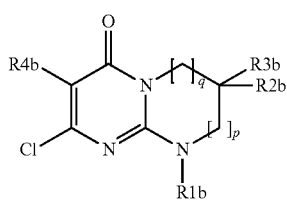

Jb wherein the substituents p, q, R1b, R2b, R3b and R4b have the definitions indicated above for the products of formula (Ib).

The following examples which are products of formulae (Ia) or (Ib) illustrate the invention without however limiting it.

EXPERIMENTAL PART

The nomenclature of the compounds of this present invention was carried out with the software package ACDLABS version 10.0.

The microwave oven used is a Biotage, Initiator™ Eight appliance, max 400 W, 2450 MHz.

The $^1$H NMR spectra at 400 MHz and $^1$H NMR spectra at 500 MHz were carried out on a BRUKER AVANCE 250 or BRUKER AVANCE DRX-400 or BRUKER AVANCE DPX-500 spectrometer with chemical shifts (δ in ppm) in the reference solvent dimethylsulfoxide-d$_6$ (DMSO-d$_6$) at 2.5 ppm at a temperature of 303K.

The mass spectra (MS) were obtained either by the method A, or by the method B.

Method A:

WATERS UPLC-SQD apparatus; ionization: electrospraying in positive and/or negative mode (ES+/−); Chromatographic conditions: Column: ACQUITY BEH C18 1.7 μm-2.1×50 mm; Solvents: A: H$_2$O (0.1% formic acid) B: CH$_3$CN (0.1% formic acid); Column temperature: 50° C.; Flow rate: 1 mL/min; Gradient (2 min): from 5 to 50% of B in 0.8 mins; 1.2 mins: 100% of B; 1.85 min: 100% of B; 1.9: 5% of B; Retention time=Rt (mins).

Method B:

WATERS ZQ apparatus: Ionization: electrospraying in positive and/or negative mode (ES+/−); Chromatographic conditions: Column: XBridge C18 2.5 μm-3×50 mm; Solvents: A: H$_2$O (0.1% formic acid) B: CH$_3$CN (0.1% formic acid); Column temperature: 70° C.; Flow rate: 0.9 mL/min; Gradient (7 mins): from 5 to 100% of B in 5.3 mins, 5.5 mins: 100% of B; 6.3 mins: 5% of B; Retention time=Rt (mins).

The rotatory powers (RP) were measured on a polarimeter Model 341 from Perkin Elmer. Wavelength: α line of sodium (589 nanometers).

Example 1a (2S)-1-(2-Ethylbutyl)-2-methyl-7-(morpholin-4-yl)-2-(trifluoromethyl)-2,3-dihydroimidazo[1,2-a]pyrimidin-5(1H)-one

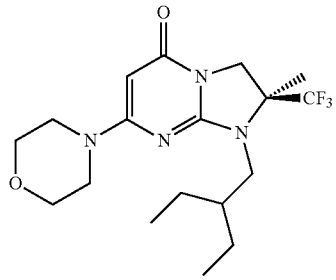 [SMILES: CCC(CC)CN1c2nc(N3CCOCC3)cc(=O)n2C[C@@]1(C)C(F)(F)F]

A suspension of 200 mg (0.657 mmol) of (2S)-2-methyl-7-(morpholin-4-yl)-2-(trifluoromethyl)-2,3-dihydroimidazo[1,2-a]pyrimidin-5(1H)-one, 542 mg (3.285 mmol) of 3-(bromomethyl)pentane and 1.392 g (4.271 mmol) of cesium carbonate in 5 cm$^3$ of DMF is heated with the microwave oven to 170° C. for 1 h 30 mins and then to 190° C. for 1 h. The reaction medium is diluted with 150 cm$^3$ of ethyl acetate and the organic phase is then washed with twice 10 cm$^3$ of distilled water and twice 10 cm$^3$ of an aqueous solution saturated with sodium chloride, dried on anhydrous magnesium sulfate, filtered and dry concentrated under reduced pressure (2.7 kPa). The obtained crude is purified by flash chromatography on silica [eluent: dichloromethane/methanol/acetonitrile (88/6/6 by volume)]. After evaporation of the fractions under reduced pressure, 197 mg of (2S)-1-(2-ethylbutyl)-2-methyl-7-(morpholin-4-yl)-2-(trifluoromethyl)-2,3-dihydroimidazo[1,2-a]-pyrimidin-5(1H)-one are obtained as a yellowish solid including the following characteristics:

$[\alpha]_D^{25}$ at 589 nm=+30+/−1.4 in DMSO; C=1.90 mg/mL

Mass spectrum (method A): ES+/−: [M+H]+: m/z 389

$^1$H NMR spectrum (400 MHz, δ in ppm, DMSO-d6): 0.81-0.92 (m, 6H); 1.16-1.35 (m, 4H); 1.62 (s, 3H); 1.82 (m, 1H); 3.12 (dd, J=8.4 and 14.4 Hz, 1H); 3.32 (m partly hidden, 1H);

3.41 (m, 4H); 3.61 (m, 4H); 3.91 (d broad, J=12.7 Hz, 1H); 4.11 (d, J=12.7 Hz, 1H); 4.87 (s, 1H).

(2S)-2-methyl-7-(morpholin-4-yl)-2-(trifluoromethyl)-2,3-dihydroimidazo[1,2-a]pyrimidin-5(1H)-one may be prepared in the following way.

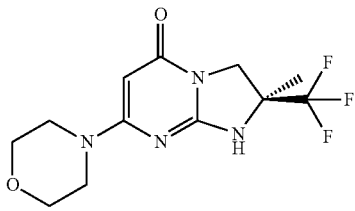 [SMILES: C[C@@]1(C(F)(F)F)Cn2c(nc(N3CCOCC3)cc2=O)N1]

A mixture of 2.2 g of (2S)-7-chloro-2-methyl-2-(trifluoromethyl)-2,3-dihydroimidazo[1,2-a]pyrimidin-5(1H)-one in 60 mL of morpholine is heated to 120° C. After one hour of heating and after monitoring with LC/MS, the reaction is completed. After cooling, the reaction mixture is concentrated under reduced pressure. On the obtained residue, 30 mL of cold water and 150 mL of ethyl acetate are added. The organic phase is then separated, dried on magnesium sulfate, filtered and then concentrated under reduced pressure in order to obtain 2.6 g of (2S)-2-methyl-7-(morpholin-4-yl)-2-(trifluoromethyl)-2,3-dihydroimidazo[1,2-a]pyrimidin-5(1H)-one including the following characteristics:

Mass spectrum (method B), ES+/−: [M+H]+: m/z 305; [M−H]−: m/z 303; Rt (min)=2.53

$[\alpha]_D^{25}$ at 589 nm=−9.0+/−0.6 (c=1.996710 mg/0.5 mL DMSO)

(2S)-7-chloro-2-methyl-2-(trifluoromethyl)-2,3-dihydroimidazo[1,2-a]pyrimidin-5(1H)-one may be prepared in the following way.

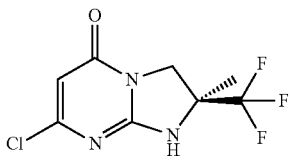 [SMILES: C[C@@]1(C(F)(F)F)Cn2c(nc(Cl)cc2=O)N1]

To a suspension of 5.6 g of (2S)-7-hydroxy-2-methyl-2-(trifluoromethyl)-2,3-dihydroimidazo[1,2-a]pyrimidin-5(1H)-one in 100 mL of 1,2-dichloroethane, are added at room temperature and under an argon atmosphere, 11 mL of phosphorus oxychloride. The resulting mixture is then heated to 70° C. After two hours of stirring and after monitoring with LC/MS, the reaction is completed. After cooling, the reaction mixture is dry evaporated under reduced pressure. The obtained residue is taken up with 5 mL of cold water and 200 mL of ethyl acetate. On the obtained mixture, 32% soda is added up to a pH=6. The organic phase is then separated and then dried on magnesium sulphate, filtered and concentrated under reduced pressure in order to obtain 6 g of (2S)-7-chloro-2-methyl-2-(trifluoromethyl)-2,3-dihydroimidazo[1,2-a]pyrimidin-5(1H)-one including the following characteristics:

Mass spectrum (method A), ES+/−: [M+H]+: m/z 254; [M−H]−: m/z 252; Rt (min)=0.51

$[\alpha]_D^{25}$ at 589 nm=−64.8+/−1.1 (c=2.2 mg/0.5 mL DMSO)

(2S)-7-hydroxy-2-methyl-2-(trifluoromethyl)-2,3-dihydroimidazo[1,2-a]pyrimidin-5(1H)-one may be prepared in the following way.

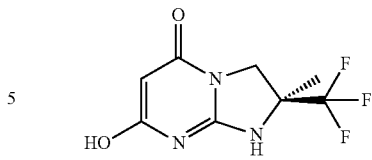

On a mixture of 5.4 g of diethyl malonate in 50 mL of methanol, are added 8.4 g of (2S)-4-methyl-4-(trifluoromethyl)-imidazolidin-2-ylidene amine hydrobromide and 2.16 g of sodium methylate. The resulting mixture is refluxed for 18 hours. After cooling, the obtained mixture is dry concentrated under reduced pressure. On the obtained residue, 20 mL of cold water are added in order to obtain a thick suspension onto which 25% hydrochloric acid is added until pH=5. The resulting suspension is stirred in an ice bath for two hours and then filtered on a glass frit. The obtained insoluble material is rinsed with water (2×4 mL) and then dried in order to obtain 5.6 g of (2S)-7-hydroxy-2-methyl-2-(trifluoromethyl)-2,3-dihydroimidazo[1,2-a]pyrimidin-5(1H)-one, as a white solid, including the following characteristics:

Mass spectrum (method A), ES+/−: [M+H]+: m/z 236; [M−H]−: m/z 234; Rt (min)=0.32

$[\alpha]_D^{25}$ at 589 nm=−5.6+/−0.6 (c=1.789 mg/0.5 mL DMSO)

(2S)-4-methyl-4-(trifluoromethyl)-imidazolidin-2-ylidene amine hydrobromide may be prepared in the following way.

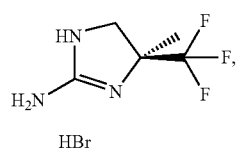

On a solution cooled to 5° C. of 2.3 g of (2S)-3,3,3-trifluoro-2-methyl-propane-1,2-diamine in 10 mL of water, 1.7 g of cyanogen bromide are added in small pieces while maintaining the temperature between 5 and 10° C. At the end of the addition, the reaction mixture is left at 5° C. for 30 minutes. The ice bath is then removed and the obtained mixture is stirred at room temperature for 3 hours. The resulting mixture is then concentrated under reduced pressure. The obtained residue is taken up twice with 100 mL of ethanol and then twice with 100 mL of toluene, with every time, dry evaporation. The obtained solid is titurated with ethyl ether and then filtered in order to obtain 4.5 g of (2S)-4-methyl-4-(trifluoromethyl)-imidazolidin-2-ylidene amine hydrobromide, as a white solid, including the following characteristics:

Mass spectrum (method A), ES+/−: [M+H]+: m/z 168; Rt (min)=0.14

$[\alpha]_D^{25}$ at 589 nm: −5.2+/−0.3 (c=4.909 mg/0.5 mL DMSO)

(2S)-3,3,3-trifluoro-2-methyl-propane-1,2-diamine may be prepared in the following way.

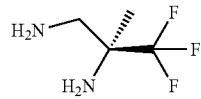

Into a flask, are introduced 4.8 g of (2S)-3,3,3-trifluoro-2-methyl-propane-1,2-diamine hydrochloride, 2.5 mL of water and 100 mL of ethyl ether. 4.5 mL of 32% soda are added dropwise on the resulting mixture until pH=12. The aqueous phase is then decanted and then extracted 4 times with 200 mL of ethyl ether. The organic phases are collected, dried on magnesium sulfate, filtered and then concentrated under reduced pressure (300 mbars/bath temperature=25° C.) in order to obtain 2.3 g of (2S)-3,3,3-trifluoro-2-methyl-propane-1,2-diamine, as a pale yellow oil, including the following characteristics:

Mass spectrum (method B), ES+/−: [M+H]+: m/z 143; base peak: m/z 126; Rt (min)=0.34

$[\alpha]_D^{25}$ at 589 nm=−4.3+/−0.6 (c=1.778 mg/0.5 mL DMSO)

(2S)-3,3,3-trifluoro-2-methyl-propane-1,2-diamine dihydrochloride may be prepared in the following way.

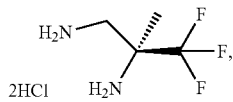

In an autoclave, a mixture of 7 g of (2R)-2-((S)-1-aminomethyl-2,2,2-trifluoro-1-methyl-ethylamino)-2-phenyl-ethanol in 40.5 mL of methanol, of 23.5 mL of 3 N hydrochloric acid and 0.94 g of Pd(OH)$_2$/C (20% w/w) is hydrogenated at 22° C., under a hydrogen pressure of bars and for 18 hours. The obtained mixture is then filtered and the filtrate dry evaporated. The obtained oil is taken up with a solution of 3 N hydrochloric acid (50 mL), the obtained mixture is extracted with diethyl ether (3×50 mL). The aqueous phase is then dry evaporated, taken up with methanol and then again dry evaporated. The obtained yellowish solid is dried in vacuo in order to lead to 5.54 g (79%) of (2S)-3,3,3-trifluoro-2-methyl-propane-1,2-diamine dihydrochloride, as an off-white solid, including the following characteristics:

$^1$H NMR spectrum (400 MHz, D2O): 1.55 (s, 3H), 3.40 (d, J=14.6 Hz, 1H), 3.51 (d, J=14.6 Hz, 1H).

$^{19}$F NMR (400 MHz, D$_2$O): −81.08 (non-calibrated with C$_6$F$_6$)

$[\alpha]_D^{25}$ at 589 nm=+4.65+/−0.6 (c=2.2; MeOH)

(2R)-2-((S)-1-Aminomethyl-2,2,2-trifluoro-1-methyl-ethylamino)-2-phenyl-ethanol may be prepared in the following way.

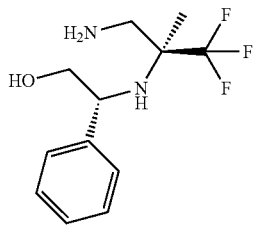 [SMILES: C[C@@](CN)(N[C@@H](CO)c1ccccc1)C(F)(F)F]

In a three-neck flask under argon, are added in small portions, 1.6 g of lithium aluminium hydride, on a solution cooled to 4° C., 2.5 g of (2S)-3,3,3-trifluoro-2-((R)-2-hydroxy-1-phenyl-ethylamino)-2-methyl-propionitrile in 250 mL of anhydrous ethyl ether. Strong gas evolvement is observed with a rise of the temperature to 8° C. At the end of the addition, the temperature is left to rise up to room temperature and then the reaction mixture is left with stirring for 18 h. The obtained mixture is cooled to 4° C. before adding dropwise and very slowly, 2 mL of water. Strong gas evolvement is observed with a rise of the temperature up to 12° C. To the resulting mixture maintained at 4° C., are added dropwise and very slowly, 2 mL of 15% potash and then, still dropwise and very slowly, 4 mL of water. The white precipitate formed is filtered and the obtained filtrate dried on magnesium sulfate and then concentrated under reduced pressure in order to obtain 2.2 g of (2R)-2-((S)-1-aminomethyl-2,2,2-trifluoro-1-methyl-ethylamino)-2-phenyl-ethanol including the following characteristics:

Mass spectrum (method A), ES+/−: [M+H]+: m/z 263; Rt (min)=0.43

$[\alpha]_d^{25}$ at 589 nm=−51.2+/−1.3 (c=1.576 mg/0.5 mL DMSO)

(2S)-3,3,3-trifluoro-2-((R)-2-hydroxy-1-phenyl-ethylamino)-2-methyl-propionitrile may be prepared in the following way.

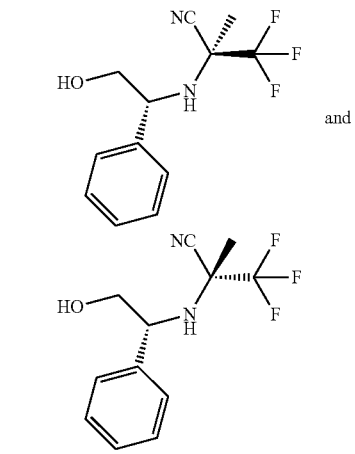

In a three-neck flask under argon, are added, dropwise, onto a solution cooled to 0° C. of 5.3 g of (2R,2S)-2-methyl-4-(R)-phenyl-2-(trifluoromethyl)-oxazolidine in 100 mL of dichloromethane, 3.4 g of trimethylsilyl cyanide, and then dropwise, 4.9 g of boron trifluoro etherate. The cold bath is then removed in order to let the temperature rise up to room temperature. The resulting mixture is left with stirring at room temperature for 18 hours before adding a solution saturated with sodium bicarbonate up to pH=8. The organic phase is separated and then dried on magnesium sulfate, filtered and concentrated under reduced pressure. The obtained residue is purified by chromatography on silica (eluent: cyclohexane/AcOEt:80/20) in order to obtain 3 g of (2R)-3,3,3-trifluoro-2-((R)-2-hydroxy-1-phenyl-ethylamino)-2-methyl-propionitrile, as a colorless oil et 2.5 g du (2S)-3,3,3-trifluoro-2-((R)-2-hydroxy-1-phenyl-ethylamino)-2-methyl-propionitrile, as a white solid, the characteristics of which are:

Mass spectrum (method A), ES+/−: [M+H]+: m/z 259; [M−H+ HCO$_2$H]−: m/z 303; Rt (min)=0.86

$[\alpha]_D^{25}$ at 589 nm=−89.0+/−1.4 (c=2.444 mg/0.5 mL CHCl$_3$)

$[\alpha]_D^{25}$ at 589 nm=−77.6+/−1.4 (c=1.818 mg/0.5 mL DMSO)

(2R,2S)-2-methyl-4-(R)-phenyl-2-(trifluoromethyl)-oxazolidine may be prepared in the following way.

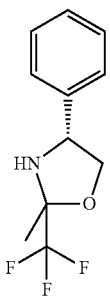

In a three-neck flask surmounted with a Dean-Stark, on a solution of 5 g of trifluoroacetone in 180 mL of toluene, are added 4.8 g of (R)-phenylglycinol and then in one go, 0.8 g of pyridinium para-toluene sulfonate acid. The obtained mixture is then heated with reflux for 18 hours during which 0.3 mL of water are collected. After cooling, the reaction mixture is concentrated under reduced pressure. The obtained residue is purified by filtration on silica (eluent: dichloromethane) in order to obtain 5.3 g of (2R,2S)-2-methyl-4-(R)-phenyl-2-(trifluoromethyl)-oxazolidine, as a colorless liquid, including the following characteristics:

Mass spectrum (method A), ES+/−: [M+H]+: m/z 232; Rt (min)=0.96

$[\alpha]_D^{25}$ at 589 nm=−23.4+/−0.8 (c=1.794 mg/0.5 mL MeOH)

Example 2a (2S)-1-Cyclopropyl-2-methyl-7-(morpholin-4-yl)-2-(trifluoromethyl)-2,3-dihydroimidazo[1,2-a]pyrimidin-5(1H)-one

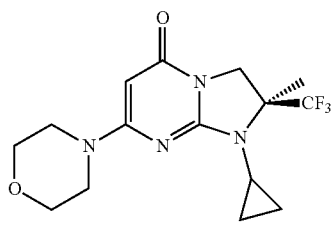 [SMILES: C[C@@]1(C(F)(F)F)Cn2c(nc(N3CCOCC3)cc2=O)N1C1CC1]

A suspension of 500 mg (1.643 mmol) of (2S)-2-methyl-7-(morpholin-4-yl)-2-(trifluoromethyl)-2,3-dihydroimidazo[1,2-a]pyrimidin-5(1H)-one, 795 mg (6.572 mmol) of bromocyclopropane and 3.480 g (4.271 mmol) of cesium carbonate in 10 cm³ of DMF is heated in a microwave oven to 160° C. for 1 h 30 mins and then to 190° C. for 1 h30. The reaction medium is diluted with 150 cm³ of ethyl acetate and then the organic phase is washed with twice 10 cm³ of distilled water and twice 15 cm³ of an aqueous solution saturated with sodium chloride, dried on anhydrous magnesium sulfate, filtered and dry concentrated under reduced pressure (2.7 kPa). The obtained crude is purified by flash chromatography on silica [eluent: dichloromethane/isopropanol/acetonitrile (85/7.5/7.5 by volume)]. The mixture obtained after evaporation of the fractions under reduced pressure is purified by preparative LCMS under the following conditions:

C18 SunFire (Waters) column—30×100.5 µm

Acetonitrile gradient (+0.07% TFA) in water (+0.07% TFA):

T0: 60% water (+0.07% TFA) and 40% acetonitrile (+0.07% TFA)

T2: 60% water (+0.07% TFA) and 40% acetonitrile (+0.07% TFA)

T11: 20% water (+0.07% TFA) and 80% acetonitrile (+0.07% TFA)

T11.5: 5% water (+0.07% TFA) and 95% acetonitrile (+0.07% TFA)

T15: 5% water (+0.07% TFA) and 95% acetonitrile (+0.07% TFA)

T15.5: 95% water (+0.07% TFA) and 5% acetonitrile (+0.07% TFA)

T19: 95% water (+0.07% TFA) and 5% acetonitrile (+0.07% TFA)

Flow rate: 30 mL/min

ESP+: 150-1300__15 min

Detection: UV 210 at 400 nm (diode array)

After evaporation of the fractions under reduced pressure, 5 mg of (2S)-1-cyclopropyl-2-methyl-7-(morpholin-4-yl)-2-(trifluoromethyl)-2,3-dihydroimidazo[1,2-a]-pyrimidin-5 (1H)-one are obtained as a brown solid including the following characteristics:

Mass spectrum (method A): ES+/−: [M+H]+: m/z 345

¹H NMR spectrum (400 MHz, δ in ppm, DMSO-d6): 0.76-0.97 (m, 4H); 1.66 (s, 3H); 2.42 (m, 1H); 3.43 (m, 4H); 3.62 (m partly hidden, 4H); 3.79 (d broad, J=12.7 Hz, 1H); 4.09 (d, J=12.7 Hz, 1H); 4.89 (s, 1H).

(2S)-2-methyl-7-(morpholin-4-yl)-2-(trifluoromethyl)-2,3-dihydroimidazo[1,2-a]pyrimidin-5(1H)-one may be prepared as described in Example 1a.

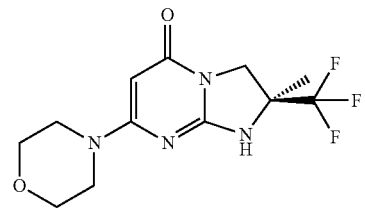 [SMILES: C[C@@]1(C(F)(F)F)Cn2c(nc(N3CCOCC3)cc2=O)N1]

Example 3a (2S)-1-Cyclopentyl-2-methyl-7-(morpholin-4-yl)-2-(trifluoromethyl)-2,3-dihydroimidazo[1,2-a]pyrimidin-5(1H)-one

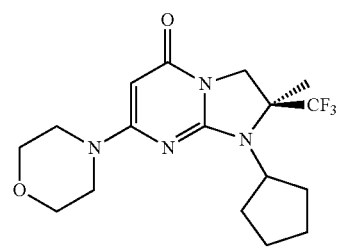 [SMILES: C[C@@]1(C(F)(F)F)Cn2c(nc(N3CCOCC3)cc2=O)N1C1CCCC1]

A suspension 200 mg (0.657 mmol) of (2S)-2-methyl-7-(morpholin-4-yl)-2-(trifluoromethyl)-2,3-dihydroimidazo[1,2-a]pyrimidin-5(1H)-one, 490 mg (3.285 mmol) of bromocyclopentane and 1.392 g (4.271 mmol) of cesium carbonate in 4 cm³ of DMF is heated in the microwave oven to 180° C. for 1 h and then to 200° C. for 1 h. 783 mg (5.256 mmol) of bromocyclopentane are added and then the mixture is heated in the microwave oven to 170° C. for 4 h. The reaction medium is diluted with 150 cm³ of ethyl acetate and then the organic phase is washed twice with 10 cm³ of distilled water and 3 times with 10 cm³ of an aqueous solution saturated with sodium chloride, dried on anhydrous magnesium sulfate, filtered and dry concentrated under reduced pressure (2.7 kPa). The obtained crude is purified by flash chromatography on silica [eluent: dichloromethane/methanol/acetonitrile (88/6/6 by volume)]. The obtained product is purified by flash chromatography on silica [eluent: dichloromethane/isopropanol/acetonitrile (80/10/10 by volume)]. After evaporation of the fractions under reduced pressure, 112 mg of (2S)-1-cyclopentyl-2-methyl-7-(morpholin-4-yl)-2-(trifluoromethyl)-2,3-dihydroimidazo[1,2-a]pyrimidin-5(1H)-one are obtained as a yellowish solid including the following characteristics:

[α]$_D^{25}$ at 589 nm=−5 in DMSO; C=2.024 mg/mL

Mass spectrum (method A): ES+/−: [M+H]+: m/z 373

¹H NMR spectrum (400 MHz, δ in ppm, DMSO-d6): 1.45-1.59 (m, 2H); 1.64 (s, 3H); 1.66-1.84 (m, 4H); 2.11-2.36 (m, 2H); 3.39 (m, 4H); 3.62 (m, 4H); 3.79-3.92 (m, 2H); 4.08 (d, J=12.7 Hz, 1H); 4.85 (s, 1H).

(2S)-2-methyl-7-(morpholin-4-yl)-2-(trifluoromethyl)-2,3-dihydroimidazo[1,2-a]-pyrimidin-5(1H)-one may be prepared as described in Example 1a.

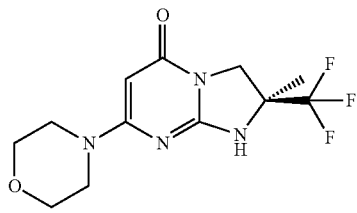 [SMILES: C[C@@]1(C(F)(F)F)Cn2c(nc(N3CCOCC3)cc2=O)N1]

Example 4a (S)-1-(2-Isopropoxy-ethyl)-2-methyl-7-(morpholin-4-yl)-2-(trifluoromethyl)-2,3-dihydroimidazo[1,2-a]pyrimidin-5(1H)-one

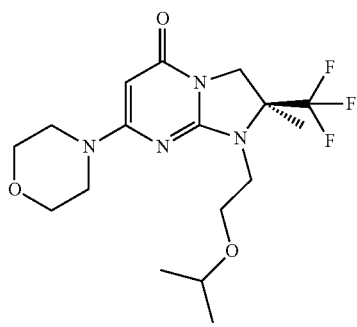 [SMILES: CC(C)OCCN1c2nc(N3CCOCC3)cc(=O)n2C[C@@]1(C)C(F)(F)F]

To 0.35 g (1.150 mmol) of (S)-2-methyl-7-(morpholin-4-yl)-2-(trifluoromethyl)-2,3-dihydroimidazo[1,2-a]pyrimidin-5(1H)-one, in suspension in 17 cm³ of acetonitrile, are added at a temperature close to 20° C., 0.386 g (1.495 mmol) of 2-isopropoxy-ethyl toluene-4-sulfonate and 0.487 g (1.495 mmol) of cesium carbonate. After 16 hours of stirring with reflux of acetonitrile, the reaction medium is dry concentrated under reduced pressure (2.7 kPa) and then diluted in 50 cm³ of dichloromethane and washed with 3 times 20 cm³ of distilled water and then with 20 cm³ of solution saturated with sodium chloride. The organic phase is dried on anhydrous magnesium sulfate, filtered and dry concentrated under reduced pressure (2.7 kPa) in order to obtain 0.29 g of a pale yellow oil which is purified by flash chromatography on silica [eluent: dichloromethane/methanol/acetonitrile (96/2/2 by volume)]. After concentration of the fractions under reduced pressure (2.7 kPa), a yellow oil is obtained which is triturated in 5 cm³ of pentane for 30 mins. After filtration of the solid, 0.169 g of (S)-1-(2-isopropoxy-ethyl)-2-methyl-7-(morpholin-4-yl)-2-(trifluoromethyl)-2,3-dihydroimidazo[1,2-a]pyrimidin-5(1H)-one are obtained as a white solid melting at 88° C. and including the following characteristics:

[α]$_D^{25}$ at 589 nm=+31.6 (c=0.39% g/100 mL in DMSO)

Mass spectrum (method A) ES+/−: [M+H]+: m/z 391. Rt (min)=0.85.

¹H NMR spectrum (400 MHz, δ in ppm, DMSO-d6): 1.06 (d, J=6.1 Hz, 3H); 1.07 (d, J=6.1 Hz, 3H); 1.63 (s, 3H); 3.36-3.68 (m, 12H); 0.88 (d broad, J=12.7 Hz, 1H); 4.12 (d, J=12.7 Hz, 1H); 4.87 (s, 1H).

(S)-2-methyl-7-(morpholin-4-yl)-2-(trifluoromethyl)-2,3-dihydroimidazo[1,2-a]-pyrimidin-5(1H)-one may be prepared as described in Example 1a.

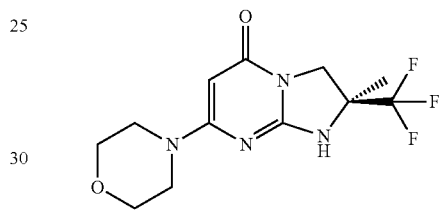

2-isopropoxy-ethyl toluene-4-sulfonate may be prepared as described in patent US2008/21032 A1.

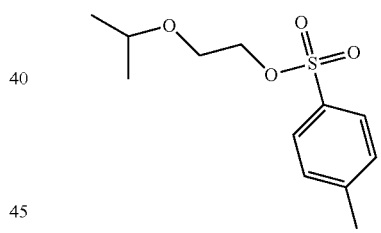

Example 5a (S)-1-(2-Hydroxy-2-methyl-propyl)-2-methyl-7-(morpholin-4-yl)-2-(trifluoromethyl)-2,3-dihydroimidazo[1,2-a]pyrimidin-5(1H)-one

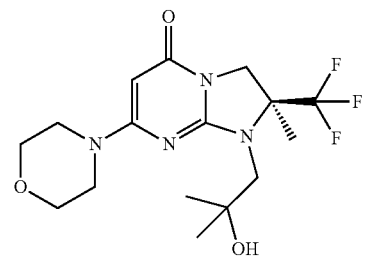 [SMILES: CC(C)(O)CN1c2nc(N3CCOCC3)cc(=O)n2C[C@@]1(C)C(F)(F)F]

To 0.500 g (1.643 mmol) of (S)-2-methyl-7-(morpholin-4-yl)-2-(trifluoromethyl)-2,3-dihydroimidazo[1,2-a]pyrimidin-5(1H)-one, in solution in 15 cm³ of acetonitrile, are added at a temperature close to 20° C., 1.185 g (16.43 mmol) of isobutylene oxide and 0.535 g (16.43 mmol) of cesium carbonate. After 1 hour of stirring at 120° C. and 1 hour 30 mins at 130° C. in a microwave appliance, the reaction medium is dry concentrated under reduced pressure (2.7 kPa) and then diluted in 30 cm³ of ethyl acetate and then washed with twice 20 cm³ of distilled water and 30 cm³ of solution saturated with sodium chloride. The organic phase is dried on anhydrous magnesium sulfate, filtered and dry concentrated under reduced pressure (2.7 kPa) in order to obtain a pale yellow oil which is purified by flash chromatography on silica [eluent: dichloromethane/methanol/acetonitrile (94/3/3 by volume)]. After concentration of the fractions under reduced pressure (2.7 kPa), 500 mg of (S)-1-(2-hydroxy-2-methyl-propyl)-2-methyl-7-(morpholin-4-yl)-2-(trifluoro-methyl)-2,3-dihydroimidazo[1,2-a]pyrimidin-5(1H)-one are obtained as a white solid melting at 72° C. and including the following characteristics:

[α]$_D^{25}$ at 589 nm=+55.5 (c=2.380 mg/0.5 mL DMSO)

Mass spectrum (method A) ES+/−: [M+H]+: m/z 377. Rt (min)=0.65.

¹H NMR spectrum (400 MHz, δ in ppm, DMSO-d6): 1.11 (s, 3H); 1.16 (s, 3H); 1.68 (s, 3H); 3.17 (d, J=15.0 Hz, 1H); 3.33-3.46 (m, 4H); 3.54-3.66 (m, 5H); 3.88 (d broad, J=12.7 Hz, 1H); 4.17 (d, J=12.7 Hz, 1H); 4.82 (s, 1H); 4.88 (s, 1H).

(S)-2-Methyl-7-(morpholin-4-yl)-2-(trifluoromethyl)-2,3-dihydroimidazo[1,2-a]-pyrimidin-5(1H)-one may be prepared as described in Example 1a.

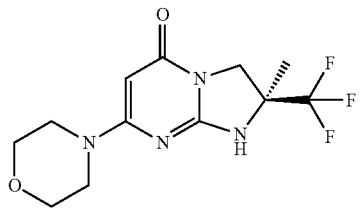 [SMILES: C[C@@]1(C(F)(F)F)Cn2c(nc(N3CCOCC3)cc2=O)N1]

Example 6a (S)-1-(2-Methoxy-2-methyl-propyl)-2-methyl-7-(morpholin-4-yl)-2-(trifluoromethyl)-2,3-dihydroimidazo[1,2-a]pyrimidin-5(1H)-one

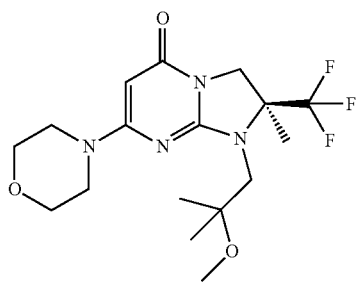 [SMILES: COC(C)(C)CN1c2nc(N3CCOCC3)cc(=O)n2C[C@@]1(C)C(F)(F)F]

To 0.500 g (1.328 mmol) of (S)-1-(2-hydroxy-2-methyl-propyl)-2-methyl-7-(morpholin-4-yl)-2-(trifluoromethyl)-2,3-dihydroimidazo[1,2-a]pyrimidin-5(1H)-one, suspended in 45 cm³ of tetrahydrofurane, are added at a temperature close to 20° C., 58.4 mg (1.461 mmol) of 60% sodium hydride in oil and 91 μl (1.461 mmol) of iodomethane. After 16 hours of stirring at 50° C., are added 372 mg (9.296 mmol) 60% sodium hydride in oil, 661 μl (10.62 mmol) of iodomethane and 2 cm³ of dimethylformamide. After 16 hours of stirring at 50° C., 10 cm³ of distilled water are added. The reaction medium is dry concentrated under reduced pressure (2.7 kPa) and then diluted in 70 cm³ of dichloromethane and washed with 3 times 30 cm³ of distilled water and then with 30 cm³ of the solution saturated with sodium chloride. The organic phase is dried on anhydrous magnesium sulfate, filtered and dry concentrated under reduced pressure (2.7 kPa) in order to obtain 317 mg of a beige solid which is purified by flash chromatography on silica [eluent: dichloromethane/methanol/acetonitrile (98/1/1 by volume)]. After concentration of the fractions under reduced pressure (2.7 kPa), 240 mg of (S)-1-(2-methoxy-2-methyl-propyl)-2-methyl-7-(morpholin-4-yl)-2-(trifluoromethyl)-2,3-dihydro-imidazo[1,2-a]pyrimidin-5(1H)-one, are obtained as a white solid melting between 56 and 60° C. and including the following characteristics:

[α]$_D^{25}$ at 589 nm=+55.5 (c=0.4% g/100 mL in DMSO)

Mass spectrum (method A) ES+/−: [M+H]+: m/z 391. Rt (min)=0.84.

¹H NMR spectrum (400 MHz, δ in ppm, DMSO-d6): 1.12 (s, 3H); 1.15 (s, 3H); 1.63 (s, 3H); 3.11 (s, 3H); 3.24 (d, J=15.2 Hz, 1H); 3.33-3.49 (m, 4H); 3.59-3.63 (m, 4H); 3.67 (d, J=15.2 Hz, 1H); 3.88 (d broad, J=12.7 Hz, 1H); 4.16 (d, J=12.7 Hz, 1H); 4.87 (s, 1H).

(S)-1-(2-hydroxy-2-methyl-propyl)-2-methyl-7-(morpholin-4-yl)-2-(trifluoromethyl)-2,3-dihydroimidazo[1,2-a]pyrimidin-5(1H)-one may be prepared as described in Example 5a.

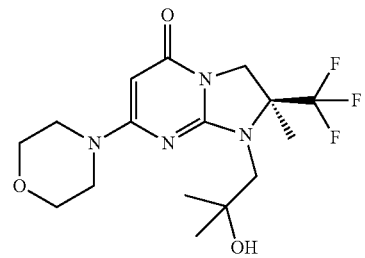 [SMILES: CC(C)(O)CN1c2nc(N3CCOCC3)cc(=O)n2C[C@@]1(C)C(F)(F)F]

Example 7a 1-(2-Isopropoxyethyl)-2,2-dimethyl-7-(morpholin-4-yl)-2,3-dihydroimidazo[1,2-a]pyrimidin-5(1H)-one

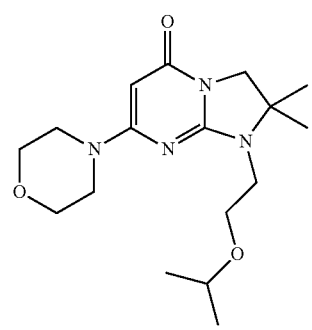 [SMILES: CC(C)OCCN1c2nc(N3CCOCC3)cc(=O)n2CC1(C)C]

150 mg of 7-chloro-1-(2-isopropoxyethyl)-2,2-dimethyl-2,3-dihydroimidazo[1,2-a]pyrimidin-5(1H)-one in 2 mL of morpholine are heated with the microwave oven to 80° C. for 45 mins. The crude is purified by flash chromatography on silica gel (CH$_2$Cl$_2$ 100% to CH$_2$Cl$_2$/MeOH, 92/8). 0.085 g (yield=60%) of 1-(2-isopropoxyethyl)-2,2-dimethyl-7-(morpholin-4-yl)-2,3-dihydroimidazo[1,2-a]pyrimidin-5(1H)-one are obtained as a beige solid and including the following characteristics:

Mass spectrum (method A) ES+/−: Rt: 1.31 min, M/Z=337

$^1$H NMR spectrum (250 MHz, δ in ppm, DMSO-d6): 1.07 (d, 6H), 1.28 (s, 6H), 3.27-3.35 (m, 1H), 3.38 (t, 4H), 3.47-3.65 (m, 10H), 4.78 (s, 1H).

7-chloro-1-(2-isopropoxyethyl)-2,2-dimethyl-2,3-dihydroimidazo[1,2-a]pyrimidin-5(1H)-one may be prepared in the following way.

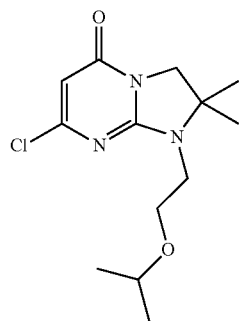 [SMILES: CC(C)OCCN1c2nc(Cl)cc(=O)n2CC1(C)C]

To 0.200 g of 7-chloro-2,2-dimethyl-2,3-dihydroimidazo[1,2-a]pyrimidin-5(1H)-one suspended in 7 mL of CH$_3$CN, 0.65 g of cesium carbonate and 0.51 g of 2-isopropoxyethyl 4-methylbenzenesulfonate are added. The mixture is heated to 65° C. for 36 h. Water, ethyl acetate are added and then after decantation, the organic phase is dried with magnesium sulfate and then evaporated. The crude is purified by flash chromatography on silica gel (CH$_2$Cl$_2$/MeOH, 99/1). 0.17 g (yield=45%) of 7-chloro-1-(2-isopropoxyethyl)-2,2-dimethyl-2,3-dihydroimidazo[1,2-a]pyrimidin-5(1H)-one are obtained as a brown powder.

2-isopropoxy-ethyl toluene-4-sulfonate may be prepared as described in patent US2008/21032 A1.

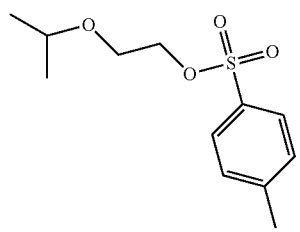 [SMILES: Cc1ccc(S(=O)(=O)OCCOC(C)C)cc1]

7-chloro-2,2-dimethyl-2,3-dihydroimidazo[1,2-a]pyrimidin-5(1H)-one may be prepared in the following way.

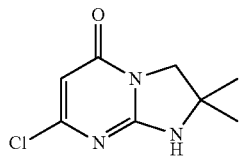

18.5 g of 7-hydroxy-2,2-dimethyl-2,3-dihydroimidazo[1,2-a]pyrimidin-5(1H)-one are suspended in 200 mL of dichloroethane. 48 mL of POCl$_3$ are added and the mixture is heated to 60° C. for 3 h. After returning to RT, the solvents are dry evaporated. The residue is taken up in water and AcOEt, 30% NaOH is added until pH=12. The product precipitates, it is filtered and then dried. 16.9 g (yield=83%) of 7-chloro-2,2-dimethyl-2,3-dihydroimidazo[1,2-a]pyrimidin-5(1H)-one are obtained as a yellow solid and including the following characteristics:

Mass spectrum (method A) LC/MS: Rt: 1.92 min, M/Z=200

7-hydroxy-2,2-dimethyl-2,3-dihydroimidazo[1,2-a]pyrimidin-5(1H)-one may be prepared in the following way.

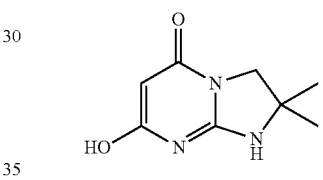

To 250 mL of methanol under nitrogen, 5.21 g of sodium are added. Once dissolution is total and after returning to RT, 20 g of 5,5-dimethyl-4,5-dihydro-imidazol-2-amine bromide and 31.2 g of ethyl malonate are added. The medium is heated with reflux for 16 h. The reaction medium is dry concentrated, and then taken up in 40 mL of ice water. The expected product is precipitated by adding 1N HCl. The obtained precipitate is filtered, washed with water and then dried in the oven at 50° C. 18.62 g (yield=97%) of 7-hydroxy-2,2-dimethyl-2,3-dihydroimidazo[1,2-a]pyrimidin-5(1H)-one are obtained as a white solid.

5,5-dimethyl-4,5-dihydro-imidazol-2-amine bromide may be prepared in the following way.

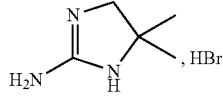

25 g of 2-methylpropane-1,2-diamine are solubilized in 250 mL of water. The medium is cooled to 0° C. and then 33.7 g of cyanogen bromide are added in fractions. The reaction medium is left to return to RT and is left with stirring for 3 hours. The medium is dry concentrated. The obtained oil is taken up in 25 mL of ethanol, 300 mL of ether are added. The product precipitates. Filtration and then drying is performed.

55.78 g (yield=99%) of 5,5-dimethyl-4,5-dihydro-imidazol-2-amine are obtained as a white powder.

Example 8a

1'-(2-Methoxyethyl)-7'-morpholin-4-ylspiro[cyclopentane-1,2'-imidazo[1,2-a]pyrimidin]-5'-one

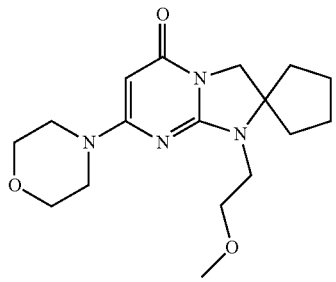 [SMILES: COCCN1c2nc(N3CCOCC3)cc(=O)n2CC12CCCC2]

150 mg of 7'-chloro-1'-(2-methoxyethyl)spiro[cyclopentane-1,2'-imidazo[1,2-a]pyrimidin]-5'-one in 2 mL of morpholine are heated in the microwave oven to 80° C. for 45 mins. The crude is purified by flash chromatography on silica gel (CH$_2$Cl$_2$ 100% a CH$_2$Cl$_2$/MeOH, 92/8). 0.070 g (yield=52%) of 1-(2-methoxyethyl)-7'-morpholin-4-ylspiro[cyclopentane-1,2'-imidazo[1,2-a]pyrimidin]-5'-one are obtained as a white solid and including the following characteristics:

Mass spectrum (method A) ES+/−: Rt: 1.48 min, M/Z=335.

$^1$H NMR spectrum (400 MHz, δ in ppm, DMSO-d6): 1.48-1.97 (m, 8H), 3.27 (s, 3H), 3.32-3.42 (m, 6H), 3.51 (t, 2H), 3.61 (t, 4H), 3.69 (s, 2H), 4.78 (s, 1H)

7'-chloro-1'-(2-methoxyethyl)spiro[cyclopentane-1,2'-imidazo[1,2-a]pyrimidin]-5'-one may be prepared in the following way.

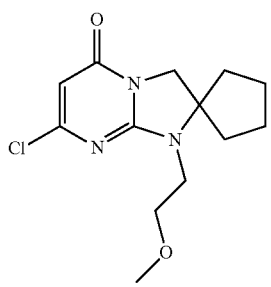 [SMILES: COCCN1c2nc(Cl)cc(=O)n2CC12CCCC2]

0.200 g of 7'-chlorospiro[cyclopentane-1,2'-imidazo[1,2-a]pyrimidin]-5'-one are suspended in 7 mL de CH$_3$CN, 0.62 g of cesium carbonate and 0.49 g of 2-methoxyethyl 4-methylbenzenesulfonate are added. The mixture is heated to 65° C. for 36 h. Water, ethyl acetate are added and then after decantation the organic phase is dried with magnesium sulfate and then evaporated. The crude is purified by flash chromatography on silica gel (CH$_2$CL$_2$/MeOH, 99/1). 0.16 g (yield=41%) of 7'-chloro-1'-(2-methoxyethyl)-spiro[cyclopentane-1,2'-imidazo[1,2-a]pyrimidin]-5'-one are obtained as a brown powder and including the following characteristics:

Mass spectrum (method A) ES+/−: Rt: 2.31 min, M/Z=284

2-methoxyethyl 4-methylbenzenesulfonate may be prepared as described in <<the patent US2008/21032 A1.>>

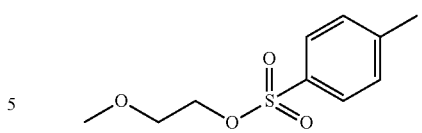

7'-chlorospiro[cyclopentane-1,2'-imidazo[1,2-a]pyrimidin]-5'-one may be prepared in the following way.

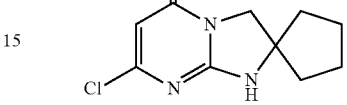

3.935 g of 7'-hydroxyspiro[cyclopentane-1,2'-imidazo[1,2-a]pyrimidin]-5'-one are suspended in 60 mL de 1,2-dichloroethane. 8.78 mL of POCl$_3$ are added and then the medium is heated to 65° C. for 2H. The medium is dry concentrated. The residue is taken up in 80 mL of EtOAc and 10 mL of H$_2$O and then cooled in an ice bath. Concentrated NaOH is added until pH 7. The aqueous phase is extracted with EtOAc, and then the organic phase is dried on magnesium sulfate. After evaporation of the solvent, 1.8 g (yield=42%) of 7'-chlorospiro[cyclopentane-1,2'-imidazo[1,2-a]pyrimidin]-5'-one are obtained as a brown solid and including the following characteristics:

Mass spectrum (method A) ES+/−: Rt: 1.97 min, M/Z=226

7'-hydroxyspiro[cyclopentane-1,2'-imidazo[1,2-a]pyrimidin]-5'-one may be prepared in the following way.

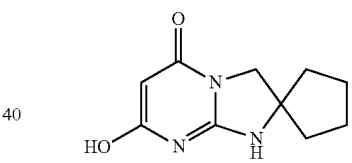

2.37 g of sodium are added in a fractionated way to 10 mL of MeOH. After total dissolution, 5.68 g of 1,3-diazaspiro[4.4]non-2-en-2-amine solubilized beforehand in 5 mL of MeOH, and then 25.38 mL of ethyl malonate are added. The mixture is heated to 100° C., after 4 h of heating, the medium is dry concentrated. The oil obtained is taken up in ether. The precipitate is filtered and the residue is then taken up in 10 mL of H$_2$O and acidified with conc. HCl until pH 3-4. The formed precipitate is filtered, washed with ether and dried in the oven in vacuo. 3.97 g (yield=74%) of 7'-hydroxyspiro[cyclopentane-1,2'-imidazo[1,2-a]pyrimidin]-5'-one are obtained as a beige solid.

1,3-diazaspiro[4.4]non-2-en-2-amine may be prepared in the following way.

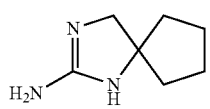

3.35 g of 1-(aminomethyl)cyclopentanamine are solubilized in 20 mL of water, cooled beforehand in an ice bath. 3.52 g of BrCN are added and the mixture is then stirred for 3 h at RT. The solvent is evaporated. 5.67 g (yield=88%) of 1,3-diazaspiro[4.4]non-2-en-2-amine are obtained as a brown oil.

1-(aminomethyl)cyclopentanamine may be prepared in the following way.

14.1 g of 1-(aminomethyl)-N-benzylcyclopentanamine are solubilized in 28 mL of acetic acid and 80 mL of methanol. 3.67 g of 5% palladium on coal are added and then the mixture is placed in a can to be hydrogenated under 7 bars of hydrogen at 30° C. The reaction mixture is stirred at 30° C. for 24 h. After filtration on Celite, the medium is concentrated, and the obtained oil is then taken up in 5 mL of $H_2O$ and 180 mL of $Et_2O$. The aqueous phase is basified by adding concentrated NaOH dropwise. The aqueous phase is extracted with $Et_2O$. The organic phases are dried on magnesium sulfate and then concentrated. 3.57 g (yield=76%) of 1-(aminomethyl)cyclopentanamine are obtained as a yellow oil.

1-(aminomethyl)-N-benzylcyclopentanamine may be prepared in the following way.

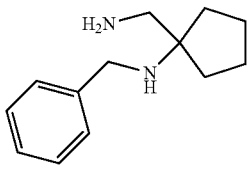 [SMILES: NCC1(NCc2ccccc2)CCCC1]

14.1 g of 1-(benzylamino)cyclopentanecarbonitrile are solubilized in 300 mL of $Et_2O$. The mixture is cooled and then 10.68 g of $LiAlH_4$ are added in fractions, while maintaining the temperature in T° C. to −5° C.-0° C. Stirring is applied and under nitrogen at 0° C. for 1 h. After return to RT, 11 mL $H_2O$ and then 11 mL of 15% KOH and finally 33 mL of $H_2O$ are added dropwise while maintaining the temperature less than 15° C. The precipitate is filtered on Celite, and then the organic phase is dried on magnesium sulfate. The solvents are dry evaporated. 14.23 g (yield=99%) of 1-(aminomethyl)-N-benzylcyclopentanamine are obtained as a yellowish oil.

1-(benzylamino)cyclopentanecarbonitrile may be prepared in the following way

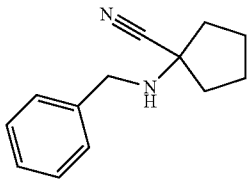 [SMILES: N#CC1(NCc2ccccc2)CCCC1]

7 g of cyclopentanone are solubilized in 10 mL of benzylamine. The reaction mixture is stirred for 30 mins under argon and at RT. 12.75 mL of TMSCN are added dropwise and then stirred for 1 h. They are dry evaporated. They are purified by flash chromatography on silica gel (heptane/EtOAc 99:1, to heptane/EtOAc 65:35). 14.15 g (yield=85%) of 1-(benzylamino)cyclopentanecarbonitrile are obtained as a colorless oil.

Example 9a

1'-(2-isopropoxyethyl)-7'-morpholin-4-ylspiro[cyclopentane-1,2'-imidazo[1,2-a]pyrimidin]-5'-one

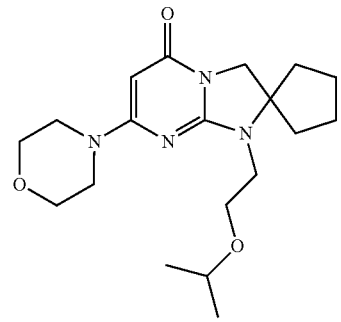 [SMILES: CC(C)OCCN1c2nc(N3CCOCC3)cc(=O)n2CC12CCCC2]

150 mg of 7'-chloro-1-(2-isopropoxyethyl)spiro[cyclopentane-1,2'-imidazo[1,2-a]pyrimidin]-5'-one in 2 mL of morpholine are heated in the microwave oven to 80° C. for 45 mins. The crude is purified by flash chromatography on silica gel ($CH_2Cl_2$ 100% to $CH_2Cl_2$/MeOH, 92/8). 0.085 g (yield=61%) of 1-(2-isopropoxyethyl)-7'-morpholin-4-ylspiro[cyclopentane-1,2'-imidazo[1,2-a]pyrimidin]-5'-one are obtained as a white solid including the following characteristics:

Mass spectrum (method A) ES+/−: Rt: 1.25 min, M/Z=363.
$^1$H NMR spectrum (400 MHz, δ in ppm, DMSO-d6): 1.07 (d, 6H), 1.51-1.77 (m, 6H), 1.79-1.97 (m, 2H), 3.31 (m, 1H), 3.39 (t, 4H), 3.48-3.64 (m, 8H), 3.69 (s, 2H), 4.77 (s, 1H).

7'-chloro-1'-(2-isopropoxyethyl)spiro[cyclopentane-1,2'-imidazo[1,2-a]pyrimidin]-5'-one may be prepared in the following way.

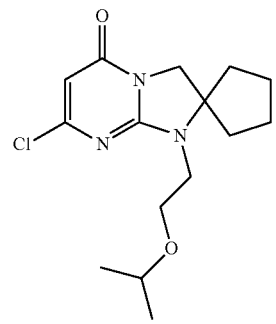 [SMILES: CC(C)OCCN1c2nc(Cl)cc(=O)n2CC12CCCC2]

0.200 g of 7'-chlorospiro[cyclopentane-1,2'-imidazo[1,2-a]pyrimidin]-5'-one are suspended in 7 mL of $CH_3CN$, 0.70 g of cesium carbonate and 0.55 g of 2-isopropoxyethyl 4-methylbenzenesulfonate are added. The mixture is heated to 65° C. for 36 h. Water, ethyl acetate are added and then after decantation, the organic phase is dried with magnesium sulfate and then evaporated. The crude is purified by flash chromatography on silica gel ($CH_2Cl_2$/MeOH, 99/1). 0.17 g (yield=47%) of 7'-chloro-1'-(2-isopropoxyethyl)-spiro[cyclopentane-1,2'-imidazo[1,2-a]pyrimidin]-5'-one are obtained as a brown powder and including the following characteristics:

Mass spectrum (method A) ES+/−: Rt: 2.59 min, M/Z=312

2-isopropoxy-ethyl toluene-4-sulfonate may be prepared as described in patent US2008/21032 A1.

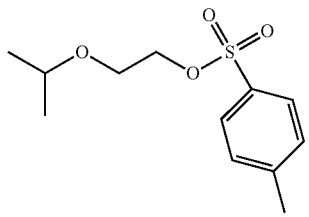 [SMILES: Cc1ccc(S(=O)(=O)OCCOC(C)C)cc1]

7'-chlorospiro[cyclopentane-1,2'-imidazo[1,2-a]pyrimidin]-5'-one may be prepared as described in Example 8a.

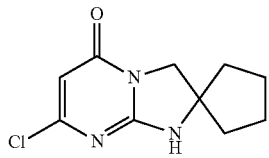 [SMILES: O=c1cc(Cl)nc2n1CC1(CCCC1)N2]

Example 10a

Pharmaceutical Composition

Tablets were prepared, with the following formulation:

| | |
|---|---|
| Product of Example 2a | 0.2 g |
| Excipient for a finished tablet at (detail of the excipient: lactose, talcum, starch, magnesium stearate). | 1 g |

Example 2a is taken as an example of a pharmaceutical preparation, this preparation may be made if desired with other products as examples in the present application.

Example 1b (8S)-9-(2-Ethylbutyl)-2-(morpholin-4-yl)-8-(trifluoromethyl)-6,7,8,9-tetrahydro-4H-pyrimido[1,2-a]pyrimidin-4-one

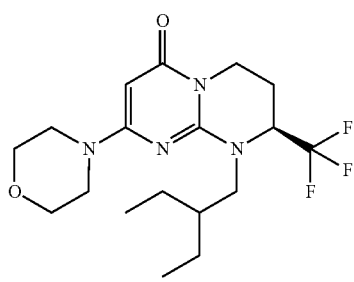 [SMILES: CCC(CC)CN1c2nc(N3CCOCC3)cc(=O)n2CC[C@H]1C(F)(F)F]

A suspension of 200 mg (0.657 mmol) of (8S)-2-(morpholin-4-yl)-8-(trifluoromethyl)-6,7,8,9-tetrahydro-4H-pyrimido[1,2-a]pyrimidin-4-one, 542 mg (3.285 mmol) of 3-(bromomethyl)pentane and 1.392 g (4.271 mmol) of cesium carbonate in 5 cm³ of acetonitrile is heated in the microwave oven to 180° C. for 1 h 30 mins. The reaction medium is diluted with 100 cm³ of ethyl acetate and then the organic phase is washed with twice 10 cm³ of distilled water and twice 10 cm³ of an aqueous solution saturated with sodium chloride, dried on anhydrous magnesium sulfate, filtered and dry concentrated under reduced pressure (2.7 kPa). The obtained crude is purified by flash chromatography on silica [eluent: dichloromethane/methanol/acetonitrile (90/5/5 by volume)]. After evaporation of the fractions under reduced pressure, the obtained mixture is purified by HPLC under the following conditions:

Apparatus: Hipersep from Novasep

Chiral stationary phase: Whelk01 SS 10 μm mixed batch 7.5×40 cm from Regis

Mobile phase: 0.1% $Et_3N$ in a 80% heptane and 20% EtOH mixture

Flow rate: 300 mL/min

Detection: UV 254 nm

After evaporation of the fractions under reduced pressure, 86 mg of (8S)-9-(2-ethylbutyl)-2-(morpholin-4-yl)-8-(trifluoromethyl)-6,7,8,9-tetrahydro-4H-pyrimido[1,2-a]pyrimidin-4-one are obtained as a white solid, including the following characteristics:

Mass spectrum (method A): ES+/−: [M+H]+: m/z 389

$^1$H NMR spectrum (400 MHz, δ in ppm, DMSO-d6): 0.83 (m, 6H); 1.12-1.37 (m, 4H); 1.85 (m, 1H); 2.15 (m, 1H); 2.36 (m, 1H); 2.89 (dd, J=7.9 and 13.5 Hz, 1H); 3.23 (m, 1H); 3.39 (m, 4H); 3.60 (m, 4H); 4.11 (m, 1H); 4.19 (dd, J=6.8 and 13.5 Hz, 1H); 4.52 (m, 1H); 4.96 (s, 1H).

(8S)-2-(morpholin-4-yl)-8-(trifluoromethyl)-6,7,8,9-tetrahydro-4H-pyrimido[1,2-a]pyrimidin-4-one may be prepared in the following way.

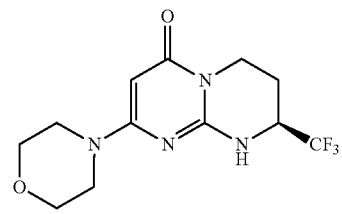 [SMILES: O=c1cc(N2CCOCC2)nc2n1CC[C@@H](C(F)(F)F)N2]

A mixture of 1 g of (8S)-2-chloro-8-(trifluoromethyl)-6,7,8,9-tetrahydro-4H-pyrimido[1,2-a]pyrimidin-4-one and of 15 mL of morpholine is heated to 80° C. After one hour and a half of heating and after monitoring with LC/MS, the reaction is completed. After cooling, the reaction mixture is concentrated under reduced pressure. On the obtained residue, 10 mL of cold water and 100 mL of ethyl acetate are added. The resulting organic phase is separated and then dried on magnesium sulfate, filtered and concentrated under reduced pressure in order to obtain 1.2 g of (8S)-2-(morpholin-4-yl)-8-(trifluoromethyl)-6,7,8,9-tetrahydro-4H-pyrimido[1,2-a]pyrimidin-4-one including the following characteristics:

Mass spectrum (method A), ES+/−: [M+H]+: m/z 305; [M−H]−: m/z 303; Rt (min)=0.49

$[\alpha]_D^{25}$ at 589 nm=+14.2+/−0.6 (c=2.25 mg/0.5 mL MeOH)

(8S)-2-chloro-8-(trifluoromethyl)-6,7,8,9-tetrahydro-4H-pyrimido[1,2-a]pyrimidin-4-one may be prepared in the following way.

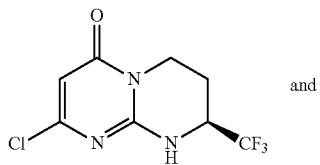 and

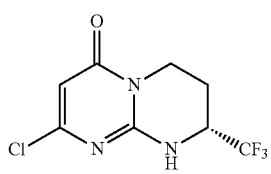

The separation of both enantiomers of (8R,8S)-2-chloro-8-(trifluoromethyl)-6,7,8,9-tetrahydro-4H-pyrimido[1,2-a]pyrimidin-4-one (17 g) is carried out by chiral chromatography: stationary phase: Chiralpak AD; mobile phase: EtOH (20%)/heptane (80%). The levo-rotatory enantiomer is concentrated in order to obtain 8.52 g of (R)-2-chloro-8-(trifluoromethyl)-6,7,8,9-tetrahydro-4H-pyrimido[1,2-a]pyrimidin-4-one, as a white powder. The dextro-rotatory enantiomer is concentrated in order to obtain 8.21 g of (8S)-2-chloro-8-(trifluoromethyl)-6,7,8,9-tetrahydro-4H-pyrimido[1,2-a]pyrimidin-4-one, as a white powder, including the following characteristics:

Mass spectrum (method A), ES+/−: [M+H]$^+$: m/z 254; [M−H]$^-$: m/z 252; Rt (min)=0.51

$[\alpha]_D^{25}$ at 589 nm=+21.3+/−0.5 (MeOH)

(8R,8S)-2-chloro-8-(trifluoromethyl)-6,7,8,9-tetrahydro-4H-pyrimido[1,2-a]pyrimidin-4-one may be prepared in the following way.

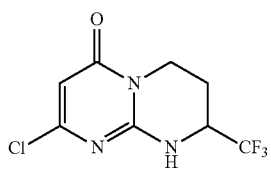 [SMILES: O=c1cc(Cl)nc2n1CCC(C(F)(F)F)N2]

To a suspension of 34 g of (8R,8S)-2-hydroxy-8-(trifluoromethyl)-6,7,8,9-tetrahydro-4H-pyrimido[1,2-a]pyrimidin-4-one in 500 mL of 1,2-dichloroethane, are added at room temperature and under an argon atmosphere, 60 mL of phosphorus oxychloride. The obtained mixture is then heated to 65° C. After three hours of stirring at 65° C., the reaction is completed according to monitoring with LC/MS. After cooling, the reaction mixture is dry evaporated under reduced pressure. The obtained residue is taken up with 100 mL of cold water and 400 mL of ethyl acetate. On the obtained mixture, 32% soda is added up to pH=6. The resulting organic phase is separated and then dried on magnesium sulfate, filtered and concentrated under reduced pressure in order to obtain an orange residue. This residue is purified by chromatography on silica (eluent: CH$_2$Cl$_2$/MeOH: 97/03) in order to obtain 20 g of (8R,8S)-2-chloro-8-(trifluoromethyl)-6,7,8,9-tetrahydro-4H-pyrimido[1,2-a]pyrimidin-4-one, as a white solid, including the following characteristics:

Mass spectrum (method A), ES+/−: [M+H]+: m/z 254; [M−H]−: m/z 252; Rt (min)=0.51

(8R,8S)-2-hydroxy-8-(trifluoromethyl)-6,7,8,9-tetrahydro-4H-pyrimido[1,2-a]-pyrimidin-4-one may be prepared in the following way.

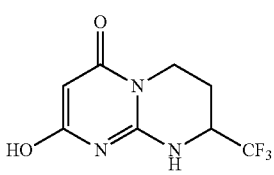 [SMILES: O=c1cc(O)nc2n1CCC(C(F)(F)F)N2]

On a mixture of 50 mL of diethyl malonate, are added 10 g of (4R,4S)-4-(trifluoromethyl)-1,4,5,6-tetrahydropyrimidin-2-ylamine hydrochloride and 10 g of sodium methylate. The obtained mixture is brought to 100° C. for 75 minutes. The heterogeneous mixture thickens and becomes yellow with slight gas evolvement. After cooling, the reaction mixture is dry evaporated under reduced pressure. The obtained residue is triturated with ethyl ether. The solid form is filtered on a frit and then is taken up with 20 mL of cold water. On the thick suspension obtained, 12N hydrochloric acid is added up to pH=5-6. The obtained suspension is filtered on a glass frit and the insoluble material is rinsed with ethyl ether in order to obtain 11.5 g of (8R,8S)-2-hydroxy-8-(trifluoromethyl)-6,7,8,9-tetrahydro-4H-pyrimido[1,2-a]pyrimidin-4-one, as a white solid, including the following characteristics:

Mass spectrum (method A), ES+/−: [M+H]+: m/z 236; [M−H]−: m/z 234; Rt (min)=0.26

(4R,4S)-4-(trifluoromethyl)-1,4,5,6-tetrahydropyrimidin-2-ylamine hydrochloride may be prepared in the following way.

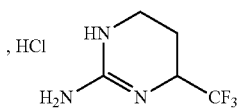

In an autoclave, under 3 bars at 22° C., for 24 hours, a mixture of 1.1 g of 10% Pd/C, of 22 g of 2-amino-4-(trifluoromethyl)pyrimidine dissolved in 200 mL of water, 50 mL of methanol and 50 mL of 12N HCl is hydrogenated. The resulting mixture is then filtered and the filtrate is concentrated under reduced pressure. The obtained residue is dried in an oven, in the presence of P$_2$O$_5$, in order to obtain 27 g of (4R,4S)-4-(trifluoromethyl)-1,4,5,6-tetrahydropyrimidin-2-ylamine hydrochloride, as a grey solid including the following characteristics:

Mass spectrum (method A), ES+/−: [M+H]+: m/z 168; Rt (min)=0.17

Example 2b (8S)-9-(Cyclopropylmethyl)-2-(morpholin-4-yl)-8-(trifluoromethyl)-6,7,8,9-tetrahydro-4H-pyrimido[1,2-a]pyrimidin-4-one

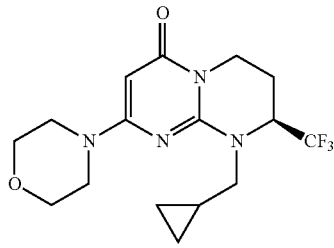 [SMILES: O=c1cc(N2CCOCC2)nc2n1CC[C@@H](C(F)(F)F)N2CC1CC1]

A suspension of 200 mg (0.657 mmol) of (8S)-2-(morpholin-4-yl)-8-(trifluoromethyl)-6,7,8,9-tetrahydro-4H-pyrimido[1,2-a]pyrimidin-4-one, 443 mg (3.285 mmol) of bromomethylcyclopropane and 1.392 g (4.271 mmol) of cesium carbonate in 5 cm³ of DMF is heated in the microwave oven to 170° C. for 1 h. The reaction medium is diluted with 150 cm³ of ethyl acetate and the organic phase is then washed twice with 10 cm³ of distilled water and twice 10 cm³ of an aqueous solution saturated with sodium chloride, dried on anhydrous magnesium sulfate, filtered and dry concentrated under reduced pressure (2.7 kPa). The obtained crude is purified by flash chromatography on silica [eluent: dichloromethane/methanol/acetonitrile (90/5/5 by volume)]. After evaporation of the fractions under reduced pressure, 178 mg of (8S)-9-(cyclopropylmethyl)-2-(morpholin-4-yl)-8-(trifluoromethyl)-6,7,8,9-tetrahydro-4H-pyrimido[1,2-a]pyrimidin-4-one are obtained as a pink solid including the following characteristics:

$[\alpha]_D^{25}$ at 589 nm=+47.6+/−1 in DMSO; C=4.30 mg/mL

Mass spectrum (method A): ES+/−: [M+H]+: m/z 359

¹H NMR spectrum (400 MHz, δ in ppm, DMSO-d6): 0.24 (m, 1H); 0.38-0.48 (m, 3H); 1.23 (m, 1H); 2.09 (m, 1H); 2.39 (m, 1H); 2.89 (m, 1H); 3.21 (m, 1H); 3.34-3.45 (m, 4H); 3.62 (m, 4H); 4.12-4.24 (m. 2H); 4.69 (m, 1H); 4.97 (s, 1H).

(8S)-2-(morpholin-4-yl)-8-(trifluoromethyl)-6,7,8,9-tetrahydro-4H-pyrimido[1,2-a]pyrimidin-4-one may be prepared as described in Example 1b.

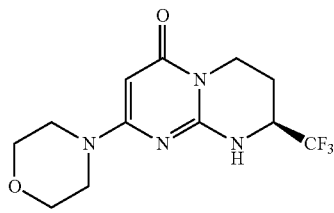 [SMILES: O=c1cc(N2CCOCC2)nc2n1CC[C@@H](C(F)(F)F)N2]

Example 3b (8S)-9-Cyclopentyl-2-(morpholin-4-yl)-8-(trifluoromethyl)-6,7,8,9-tetrahydro-4H-pyrimido[1,2-a]pyrimidin-4-one

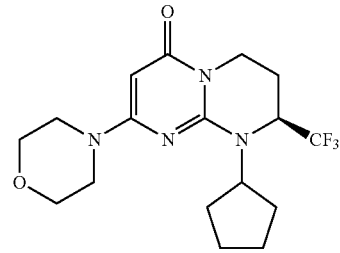 [SMILES: O=c1cc(N2CCOCC2)nc2n1CC[C@@H](C(F)(F)F)N2C1CCCC1]

A suspension of 200 mg (0.657 mmol) of (8S)-2-(morpholin-4-yl)-8-(trifluoromethyl)-6,7,8,9-tetrahydro-4H-pyrimido[1,2-a]pyrimidin-4-one, 490 mg (3.285 mmol) of bromocyclopropane and 1.392 g (4.271 mmol) of cesium carbonate in 4 cm³ of DMF is heated in the microwave oven to 185° C. for 1 h. The reaction medium is diluted with about 150 cm³ of ethyl acetate and the organic phase is then washed with twice 10 cm³ of distilled water and twice 15 cm³ of an aqueous solution saturated with sodium chloride, filtered and dry concentrated under reduced pressure (2.7 kPa). The obtained crude is purified by flash chromatography on silica [eluent: dichloromethane/propanol-1/acetonitrile (85/7.5/7.5 by volume)]. After evaporation of the fractions under reduced pressure, 97 mg of (8S)-9-cyclopentyl-2-(morpholin-4-yl)-8-(trifluoromethyl)-6,7,8,9-tetrahydro-4H-pyrimido[1,2-a]pyrimidin-4-one are obtained as a yellowish solid including the following characteristics:

$[\alpha]_D^{25}$ at 589 nm=−24 in DMSO; C=1.836 mg/mL

Mass spectrum (method A): ES+/−: [M+H]+: m/z 373

¹H NMR spectrum (400 MHz, δ in ppm, DMSO-d6): 1.45-1.95 (m, 8H); 2.00 (m, 1H); 2.37 (m, 1H); 3.22 (m, 1H); 3.40 (m, 4H); 3.62 (m, 4H); 4.04 (m, 1H); 4.52 (m, 1H); 4.70 (m, 1H); 4.98 (s, 1H).

(8S)-2-(morpholin-4-yl)-8-(trifluoromethyl)-6,7,8,9-tetrahydro-4H-pyrimido[1,2-a]-pyrimidin-4-one may be prepared as described in Example 1b.

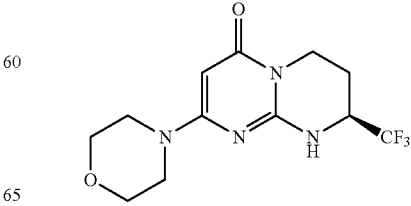

Example 4b (8S)-9-(2-Hydroxyethyl)-2-(morpholin-4-yl)-8-(trifluoromethyl)-6,7,8,9-tetrahydro-4H-pyrimido[1,2-a]pyrimidin-4-one

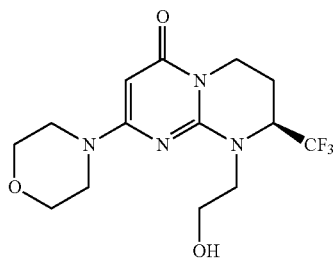 [SMILES: O=c1cc(N2CCOCC2)nc2n1CC[C@@H](C(F)(F)F)N2CCO]

A suspension of 200 mg (0.657 mmol) of (8S)-2-(morpholin-4-yl)-8-(trifluoromethyl)-6,7,8,9-tetrahydro-4H-pyrimido[1,2-a]pyrimidin-4-one, 565 mg (3.285 mmol) of 2-iodoethanol and 1.392 g (4.271 mmol) of cesium carbonate in 5 cm³ of acetonitrile is heated in a microwave oven to 150° C. for 1 h and then to 170° C. for 1 h. The reaction medium is diluted with dichloromethane and then filtered on a frit and the filtrate is dry evaporated under reduced pressure (2.7 kPa). The obtained crude is purified by flash chromatography on silica [eluent: dichloromethane/methanol/acetonitrile (86/7/7 by volume)]. After evaporation of the fractions under reduced pressure, 23 mg of (8S)-9-(2-hydroxyethyl)-2-(morpholin-4-yl)-8-(trifluoromethyl)-6,7,8,9-tetrahydro-4H-pyrimido[1,2-a]pyrimidin-4-one are obtained as an orange solid melting at 117° C. and including the following characteristics:

$[\alpha]_D^{25}$ at 589 nm=+44 in DMSO; C=1.501 mg/mL

Mass spectrum (method A): ES+/−: [M+H]+: m/z 349; [M−H+ HCO2H]−: m/z 393

¹H NMR spectrum (400 MHz, δ in ppm, DMSO-d6): 2.11 (m, 1H); 2.32 (m, 1H); 3.19 (m, 1H); 3.24-3.44 (m partly hidden, 5H); 3.50-3.78 (m, 6H); 4.09 (m, 1H); 4.18 (m, 1H); 4.61 (m, 1H); 4.79 (t broad, J=5.7 Hz, 1H); 4.97 (s, 1H).

(8S)-2-(morpholin-4-yl)-8-(trifluoromethyl)-6,7,8,9-tetrahydro-4H-pyrimido[1,2-a]-pyrimidin-4-one may be prepared as described in Example 1b.

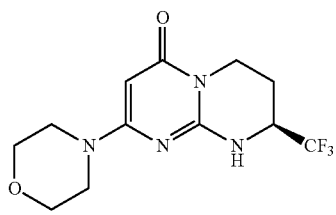 [SMILES: O=c1cc(N2CCOCC2)nc2n1CC[C@@H](C(F)(F)F)N2]

Example 5b (S)-9-(2-Isopropoxy-ethyl)-2-(morpholin-4-yl)-8-trifluoromethyl-6,7,8,9-tetrahydro-4H-pyrimido[1,2-a]pyrimidin-4-one

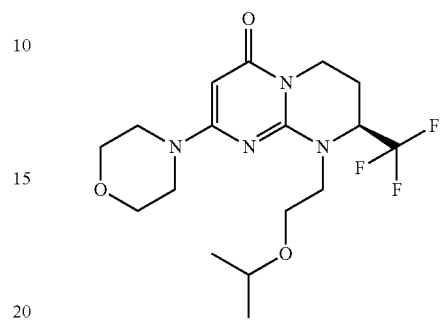

To 2.18 g (7.165 mmol) of (S)-2-(morpholin-4-yl)-8-trifluoromethyl-6,7,8,9-tetrahydro-4H-pyrimido[1,2-a]pyrimidin-4-one, suspended in 120 cm³ of acetonitrile, are added at a temperature close to 20° C., 3.03 g (9.312 mmol) of 2-isopropoxy-ethyl toluene-4-sulfonate and 2.40 g (9.312 mmol) of cesium carbonate. After 16 hours of stirring with reflux of the acetonitrile, the reaction medium is dry concentrated under reduced pressure (2.7 kPa) and then diluted in 130 cm³ of dichloromethane and washed three times with 40 cm³ of distilled water and then 30 cm³ of a solution saturated with sodium chloride. The organic phase is dried on anhydrous magnesium sulfate, filtered and dry concentrated under reduced pressure (2.7 kPa) in order to obtain 3.7 g of a pale yellow oil which is purified by flash chromatography on silica [eluent: dichloromethane/methanol/acetonitrile (98/1/1 by volume)]. After concentration of the fractions under reduced pressure (2.7 kPa), a yellow oil is obtained, which is triturated in 5 cm³ of diisopropyl ether for 30 mins. After filtration of the solid, 1.96 g of (S)-9-(2-isopropoxy-ethyl)-2-(morpholin-4-yl)-8-trifluoromethyl-6,7,8,9-tetrahydro-4H-pyrimido[1,2-a]pyrimidin-4-one are obtained as a white solid melting at 115.5° C. and including the following characteristics:

$[\alpha]_D^{25}$ at 589 nm=+59.1 (c=2.05 mg/0.5 mL DMSO)

Mass spectrum ES+/−: [M+H]+: m/z 391. Rt (min)=0.85, method A.

¹H NMR spectrum (400 MHz, δ in ppm, DMSO-d6): 1.05 (d, J=6.1 Hz, 3H); 1.07 (d, J=6.1 Hz, 3H); 2.06 (m, 1H); 2.36 (m, 1H); 3.17 (m, 1H); 3.32-3.44 (m, 5H); 3.49-3.67 (m, 7H); 4.10-4.24 (m, 2H); 4.59 (m, 1H); 4.98 (s, 1H).

(8S)-2-(morpholin-4-yl)-8-(trifluoromethyl)-6,7,8,9-tetrahydro-4H-pyrimido[1,2-a]-pyrimidin-4-one may be prepared as described in Example 1b.

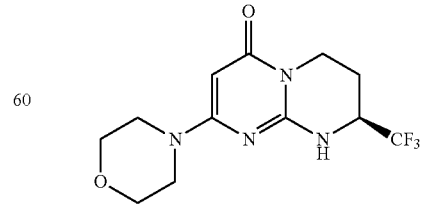

2-isopropoxy-ethyl toluene-4-sulfonate may be prepared as described in patent US2008/21032 A1.

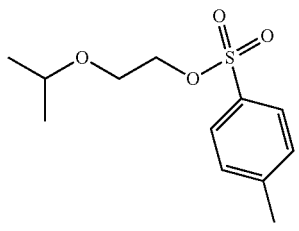 [SMILES: Cc1ccc(S(=O)(=O)OCCOC(C)C)cc1]

Example 6b (S)-2-(Morpholin-4-yl)-9-[2-(2,2,2-trifluoro-ethoxy)-ethyl]-8-(trifluoromethyl)-6,7,8,9-tetrahydro-4H-pyrimido[1,2-a]pyrimidin-4-one

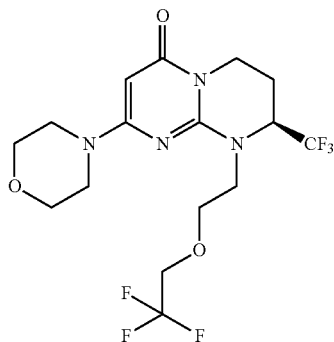 [SMILES: O=c1cc(N2CCOCC2)nc2n1CC[C@@H](C(F)(F)F)N2CCOCC(F)(F)F]

To 0.3 g (0.986 mmol) of (S)-2-(morpholin-4-yl)-8-(trifluoromethyl)-6,7,8,9-tetrahydro-4H-pyrimido[1,2-a]pyrimidin-4-one, suspended in 12 cm³ of acetonitrile, are added at a temperature close to 20° C., 0.481 g (2.958 mmol) of 5-chloro-1,1,1-trifluoro-3-oxapentane and 1.285 g (3.944 mmol) of cesium carbonate. After 1 hour of stirring at 160° C. in a microwave appliance, the reaction medium is poured into 40 cm³ of ethyl acetate and then washed three times with 25 cm³ of distilled water. The aqueous phases are collected and then extracted with 20 cm³ of ethyl acetate. The organic phases are collected, dried on anhydrous magnesium sulfate, filtered and dry concentrated under reduced pressure (2.7 kPa) in order to obtain 0.4 g of an orange oil. This oil is purified by flash chromatography on silica [eluent: dichloromethane/methanol/acetonitrile (92/4/4 by volume)]. After concentration of the fractions under reduced pressure, 0.35 g of an orange oil which is triturated in 6 cm³ of diisopropyl ether for 30 minutes, are obtained. After filtration of the solid, this operation is repeated a second time. The solid is washed for a last time with 5 cm³ of pentane and then dried under reduced pressure (2.7 kPa) in order to obtain 0.091 g of (S)-2-(morpholin-4-yl)-8-(trifluoromethyl)-6,7,8,9-tetrahydro-4H-pyrimido[1,2-a]pyrimidin-4-one as a white solid melting at 107.8° C. and including the following characteristics:

$[\alpha]_D^{25}$ at 589 nm=+86 (c=1.618 mg/0.5 mL MeOH)

Mass spectrum (method A) (ES+/−) [M+H]+: m/z 431.

¹H NMR spectrum (400 MHz, δ in ppm, DMSO-d6): 2.08 (m, 1H); 2.37 (m, 1H); 3.19 (m, 1H); 3.21-3.51 (m partly hidden, 5H); 3.61 (m, 4H); 3.75-3.93 (m, 2H); 4.09 (q, J=9.5 Hz, 2H); 4.18 (m, 1H); 4.58 (m, 1H); 4.99 (s, 1H).

(8S)-2-(morpholin-4-yl)-8-(trifluoromethyl)-6,7,8,9-tetrahydro-4H-pyrimido[1,2-a]-pyrimidin-4-one may be prepared as described in Example 1b.

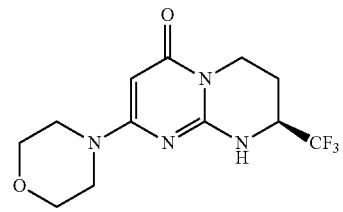 [SMILES: O=c1cc(N2CCOCC2)nc2n1CC[C@@H](C(F)(F)F)N2]

Example 7b (8S)-3-Fluoro-9-(2-isopropoxy-ethyl)-2-(morpholin-4-yl)-8-(trifluoromethyl)-6,7,8,9-tetrahydro-4H-pyrimido[1,2-a]pyrimidin-4-one

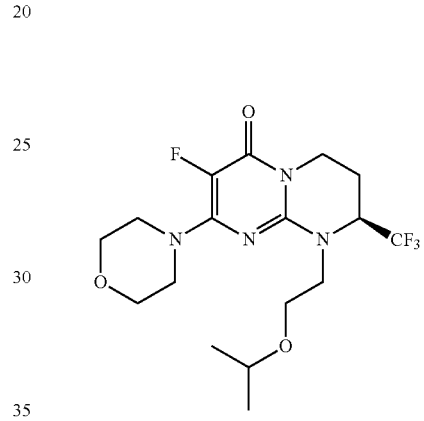

To 0.075 g (0.209 mmol) of (8S)-2-chloro-3-fluoro-9-(2-isopropoxy-ethyl)-8-(trifluoromethyl)-6,7,8,9-tetrahydro-4H-pyrimido[1,2-a]pyrimidin-4-one, in solution in 2 cm³ of acetonitrile, is added at a temperature close to 20° C., 1 mL of morpholine. After 1 hour of stirring at 100° C. in a microwave appliance, the reaction medium is poured into 10 cm³ of ethyl acetate and then washed three times with 10 cm³ of distilled water. The organic phase is dried on anhydrous magnesium sulfate, filtered and dry concentrated under reduced pressure (2.7 kPa) in order to obtain a colorless oil which is triturated in 5 cm³ pf pentane for 1 h. After filtration of the solid and washing with twice 2 cm³ of pentane, 0.055 g of (8S)-3-fluoro-9-(2-isopropoxy-ethyl)-2-(morpholin-4-yl)-8-(trifluoromethyl)-6,7,8,9-tetrahydro-4H-pyrimido[1,2-a]pyrimidin-4-one are obtained as a white solid melting at 117° C. and including the following characteristics:

$[\alpha]_D^{25}$ at 589 nm=+59+/−0.9 (c=2.875 mg/0.5 mL DMSO)

Mass spectrum (method A) (ES+/−) [M+H]+: m/z 409.

¹H NMR spectrum (400 MHz, δ in ppm, DMSO-d6): 1.06 (d, J=6.1 Hz, 3H); 1.08 (d, J=6.1 Hz, 3H); 2.08 (m, 1H); 2.39 (m, 1H); 3.123 (m, 1H); 3.36 (m, 1H); 3.53 (m, 6H); 3.58-3.67 (m, 5H); 4.07-4.24 (m, 2H); 4.60 (m, 1H).

(8S)-2-chloro-3-fluoro-9-(2-isopropoxy-ethyl)-8-(trifluoromethyl)-6,7,8,9-tetrahydro-4H-pyrimido[1,2-a]pyrimidin-4-one may be prepared in the following way.

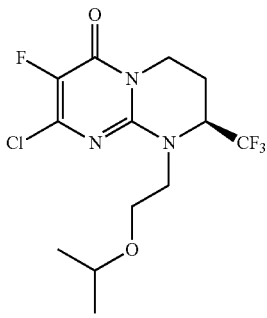 [SMILES: CC(C)OCCN1c2nc(Cl)c(F)c(=O)n2CC[C@H]1C(F)(F)F]

To 0.15 g (0.552 mmol) of (8S)-2-chloro-3-fluoro-8-(trifluoromethyl)-6,7,8,9-tetrahydro-4H-pyrimido[1,2-a]pyrimidin-4-one, in solution in 3 cm³ of acetonitrile, are added at a temperature close to 20° C., 0.157 g (0.607 mmol) of 2-isopropoxy-ethyl toluene-4-sulfonate and 0.2 g (0.607 mmol) of cesium carbonate. After 1 hour of stirring at 100° C. in a microwave appliance, the reaction medium is poured into 25 cm³ of ethyl acetate and then washed twice with 10 cm³ of distilled water. The organic phase is dried on anhydrous magnesium sulfate, filtered and dry concentrated under reduced pressure (2.7 kPa) in order to obtain 0.254 g of a residue. This residue is purified by flash chromatography on silica [eluent: cyclohexane/ethyl acetate (8/2 by volume)]. After concentration of the fractions under reduced pressure (2.7 kPa), 0.86 g of (8S)-2-chloro-3-fluoro-9-(2-isopropoxy-ethyl)-8-(trifluoromethyl)-6,7,8,9-tetrahydro-4H-pyrimido[1,2-a]-pyrimidin-4-one are obtained as a colorless oil including the following characteristics:

Mass spectrum (method A) (ES+/−) [M+H]+: m/z 358.

¹H NMR spectrum (400 MHz, δ in ppm, DMSO-d6): 1.06 (d, J=6.1 Hz, 3H); 1.08 (d, J=6.1 Hz, 3H); 2.12 (m, 1H); 2.43 (m, 1H); 3.31-3.44 (m, 2H); 3.51-3.68 (m, 3H); 4.17 (ddd, J=4.1 and 5.3 and 14.2 Hz, 1H); 4.25 (ddd, J=1.4 and 6.3 and 14.2 Hz, 1H); 4.70 (m, 1H).

2-isopropoxy-ethyl toluene-4-sulfonate may be prepared as described in patent US2008/21032 A1

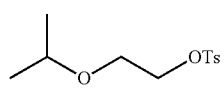 [SMILES: Cc1ccc(S(=O)(=O)OCCOC(C)C)cc1]

(8S)-2-chloro-3-fluoro-8-(trifluoromethyl)-6,7,8,9-tetrahydro-4H-pyrimido[1,2-a]pyrimidin-4-one may be prepared in the following way.

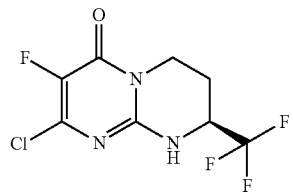 [SMILES: O=c1c(F)c(Cl)nc2n1CC[C@@H](C(F)(F)F)N2]

The separation of the enantiomers of (8R,8S)-2-chloro-3-fluoro-8-(trifluoromethyl)-6,7,8,9-tetrahydro-4H-pyrimido[1,2-a]pyrimidin-4-one is achieved by chiral chromatography (Chiralpak AD 20 μm 80×350 mm 250 mL/min 254 nm; 5% EtOH 5% MeOH 90% heptane+0.1% TEA), of 6.8 g of a racemic mixture. The dextro-rotatory enantiomer is concentrated in order to obtain 3.13 g of (8S)-2-chloro-3-fluoro-8-(trifluoromethyl)-6,7,8,9-tetrahydro-4H-pyrimido[1,2-a]pyrimidin-4-one, as a white solid, including the following characteristics:

$[\alpha]_D^{25}$ at 589 nm=+19.6+/−0.6 (c=2.488 mg/0.5 mL MeOH)

Mass spectrum (method A) (ES+/−) [M+H]+: m/z 272; [M−H]−: m/z 270; Rt (min)=0.62.

(8R,8S)-2-chloro-3-fluoro-8-(trifluoromethyl)-6,7,8,9-tetrahydro-4H-pyrimido[1,2-a]pyrimidin-4-one may be prepared in the following way.

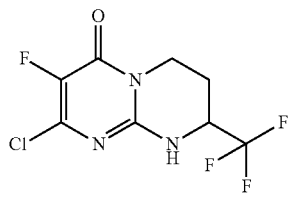 [SMILES: O=c1c(F)c(Cl)nc2n1CCC(C(F)(F)F)N2]

To a solution of 6.5 g of (8R,8S)-3-fluoro-2-hydroxy-8-(trifluoromethyl)-6,7,8,9-tetrahydro-4H-pyrimido[1,2-a]pyrimidin-4-one in 20 mL of 1,2-dichloroethane are added 8 mL of phosphorus trichloride. After 4 hours of stirring at a temperature of 65° C. and returning to a temperature close to 20° C., the reaction mixture is dry concentrated under reduced pressure. The residue is diluted in 150 mL of ethyl acetate and 10 mL of iced water. At a temperature comprised between 0° C. and 10° C., is added a concentrated solution of sodium hydroxide until a pH is obtained comprised between 6 and 7. The formed solid is filtered in order to obtain 3.5 g of a beige solid S1. The filtrate is decanted and the organic phase is dried on anhydrous magnesium sulfate, filtered and dry concentrated under reduced pressure. After purification of the residue on a silica column (eluent: CH₂Cl₂/MeOH 97/03), 3.3 g of a pale yellow solid S2 are obtained. Both solids S1 and S2 are gathered together in order to obtain 6.8 g of (8R,8S)-2-chloro-3-fluoro-8-(trifluoromethyl)-6,7,8,9-tetrahydro-4H-pyrimido[1,2-a]pyrimidin-4-one, as a pale yellow powder, including the following characteristics:

Mass spectrum (method B) (ES+/−) [M+H]+: m/z 272; [M−H]−: m/z 270; Rt (min)=2.9.

(8R,8S)-3-fluoro-2-hydroxy-8-(trifluoromethyl)-6,7,8,9-tetrahydro-4H-pyrimido[1,2-a]pyrimidin-4-one may be prepared in the following way.

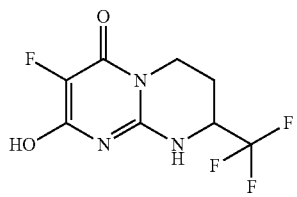 [SMILES: O=c1c(F)c(O)nc2n1CCC(C(F)(F)F)N2]

To a suspension of 7 g of (4R,4S)-4-(trifluoromethyl)-1,4,5,6-tetrahydropyrimidin-2-ylamine hydrochloride in 35 mL of dimethylfluoropropanedioate, are added 5.6 g of sodium methylate. After 3 hours of stirring of the suspension at a temperature of 100° C., the obtained medium is dry concentrated under reduced pressure. The residue is taken up in diethyl oxide and then dried in vacuo. The obtained solid is taken up in 14 mL of water and the resulting mixture is cooled in ice before acidification down to pH 5-6 by adding concentrated (25%) hydrochloric acid. After 2 hours of stirring at a temperature of 0° C. and one night at a temperature close to 20° C., the suspension is filtered and the solid is wrung and dried in vacuo on P₂O₅. 6.5 g of (8R,8S)-3-fluoro-2-hydroxy-8-(trifluoromethyl)-6,7,8,9-tetrahydro-4H-pyrimido[1,2-a]pyrimidin-4-one, are obtained as a yellow powder, including the following characteristics:

Mass spectrum (method A) (ES+/−) [M+H]⁺: m/z 254; [M−H]⁻: m/z 252; Rt (min)=0.28.

(4R,4S)-4-(trifluoromethyl)-1,4,5,6-tetrahydropyrimidin-2-ylamine hydrochloride may be prepared as described in Example 1b.

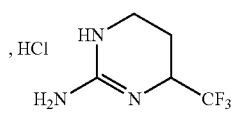

Example 8b (8S)-9-(2-Hydroxy-2-methylpropyl)-2-(morpholin-4-yl)-8-(trifluoromethyl)-6,7,8,9-tetrahydro-4H-pyrimido[1,2-a]pyrimidin-4-one

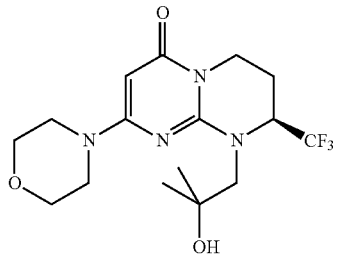 [SMILES: CC(C)(O)CN1c2nc(N3CCOCC3)cc(=O)n2CC[C@H]1C(F)(F)F]

A suspension of 370 mg (1.216 mmol) de (8S)-2-(morpholin-4-yl)-8-(trifluoromethyl)-6,7,8,9-tetrahydro-4H-pyrimido[1,2-a]pyrimidin-4-one, 877 mg (12.16 mmol) of 2,2-dimethyloxirane and 198 mg (0.608 mmol) of cesium carbonate in 4 cm³ of acetonitrile is heated in the microwave appliance to 120° C. for 1 h. The reaction medium is diluted with dichloromethane and then filtered on cotton and the filtrate is dry evaporated under reduced pressure (2.7 kPa). The obtained crude is purified by flash chromatography on silica [eluent: dichloromethane/propanol-1/acetonitrile (86/7/7 by volume)]. After evaporation of the fractions under reduced pressure, 62 mg of (8S)-9-(2-hydroxy-2-methylpropyl)-2-(morpholin-4-yl)-8-(trifluoromethyl)-6,7,8,9-tetrahydro-4H-pyrimido[1,2-a]pyrimidin-4-one are obtained as a white solid including the following characteristics:

[α]$_D^{25}$ at 589 nm=+36.4+/−0.9 in DMSO; C=3.96 mg/mL

Mass spectrum (method A): ES+/−: [M+H]⁺: m/z 377; [M−H+HCO2H]⁻: m/z 421

¹H NMR spectrum (400 MHz, δ in ppm, DMSO-d6): 1.03 (s, 3H); 1.15 (s, 3H); 2.24 (m, 1H); 2.40 (m, 1H); 3.01 (d, J=14.5 Hz, 1H); 3.18-3.43 (m partly hidden, 5H); 3.61 (m, 4H); 4.13 (m, 1H); 4.49 (d, J=14.5 Hz, 1H); 4.76 (s broad, 1H); 4.90 (m, 1H); 4.95 (s, 1H).

(8S)-2-(morpholin-4-yl)-8-(trifluoromethyl)-6,7,8,9-tetrahydro-4H-pyrimido[1,2-a]-pyrimidin-4-one may be prepared as described in Example 1b.

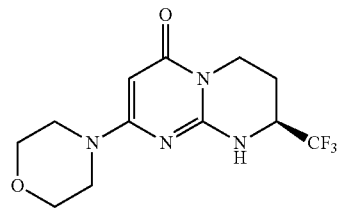 [SMILES: O=c1cc(N2CCOCC2)nc2n1CC[C@@H](C(F)(F)F)N2]

Example 9b (S)-9-(2-Hydroxy-2-methyl-propyl)-3-methyl-2-(morpholin-4-yl)-8-trifluoromethyl-6,7,8,9-tetrahydro-4H-pyrimido[1,2-a]pyrimidin-4-one

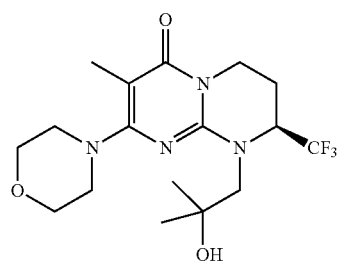 [SMILES: Cc1c(N2CCOCC2)nc2n(c1=O)CC[C@@H](C(F)(F)F)N2CC(C)(C)O]

and

Example 10b (S)-9-(2-Methoxy-2-methyl-propyl)-2-(morpholin-4-yl)-8-trifluoromethyl-6,7,8,9-tetrahydro-4H-pyrimido[1,2-a]pyrimidin-4-one

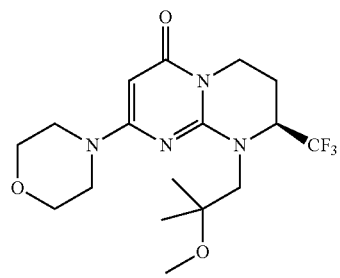 [SMILES: COC(C)(C)CN1c2nc(N3CCOCC3)cc(=O)n2CC[C@H]1C(F)(F)F]

To 0.140 g (0.372 mmol) of (S)-9-(2-hydroxy-2-methyl-propyl)-2-(morpholin-4-yl)-8-trifluoromethyl-6,7,8,9-tetrahydro-4H-pyrimido[1,2-a]pyrimidin-4-one, suspended in 6 cm³ of dimethylformamide, are added at a temperature close to 20° C., 30 mg (0.744 mmol) of 60% sodium hydride in oil and 0.264 g (1.860 mmol) of iodomethane. After 16 hours of stirring at 50° C., 10 cm³ of distilled water are added. The reaction medium is dry concentrated under reduced pressure (2.7 kPa) and then diluted in 30 cm³ ethyl acetate and washed three times with 20 cm³ of distilled water and then with 20 cm³ of solution saturated with sodium chloride. The organic phase is dried on anhydrous magnesium sulfate, filtered and dry concentrated under reduced pressure (2.7 kPa) in order to obtain 95 mg of a pale yellow solid which is purified by flash chromatography on silica [eluent: dichloromethane/methanol/acetonitrile (96/2/2 by volume)]. After concentration of the fractions under reduced pressure (2.7 kPa), 19.6 mg of (S)-9-(2-methoxy-2-methyl-propyl)-2-(morpholin-4-yl)-8-trifluoromethyl-6,7,8,9-tetrahydro-4H-pyrimido[1,2-a]pyrimidin-4-one, are obtained as a white solid melting at 172° C. and including the following characteristics:

[α]$_D^{25}$ at 589 nm=+31.2 (c=2.897 mg/0.5 mL DMSO)

Mass spectrum ES+/−: [M+H]$^+$: m/z 391. Rt (min)=0.84, method A.

$^1$H NMR spectrum (400 MHz, δ in ppm, DMSO-d6): 1.07 (s, 3H); 1.13 (s, 3H); 2.18 (m, 1H); 2.39 (m, 1H); 3.12 (d, J=14.7 Hz, 1H); 3.14 (s, 3H); 3.24 (m, 1H); 3.32-3.45 (m, 4H); 3.55-3.67 (m, 4H); 4.13 (dd, J=6.6 and 14.9 Hz, 1H); 4.54 (d, J=14.7 Hz, 1H); 4.73 (m, 1H); 4.96 (s, 1H).

and 10.2 mg of (S)-9-(2-hydroxy-2-methyl-propyl)-3-methyl-2-(morpholin-4-yl)-8-trifluoromethyl-6,7,8,9-tetrahydro-4H-pyrimido[1,2-a]pyrimidin-4-one, as a white solid melting at 170° C. and including the following characteristics:

Mass spectrum ES+/−: [M+H]$^+$: m/z 391. Rt (min)=0.71, method A.

$^1$H NMR spectrum (400 MHz, δ in ppm, DMSO-d6): 1.05 (s, 3H); 1.16 (s, 3H); 1.80 (s, 3H); 2.24 (m, 1H); 2.41 (m, 1H); 3.02 (d, J=14.4 Hz, 1H); 3.09-3.18 (m, 4H); 3.30 (m partly hidden, 1H); 3.57-3.73 (m, 4H); 4.17 (dd, J=7.0 and 14.3 Hz, 1H); 4.53 (d, J=14.4 Hz, 1H); 4.76 (s, 1H); 4.92 (m, 1H).

(S)-9-(2-hydroxy-2-methyl-propyl)-2-(morpholin-4-yl)-8-trifluoromethyl-6,7,8,9-tetrahydro-4H-pyrimido[1,2-a]pyrimidin-4-one may be prepared as in Example 8b.

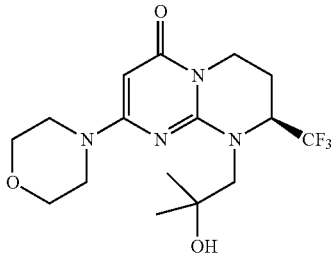 [SMILES: CC(C)(O)CN1c2nc(N3CCOCC3)cc(=O)n2CC[C@H]1C(F)(F)F]

Example 11Ab (8S)-8-Methyl-2-(morpholin-4-yl)-9-(2-(propan-2-yloxy)ethyl)-8-(trifluoromethyl)-6,7,8,9-tetrahydro-4H-pyrimido[1,2-a]pyrimidin-4-one

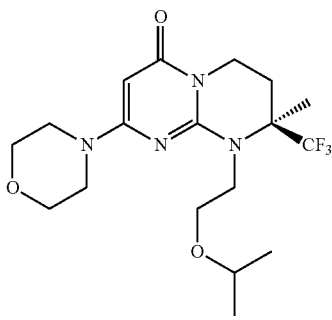 [SMILES: CC(C)OCCN1c2nc(N3CCOCC3)cc(=O)n2CC[C@@]1(C)C(F)(F)F]

and

Example 11Bb (8R)-8-Methyl-2-(morpholin-4-yl)-9-(2-(propan-2-yloxy)ethyl)-8-(trifluoromethyl)-6,7,8,9-tetrahydro-4H-pyrimido[1,2-a]pyrimidin-4-one

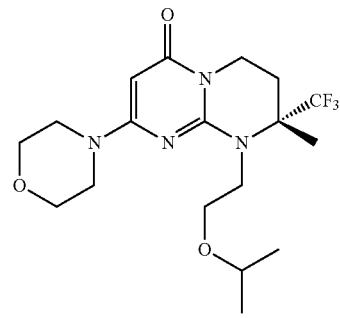 [SMILES: CC(C)OCCN1c2nc(N3CCOCC3)cc(=O)n2CC[C@]1(C)C(F)(F)F]

8-Methyl-2-(morpholin-4-yl)-9-(2-(propan-2-yloxy)ethyl)-8-(trifluoromethyl)-6,7,8,9-tetrahydro-4H-pyrimido[1,2-a]pyrimidin-4-one

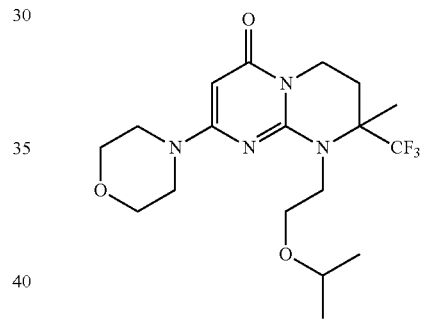

A suspension of 51 mg (0.160 mmol) of 8-methyl-2-(morpholin-4-yl)-8-(trifluoromethyl)-6,7,8,9-tetrahydro-4H-pyrimido[1,2-a]pyrimidin-4-one, of 54 mg (0.208 mmol) of 2-isopropoxy-ethyl toluene-4-sulfonate and of 68 mg (0.208 mmol) of cesium carbonate in 2 cm$^3$ of DMF is heated to 90° C. for 14 h. The reaction medium is diluted with 20 cm$^3$ of ethyl acetate and the organic phase is then washed four times with 20 cm$^3$ of water and 20 cm$^3$ of brine, dried on anhydrous magnesium sulfate, filtered and dry concentrated under reduced pressure (2.7 kPa). The obtained crude is purified by flash chromatography on silica [eluent: dichloromethane/propanol-1/acetonitrile (90/5/5 by volume)]. After evaporation of the fractions under reduced pressure, 27 mg of 8-methyl-2-(morpholin-4-yl)-9-(2-(propan-2-yloxy)ethyl)-8-(trifluoromethyl)-6,7,8,9-tetrahydro-4H-pyrimido[1,2-a]pyrimidin-4-one are obtained as a pale yellow solid pale including the following characteristics:

Mass spectrum (method A): ES+/−: [M+H]$^+$: m/z 405

$^1$H NMR spectrum (300 MHz, δ in ppm, DMSO-d6): 1.06 (m, 6H); 1.61 (s, 3H); 2.07 (m, 1H); 2.36 (m, 1H); 3.36-3.44 (m, 5H); 3.47-3.58 (m, 4H); 3.59-3.66 (m, 4H); 3.84 (m, 1H); 3.97 (m, 1H); 5.00 (s, 1H).

The mixture of enantiomers is purified by preparative chromatography on a chiral column under the following conditions:

Apparatus: Pic Solution Miniprep

Chiral stationary phase: Whelk01 SS 5 m graft kromasil 3×25 cm

Mobile phase: heptane 50%-EtOH 50%

Flow rate: 40 mL/min

Detection: UV 230 nm

After evaporation of the fractions under reduced pressure, 3 mg of (8S)-8-Methyl-2-(morpholin-4-yl)-9-(2-(propan-2-yloxy)ethyl)-8-(trifluoromethyl)-6,7,8,9-tetrahydro-4H-pyrimido[1,2-a]pyrimidin-4-one are obtained as a white solid including the following characteristics:

Mass spectrum (method A): ES+/−: [M+H]⁺: m/z 405

¹H NMR spectrum (500 MHz, δ in ppm, DMSO-d6): 1.06 (m, 6H); 1.61 (s, 3H); 2.07 (m, 1H); 2.36 (m, 1H); 3.36 (m, 1H); 3.41 (m, 4H); 3.47-3.57 (m, 4H); 3.62 (m, 4H); 3.86 (m, 1H); 3.97 (m, 1H); 5.00 (s, 1H).

Retention time with HPLC on a chiral phase: 11.6 minutes

Conditions used for HPLC on a chiral phase:

Apparatus: Gilson

Chiral stationary phase: Whelk01 SS 5 μm 250×4.6 mm

Mobile phase: heptane 50%-EtOH 50%

Flow rate: 1 mL/min

Detection: UV 254 nm

After evaporation of the fractions under reduced pressure, 10 mg of (8R)-8-methyl-2-(morpholin-4-yl)-9-(2-(propan-2-yloxy)ethyl)-8-(trifluoromethyl)-6,7,8,9-tetrahydro-4H-pyrimido[1,2-a]pyrimidin-4-one are also obtained as a white solid including the following characteristics:

Mass spectrum (method A): ES+/−: [M+H]+: m/z 405

¹H NMR spectrum (400 MHz, δ in ppm, DMSO-d6): 1.06 (m, 6H); 1.61 (s, 3H); 2.07 (m, 1H); 2.36 (m, 1H); 3.36 (m, 1H); 3.40 (m, 4H); 3.47-3.56 (m, 4H); 3.62 (m, 4H); 3.86 (m, 1H); 3.97 (m, 1H); 5.00 (s, 1H).

Retention time with HPLC on a chiral phase: 14.4 minutes

Conditions used for HPLC on a chiral phase:

Apparatus: Gilson

Chiral stationary phase: Whelk01 SS 5 μm 250×4.6 mm

Mobile phase: heptane 50%-EtOH 50%

Flow rate: 1 mL/min

Detection: UV 254 nm 2-isopropoxy-ethyl toluene-4-sulfonate may be prepared as described in patent US2008/21032 A1.

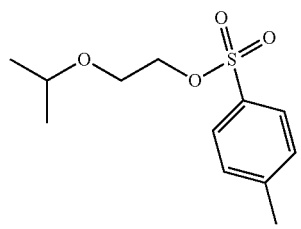 [SMILES: Cc1ccc(S(=O)(=O)OCCOC(C)C)cc1]

(8R,8S)-8-methyl-2-(morpholin-4-yl)-8-(trifluoromethyl)-6,7,8,9-tetrahydro-4H-pyrimido[1,2-a]pyrimidin-4-one may be prepared in the following way.

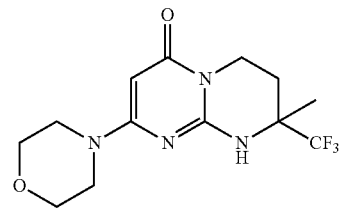 [SMILES: CC1(C(F)(F)F)CCn2c(nc(N3CCOCC3)cc2=O)N1]

A suspension of 97 mg (0.362 mmol) of (8R,8S)-2-chloro-8-methyl-8-(trifluoromethyl)-6,7,8,9-tetrahydro-4H-pyrimido[1,2-a]pyrimidin-4-one in 4 cm³ of acetonitrile is treated at room temperature with 0.957 cm³ (10.870 mmol) of morpholine. The reaction medium is heated to 80° C. for 4 h 15 mins and then dry evaporated. The obtained residue is taken up in 10 cm³ of ethyl acetate and 2 cm³ of water. The organic phase is separated, washed with 2 cm³ of water, dried on anhydrous magnesium sulfate, filtered and dry concentrated under reduced pressure (2.7 kPa). The obtained crude is purified by flash chromatography on silica [eluent: dichloromethane/propanol-1/acetonitrile (90/5/5 by volume)]. After evaporation of the fractions under reduced pressure, 53 mg of (8R,8S)-8-methyl-2-(morpholin-4-yl)-8-(trifluoromethyl)-6,7,8,9-tetrahydro-4H-pyrimido[1,2-a]pyrimidin-4-one are obtained as an off-white solid including the following characteristics:

Mass spectrum (method A): ES+/−: [M+H]⁺: m/z 319; [M−H]⁻: m/z 317

¹H NMR spectrum (300 MHz, δ in ppm, DMSO-d6): 1.43 (s, 3H); 1.91 (m, 1H); 2.29 (m, 1H); 3.30-3.53 (m, 5H); 3.60 (m, 4H); 4.05 (m, 1H); 4.92 (s, 1H); 8.12 (s broad, 1H).

(8R,8S)-2-chloro-8-methyl-8-(trifluoromethyl)-6,7,8,9-tetrahydro-4H-pyrimido-[1,2-a]pyrimidin-4-one may be prepared in the following way.

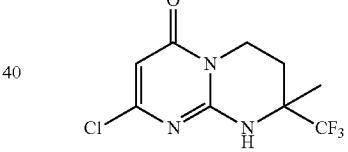

A suspension of 91 mg (0.365 mmol) of (8R,8S)-2-hydroxy-8-methyl-8-(trifluoromethyl)-6,7,8,9-tetrahydro-4H-pyrimido[1,2-a]pyrimidin-4-one in 3 cm³ of 1,2-dichloroethane is treated at room temperature with 0.170 cm³ (1.826 mmol) of POCl₃. The reaction medium is heated to 65° C. for 1 h 30 mins and then 2 cm³ of 1,2-dichloroethane are added and the reaction medium is heated to 65° C. for 6 h. The reaction medium is dry evaporated and the obtained residue is then diluted with 10 cm³ of ethyl acetate and 0.5 cm³ of water and then cooled in a ice-water bath and basified up to pH=10 with a 32% sodium hydroxide aqueous solution. The organic phase is separated, the aqueous phase is extracted with 8 cm³ of ethyl acetate and then the organic phase are combined, dried on anhydrous magnesium sulfate, filtered and dry evaporated under reduced pressure (2.7 kPa). 102 mg of (8R,8S)-2-chloro-8-methyl-8-(trifluoromethyl)-6,7,8,9-tetrahydro-4H-pyrimido[1,2-a]pyrimidin-4-one are obtained as a brown solid including the following characteristics:

Mass spectrum (method A): ES+/−: [M+H]+: m/z 268; [M−H]−: m/z 266

(8R,8S)-2-hydroxy-8-methyl-8-(trifluoromethyl)-6,7,8,9-tetrahydro-4H-pyrimido-[1,2-a]pyrimidin-4-one may be prepared in the following way.

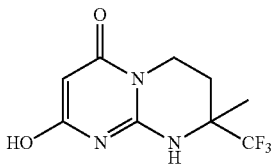 [SMILES: CC1(C(F)(F)F)CCn2c(nc(O)cc2=O)N1]

A solution of 44 mg (1.927 mmol) of sodium in 4 cm³ of methanol is treated at room temperature with a solution of 101 mg (0.385 mmol) of (4R,4S)-4-methyl-4-(trifluoromethyl)-tetrahydropyrimidin-2(1H)-imine hydrobromide in 2 cm³ of methanol and then with 0.264 cm³ (2.312 mmol) of dimethyl propanedioate. The reaction medium is stirred at room temperature for 5 minutes and then heated with reflux for 5 h 45 mins. After cooling, the reaction medium is dry evaporated and the obtained residue is then taken up with 0.5 cm³ of water and cooled in an ice-water bath and acidified up to pH=5 with 8N HCl. After stirring for about 15 minutes, 3 cm³ of ether are added and the reaction medium is then filtered on a frit and dried in vacuo. 92 mg of (8R,8S)-2-hydroxy-8-methyl-8-(trifluoromethyl)-6,7,8,9-tetrahydro-4H-pyrimido[1,2-a]pyrimidin-4-one are obtained as a beige solid including the following characteristics:

Mass spectrum (method A): ES+/−: [M+H]⁺: m/z 250; [M−H]⁻: m/z 248

¹H NMR spectrum (300 MHz, δ in ppm, DMSO-d6): 1.40 (s, 3H); 1.92 (m, 1H); 2.22 (m, 1H); 3.45 (m, 1H); 3.95 (m, 1H); 4.61 (s broad, 1H); 10.30 (m spread, 2H).

(4R,4S)-4-methyl-4-(trifluoromethyl)-tetrahydropyrimidin-2(1H)-imine hydrobromide may be prepared in the following way.

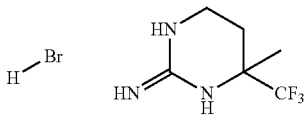

A solution of 87 mg (0.557 mmol) of (3R,3S)-4,4,4-trifluoro-3-methylbutane-1,3-diamine in 1 cm³ of acetonitrile is treated at room temperature with 59 mg (0.557 mmol) of cyanogen bromide and then 2 cm³ of acetonitrile are added. The reaction medium is heated with reflux for 3 h and then dry evaporated. 106 mg of (3R,3S)-4-methyl-4-(trifluoromethyl)-tetrahydropyrimidin-2(1H)-imine hydrobromide are obtained as a brown solid including the following characteristics:

Mass spectrum (method A): ES+/−: [M+H]⁺: m/z 182

¹H NMR spectrum (300 MHz, δ in ppm, DMSO-d6): 1.45 (s, 3H); 1.94 (m, 1H); 2.17 (m, 1H); 3.11-3.44 (m partly hidden, 2H); 6.97 (s broad, 2H); 8.17 (s broad, 1H); 8.60 (s broad, 1H).

(3R,3S)-4,4,4-trifluoro-3-methylbutane-1,3-diamine may be prepared in the following way.

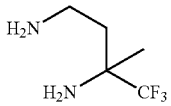

A suspension of 3.336 g (12.074 mmol) of (3R,3S)-4,4,4-trifluoro-N-1-(4-methoxybenzyl)-3-methylbutane-1,3-diamine and 2.570 g (2.415 mmol) of 10% palladium on coal in 135 cm³ of methanol and 5.31 cm³ of 5N HCl is hydrogenated in an autoclave at 50° C. under 10 bars of hydrogen for 4 days. The reaction medium is filtered on Celite and the filtrate is dry evaporated. The obtained brown solid is dissolved in 18 cm³ of water. The aqueous phase is washed three times with 50 cm³ of ether and then basified with 12 cm³ of a 32% sodium hydroxide aqueous solution up to a pH=12. Extraction is performed with 100 cm³ of ether and then twice with 50 cm³ of ether. The organic phases are combined, washed with 30 cm³ of an aqueous solution saturated with sodium chloride and then dried on anhydrous magnesium sulfate. After filtration on a frit, the filtrate is dry evaporated in a rotavapor (the temperature of the bath should not exceed 20° C. and the internal pressure of the pump of the rotavapor should not fall below 100 mbars). 1.765 g of (3R,3S)-4,4,4-trifluoro-3-methylbutane-1,3-diamine are obtained as a yellow liquid including the following characteristics:

Mass spectrum (method A): ES+/−: [M+H]⁺: m/z 157

¹H NMR spectrum (300 MHz, δ in ppm, DMSO-d6): 1.11 (s, 3H); 1.55 (m, 2H); 1.87 (m spread, 4H); 2.68 (m, 2H).

(3R,3S)-4,4,4-trifluoro-N1-(4-methoxybenzyl)-3-methylbutane-1,3-diamine may be prepared in the following way.

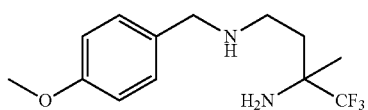 [SMILES: COc1ccc(CNCCC(C)(N)C(F)(F)F)cc1]

947 mg (24.95 mmol) of LiAlH₄ are added at room temperature under argon to a solution of 1.13 g (3.893 mmol) of (3R,3S)-3-amino-4,4,4-trifluoro-N-(4-methoxybenzyl)-3-methylbutanamide in 45 mL of ether. The reaction medium is stirred at room temperature for 25 h and then 10 cm³ of ether are added and stirring is performed at room temperature for 16 h. The reaction medium is cooled to 0° C. and 0.935 cm³ of water, 0.935 cm³ of a 15% sodium hydroxide aqueous solution, and 2.8 cm³ of water are then added successively. The mixture is filtered on a frit, the filtrate is dried on anhydrous magnesium sulfate and then filtered on a frit and the filtrate is dry evaporated. The obtained crude is purified by flash chromatography on silica (eluent: dichloromethane/acetonitrile/methanol). After evaporation of the fractions under reduced pressure, 365 mg of (3R,3S)-4,4,4-trifluoro-N1-(4-methoxybenzyl)-3-methylbutane-1,3-diamine are obtained as a colorless oil including the following characteristics:

Mass spectrum (method A): ES+/−: [M+H]⁺: m/z 277; base peak: m/z 1

¹H NMR spectrum (300 MHz, δ in ppm, DMSO-d6): 1.10 (s broad, 3H); 1.63 (m, 2H); 2.01 (m spread, 3H); 2.61 (m, 2H); 3.60 (s, 2H); 3.72 (s, 3H); 6.86 (d, J=8.8 Hz, 2H); 7.22 (d, J=8.8 Hz, 2H).

(3R,3S)-3-amino-4,4,4-trifluoro-N-(4-methoxybenzyl)-3-methylbutanamide may be prepared in the following way.

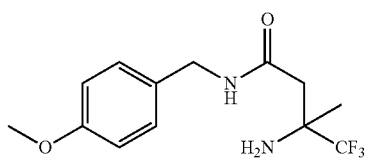 [SMILES: COc1ccc(CNC(=O)CC(C)(N)C(F)(F)F)cc1]

A suspension of 4.492 g (21.640 mmol) of (3R,3S)-3-amino-4,4,4-trifluoro-3-methylbutanoic acid hydrochloride in 100 cm³ of dichloromethane is treated at room temperature with 12.450 g (64.920 mmol) of N-(3-(dimethylamino)propyl)-N'-ethylcarbodiimide hydrochloride and 8.773 g (64.920 mmol) of hydroxybenzotriazole. Next, 13.250 cm³ (95.220 mmol) of triethylamine and 180 cm³ of dichloromethane are added as well as 8.458 cm³ of 4-methoxybenzylamine. The reaction mixture is stirred at room temperature for 15 h. And then 200 cm³ of dichloromethane are added and the reaction medium is stirred at room temperature for 30 minutes and then filtered on a frit. The obtained white solid is washed with 200 cm³ of dichloromethane, and the filtrate is then dry evaporated. The obtained crude is purified by flash chromatography on silica [eluent: dichloromethane/propanol-1/acetonitrile (98/1/1 then 96/2/2 by volume)]. After evaporation of the fractions under reduced pressure, 1.632 g of a yellow oil are obtained which is again purified by flash chromatography on silica [eluent: dichloromethane/propanol-1/acetonitrile (98/1/1 and then 96/2/2 by volume)]. After evaporation of the fractions under reduced pressure, 1.285 g of (3R,3S)-3-amino-4,4,4-trifluoro-N-(4-methoxybenzyl)-3-methylbutanamide are obtained as a colorless oil including the following characteristics:

Mass spectrum (method A): ES+/−: [M+H]⁺: m/z 291; [M−H]⁻: m/z 289

¹H NMR spectrum (300 MHz, δ in ppm, DMSO-d6): 1.22 (s, 3H); 2.20-2.44 (m, 4H); 3.73 (s, 3H); 4.22 (d, J=6.1 Hz, 2H); 6.88 (d, J=8.6 Hz, 2H); 7.20 (d, J=8.6 Hz, 2H); 8.46 (t broad, J=6.1 Hz, 1H).

(3R,3S)-3-amino-4,4,4-trifluoro-3-methylbutanoic acid hydrochloride may be prepared in the following way.

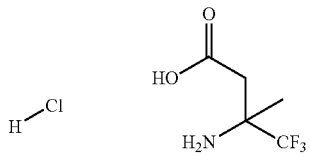

361.4 cm³ of aqueous 5N hydrochloric acid are slowly added at room temperature to 20 g (100.40 mmol) of ethyl (3R,3S)-3-amino-4,4,4-trifluoro-3-methylbutanoate. The reaction medium is stirred for 5 minutes at room temperature and then is heated to 90° C. for 3 h 30 mins. Toluene is added to the reaction medium and the latter is dry evaporated. This operation is carried out three times. 20.84 g of (3R,3S)-3-amino-4,4,4-trifluoro-3-methylbutanoic acid hydrochloride are obtained as a pale yellow solid including the following characteristics:

Mass spectrum (method A): ES+/−: [M+H]+: m/z 172; [M−H]−: m/z 171

¹H NMR spectrum (400 MHz, δ in ppm, DMSO-d6): 1.60 (s, 3H); 2.93 (m, 2H); 10.11 (m spread, 3H).

(3R,3S)-3-amino-4,4,4-trifluoro-3-methylbutanoate d'ethyle may be prepared in the following way.

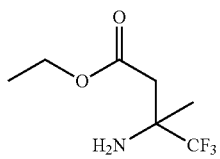

A solution of 1.5 g (8.235 mmol) of ethyl(2E)-4,4,4-trifluoro-3-methylbut-2-enoate and 11.76 cm³ (82.35 mmol) of ammonia (7N in methanol) in 6 cm³ of acetonitrile is heated to 130° C. for 1 h 20 mins in the microwave appliance. The reaction medium is diluted with 20 cm³ of dichloromethane and then dry evaporated under reduced pressure cautiously so as to have the temperature of the bath of the rotavapor remain below 25° C. and the vacuum of the pump of the rotavapor remain greater than 100 mbars. 1.355 g of ethyl(3R,3S)-3-amino-4,4,4-trifluoro-3-methylbutanoate are obtained as a yellow liquid including the following characteristics:

Mass spectrum (method A): ES+/−: [M+H]⁺: m/z 200

¹H NMR spectrum (400 MHz, δ in ppm, DMSO-d6): 1.19 (t, J=7.1 Hz, 3H); 1.28 (s, 3H); 2.18 (m spread, 2H); 3.17 (m, 2H); 4.08 (q, J=7.1 Hz, 2H).

Example 12b 9-(2-Methoxyethyl)-8,8-dimethyl-2-(morpholin-4-yl)-6,7,8,9-tetrahydro-4H-pyrimido[1,2-a]pyrimidin-4-one

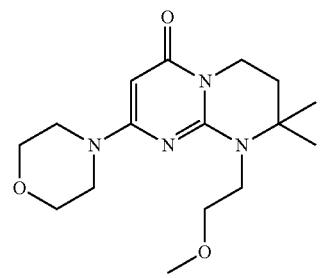 [SMILES: COCCN1c2nc(N3CCOCC3)cc(=O)n2CCC1(C)C]

0.07 g of 2-chloro-9-(2-methoxyethyl)-8,8-dimethyl-6,7,8,9-tetrahydro-4H-pyrimido-[1,2-a]pyrimidin-4-one in 2.5 mL of morpholine are heated with the microwave oven to 80° C. for 2 h. The crude is purified by flash chromatography on silica gel SiO₂ (100% CH₂Cl₂ to 92/8 CH₂Cl₂/MeOH). 0.050 g (yield=58%) of 9-(2-methoxyethyl)-8,8-dimethyl-2-(morpholin-4-yl)-6,7,8,9-tetrahydro-4H-pyrimido[1,2-a]-pyrimidin-4-one are obtained as a white solid including the following characteristics:

Mass spectrum LC/MS: Rt: 1.2 min, M/Z=323.

¹H NMR spectrum (400 MHz, δ in ppm, DMSO-d6): 1.29 (s, 6H), 1.84 (t, 2H), 3.26 (s, 3H), 3.37 (t, 4H), 3.50 (t, 2H), 3.55-3.64 (m, 6H), 3.68-3.75 (m, 2H), 4.89 (s, 1H)

2-chloro-9-(2-methoxyethyl)-8,8-dimethyl-6,7,8,9-tetrahydro-4H-pyrimido[1,2-a]-pyrimidin-4-one may be prepared in the following way.

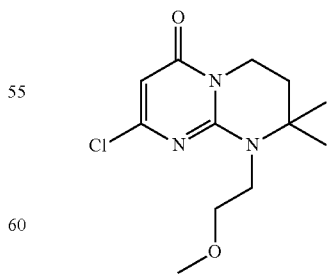

0.19 g of 2-chloro-8,8-dimethyl-6,7,8,9-tetrahydro-4H-pyrimido[1,2-a]pyrimidin-4-one are suspended in 7 mL de CH₃CN, 0.58 g of cesium carbonate and 0.27 g of 2-methoxyethyl methanesulfonate are added. The mixture is heated to 65° C. for 36 h. Water, ethyl acetate are added and then after decantation, the organic phase is dried with magnesium sulfate and then evaporated. The crude is purified by flash chromatography on silica gel SiO$_2$ (CH$_2$Cl$_2$/MeOH, 99/1). 0.17 g (yield=50%) of 2-chloro-9-(2-methoxyethyl)-8,8-dimethyl-6,7,8,9-tetrahydro-4H-pyrimido[1,2-a]pyrimidin-4-one are obtained as a brown powder including the following characteristics:

Mass spectrum (method A) ES+/−: 2.35 min, M/Z=272.

2-methoxyethyl methanesulfonate may be prepared as described by Tavecchia, P. et al. in Tetrahedron, 1995, Vol. 51, No. 16, p. 4867-4890.

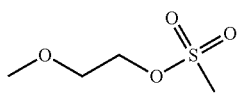

2-chloro-8,8-dimethyl-6,7,8,9-tetrahydro-4H-pyrimido[1,2-a]pyrimidin-4-one may be prepared in the following way.

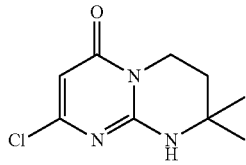

1.14 g of 2-hydroxy-8,8-dimethyl-6,7,8,9-tetrahydro-4H-pyrimido[1,2-a]pyrimidin-4-one are suspended in 28 mL of 1,2-dichloroethane. 12 mL of POCl$_3$ are added and then the medium is heated to 65° C. for 2 h. The medium is dry concentrated. The residue is taken up in 50 mL of EtOAc and 10 mL of H$_2$O and then cooled in an ice bath. Concentrated NaOH is added up to a pH 7. The aqueous phase is extracted with EtOAc, and then the organic phase is dried on magnesium sulfate. After evaporation of the solvent, 0.8 g (yield=55%) of 2-chloro-8,8-dimethyl-6,7,8,9-tetrahydro-4H-pyrimido[1,2-a]pyrimidin-4-one are obtained as a brown solid including the following characteristics:

Mass spectrum (method A) ES+/−: Rt: 2.14 min, M/Z=214.

2-hydroxy-8,8-dimethyl-6,7,8,9-tetrahydro-4H-pyrimido[1,2-a]pyrimidin-4-one may be prepared in the following way.

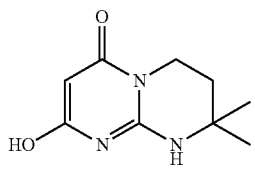

1.2 g of sodium are added in a fractionated way to 15 mL of MeOH. After total dissolution, 3 g of 4,4-dimethyl-1,4,5,6-tetrahydropyrimidin-2-amine solubilized beforehand in 5 mL of MeOH are added, and then 14.4 mL of ethyl malonate. The mixture is heated to 100° C., after 4 h of heating, the medium is dry concentrated. The obtained oil is taken up in ether. The precipitate is filtered and then the residue is taken up in 7 mL of H$_2$O and acidified with conc.HCl down to pH 3-4. The formed precipitate is filtered, washed with ether and dried in the oven in vacuo. 1.14 g (yield=90%) of 2-hydroxy-8,8-dimethyl-6,7,8,9-tetrahydro-4H-pyrimido[1,2-a]pyrimidin-4-one are obtained as a beige solid used as such.

4,4-dimethyl-1,4,5,6-tetrahydropyrimidin-2-amine hydrobromide may be prepared in the following way.

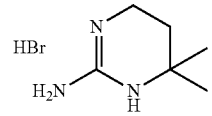

1.95 g of 3-methylbutane-1,3-diamine dihydrobromide are suspended in 20 mL of MeOH, 1.2 g of sodium methanolate are added. The mixture is stirred at RT for 2 h. The mixture is filtered and then dry evaporated. The reaction crude is solubilized in 20 mL of water, cooled with an ice bath. 0.78 g of BrCN are added and stirred at RT for 12 h. The mixture is dry evaporated, 3 g (quantitative yield) of 4,4-dimethyl-1,4,5,6-tetrahydropyrimidin-2-amine hydrobromide are obtained as a translucent oil which will be used as such for the following:

3-methylbutane-1,3-diamine dihydrobromide may be prepared in the following way.

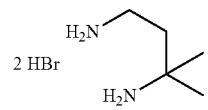

2.8 g of ethyl(3-amino-1,1-dimethylpropyl)carbamate are cooled with an ice bath. 9.9 mL of 33% HBr in acetic acid are added dropwise and then the mixture is refluxed with heating for 2 h. After returning to RT, the product is precipitated with Et$_2$O, and filtered. The obtained powder is dried in the oven at 70° C. 2.34 g (yield=55%) of 3-methylbutane-1,3-diamine dihydrobromide are obtained as a white powder used as such.

Ethyl(3-amino-1,1-dimethylpropyl)carbamate may be prepared in the following way.

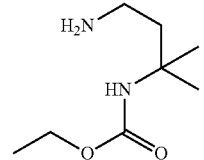

5.12 g of ethyl[3-(1,3-dioxo-1,3-dihydro-isoindol-2-yl)-1,1-dimethylpropyl]-carbamate are put into solution in 47 mL of ethanol. 4 mL of hydrazine hydrate are added and the mixture is refluxed for 30 minutes with heating. After returning to RT, the reaction medium is filtered and the solvent is then evaporated. 2.8 g (yield=88%) of ethyl(3-amino-1,1-dimethylpropyl)carbamate are obtained as a brown gum used as such.

Ethyl[3-(1,3-dioxo-1,3-dihydro-isoindol-2-yl)-1,1-dimethylpropyl]carbamate may be prepared in the following way.

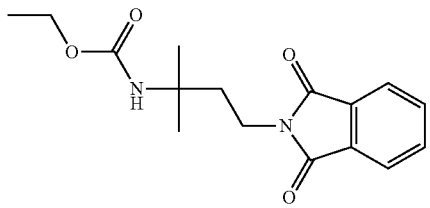 [SMILES: CCOC(=O)NC(C)(C)CCN1C(=O)c2ccccc2C1=O]

34.2 g of ethyl carbamate are put in the solution in the toluene, 22 mL of BF$_3$.Et$_2$O are added and heating is performed for 1 h 30 mins at 70° C. 11 g of 2-(3-methylbut-2-en-1-yl)-1H-isoindole-1,3-dione are added and heating with reflux is performed for 12 h. After returning to RT, the mixture is dry evaporated and then taken up in an H$_2$O/AcOEt mixture. The organic phase is decanted, washed with a solution saturated with NaCl and then dried on magnesium sulfate. The crude is purified by flash chromatography on silica gel (CH$_2$Cl$_2$/MeOH, 99/1). 5.12 g (yield=31%) of ethyl[3-(1,3-dioxo-1,3-dihydro-isoindol-2-yl)-1,1-dimethylpropyl]-carbamate are obtained as a brown powder used as such.

2-(3-methylbut-2-en-1-yl)-1H-isoindole-1,3-dione may be prepared in the following way.

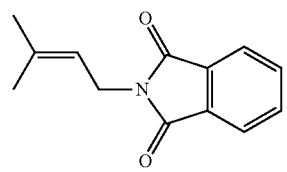 [SMILES: CC(C)=CCN1C(=O)c2ccccc2C1=O]

20 g of 1-bromo-3-methylbut-2-ene and 26.1 g of phthalimide are suspended in anhydrous DMF, and then the mixture is refluxed for 12 h with heating. After returning to RT, the reaction medium is filtered and then taken up with an aqueous solution saturated with NH$_4$Cl. The aqueous phase is extracted with AcOEt, washed with a solution of NaCl, and then dried on magnesium sulfate and dry evaporated. The obtained solid is suspended in 100 mL of water and stirred. The precipitated product is filtered, rinsed with ether and then dried in the oven in vacuo at 65° C. 18.3 g (yield=63%) of 2-(3-methylbut-2-en-1-yl)-1H-isoindole-1,3-dione are obtained as a white powder used as such.

Example 13b 9-(2-Isopropoxyethyl)-8,8-dimethyl-2-(morpholin-4-yl)-6,7,8,9-tetrahydro-4H-pyrimido[1,2-a]pyrimidin-4-one

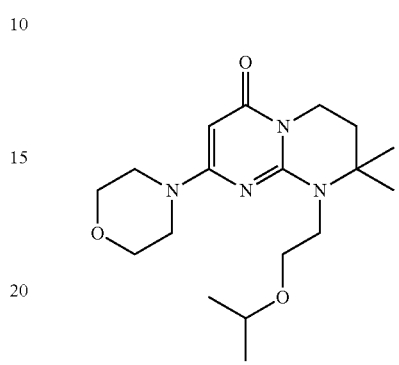

0.19 g of 2-chloro-9-(2-isopropoxyethyl)-8,8-dimethyl-6,7,8,9-tetrahydro-4H-pyrimido[1,2-a]pyrimidin-4-one in 2.5 mL of morpholine are heated in the microwave oven to 80° C. for 2 h. The crude is purified by flash chromatography on silica gel SiO$_2$ (100% CH$_2$Cl$_2$ to 92/8 CH$_2$Cl$_2$/MeOH). 0.06 g (yield=29%) of 9-(2-isopropoxyethyl)-8,8-dimethyl-2-(morpholin-4-yl)-6,7,8,9-tetrahydro-4H-pyrimido[1,2-a]pyrimidin-4-one are obtained as a white solid including the following characteristics:

Mass spectrum (method A) ES+/−: Rt: 1.43 min, M/Z=351.

$^1$H NMR spectrum (400 MHz, δ in ppm, DMSO-d6): 1.07 (d, 6H), 1.28 (s, 6H), 1.83 (t, 2H), 3.37 (t, 4H), 3.47-3.57 (m, 5H), 3.60 (t, 4H), 3.71 (t, 2H), 4.89 (s, 1H)

2-chloro-9-(2-isopropoxyethyl)-8,8-dimethyl-6,7,8,9-tetrahydro-4H-pyrimido[1,2-a]-pyrimidin-4-one may be prepared in the following way.

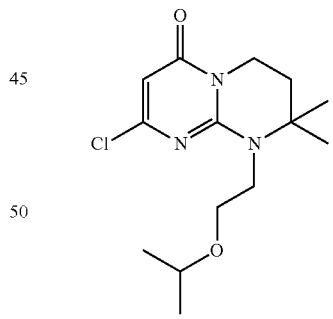

0.2 g of 2-chloro-8,8-dimethyl-6,7,8,9-tetrahydro-4H-pyrimido[1,2-a]pyrimidin-4-one are suspended in 7 mL of CH$_3$CN, 0.61 g of cesium carbonate and 0.34 g of 2-isopropoxyethyl methanesulfonate are added. The mixture is heated to 65° C. for 72 h. Water, ethyl acetate are added and then after decantation, the organic phase is dried with magnesium sulfate and then evaporated. The crude is purified by flash chromatography on silica gel SiO$_2$ (CH$_2$Cl$_2$/MeOH, 99/1). 0.19 g (yield=67%) of 2-chloro-9-(2-isopropoxyethyl)-8,8-dimethyl-6,7,8,9-tetrahydro-4H-pyrimido[1,2-a]pyrimidin-4-one are obtained as a white powder including the following characteristics:

Mass spectrum (method A) ES+/−: 2.35 min, M/Z=272.

2-isopropoxyethyl methanesulfonate may be prepared as described by Mitsuya, Morihiro et al. in Bioorganic & Medicinal Chemistry, 1999, Vol. 7, No. 11, p 2555-2568.

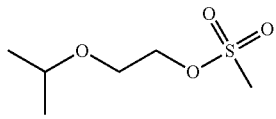

2-chloro-8,8-dimethyl-6,7,8,9-tetrahydro-4H-pyrimido[1,2-a]pyrimidin-4-one may be prepared as described in Example 12b.

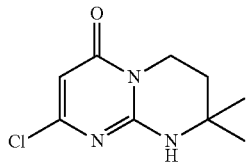

Example 14b 9-(2-Methoxyethyl)-7,7-dimethyl-2-(morpholin-4-yl)-6,7,8,9-tetrahydro-4H-pyrimido[1,2-a]pyrimidin-4-one

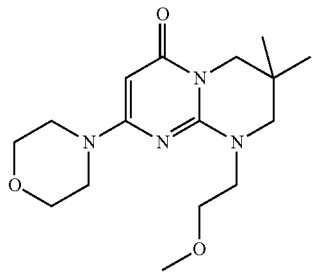 [SMILES: COCCN1CC(C)(C)Cn2c1nc(N1CCOCC1)cc2=O]

0.22 g of 7,7-dimethyl-2-(morpholin-4-yl)-6,7,8,9-tetrahydro-4H-pyrimido[1,2-a]-pyrimidin-4-one are solubilized in anhydrous DMF. 0.7 g of 60% NaH are added and stirred for 30 mins. 0.24 g of 2-methoxyethyl methanesulfonate are added and the mixture is heated with reflux for 3 h. After returning to RT, the mixture is poured into a water/ice/AcOEt mixture. The organic phase is decanted, washed with a solution saturated with NaCl and then dried with magnesium sulfate. The solvents are evaporated. The crude is purified by flash chromatography on silica gel (CH$_2$Cl$_2$/MeOH, 95/5). 0.1 g (yield=39%) of 9-(2-methoxyethyl)-7,7-dimethyl-2-(morpholin-4-yl)-6,7,8,9-tetrahydro-4H-pyrimido[1,2-a]pyrimidin-4-one are obtained as a white powder including the following characteristics:

Mass spectrum (method A) ES+/−: Rt: 2.54 min, M/Z=323.

$^1$H NMR spectrum (400 MHz, δ in ppm, DMSO-d6): 0.96 (s, 6H), 3.18 (s, 2H), 3.25 (s, 3H), 3.36 (t, 4H), 3.46 (s, 2H), 3.53 (t, 2H), 3.61 (t, 4H), 3.66 (t, 2H), 4.85 (s, 1H).

2-methoxyethyl methanesulfonate may be prepared as described by Tavecchia, P. et al. in Tetrahedron, 1995, Vol. 51, No. 16, p. 4867-4890.

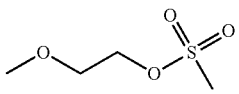

7,7-dimethyl-2-(morpholin-4-yl)-6,7,8,9-tetrahydro-4H-pyrimido[1,2-a]pyrimidin-4-one may be prepared in the following way.

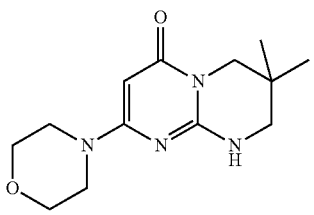 [SMILES: CC1(C)CNc2nc(N3CCOCC3)cc(=O)n2C1]

0.7 g of 2-chloro-7,7-dimethyl-6,7,8,9-tetrahydro-4H-pyrimido[1,2-a]pyrimidin-4-one in 5 mL of morpholine are heated in the microwave oven to 80° C. for 1 h30 mins. The crude is purified by flash chromatography on silica gel SiO$_2$ (100% CH$_2$Cl$_2$ to 92/8 CH$_2$Cl$_2$/MeOH). 0.58 g (yield=62%) of 7,7-dimethyl-2-(morpholin-4-yl)-6,7,8,9-tetrahydro-4H-pyrimido[1,2-a]pyrimidin-4-one are obtained as a white solid including the following characteristics:

Mass spectrum (method A) ES+/−: Rt: 1.8 min, M/Z=265.

2-chloro-7,7-dimethyl-6,7,8,9-tetrahydro-4H-pyrimido[1,2-a]pyrimidin-4-one may be prepared in the following way.

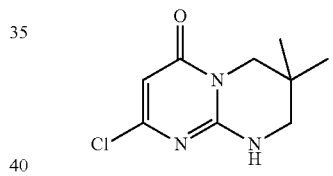

2 g of 2-hydroxy-7,7-dimethyl-6,7,8,9-tetrahydro-4H-pyrimido[1,2-a]pyrimidin-4-one are suspended in 49 mL of 1,2-dichloroethane. 15 mL of POCl$_3$ are added and then the medium is heated to 65° C. for 2 h. The medium is dry concentrated. The residue is taken up in 50 mL of EtOAc and 10 mL of H$_2$O and then cooled in an ice bath. Concentrated NaOH is added up to pH 7. The aqueous phase is extracted with EtOAc, and then the organic phase is dried on magnesium sulfate. After evaporation of the solvent, 1.4 g (yield=78%) of 2-chloro-7,7-dimethyl-6,7,8,9-tetrahydro-4H-pyrimido[1,2-a]pyrimidin-4-one are obtained as a brown solid including the following characteristics:

Mass spectrum (method A) ES+/−: Rt: 1.94 min, M/Z=214.

2-hydroxy-7,7-dimethyl-6,7,8,9-tetrahydro-4H-pyrimido[1,2-a]pyrimidin-4-one may be prepared in the following way.

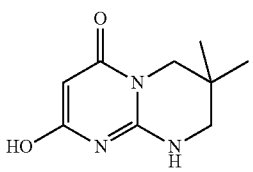

1.4 g of sodium are added in a fractionated way to 15 mL of MeOH. After total dissolution, 2.7 g of 5,5-dimethyl-1,4,5,6-tetrahydropyrimidin-2-amine solubilized beforehand in 5 mL of MeOH, and then 16.5 mL of ethyl malonate are added. The mixture is heated to 100° C., after 4 h of heating, the medium is dry concentrated. The obtained oil is taken up in ether. The precipitate is filtered and then the residue is taken up in 7 mL of H₂O and acidified with conc. HCl up to pH 3-4. The precipitate formed is filtered, washed with ether and dried in the oven in vacuo. 2 g (yield=72%) of 2-hydroxy-7,7-dimethyl-6,7,8,9-tetrahydro-4H-pyrimido[1,2-a]pyrimidin-4-one are obtained as a beige solid used as such.

5,5-dimethyl-1,4,5,6-tetrahydropyrimidin-2-amine hydrochloride may be prepared in the following way.

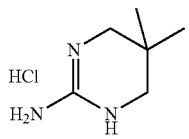

2.5 g of 2,2-dimethylpropane-1,3-diamine and 2.17 g of guanidine hydrochloride are heated to 140° C. under argon for 4 h. After returning to RT, add ethanol and dry evaporate. 3.9 g (yield=95%) of 5,5-dimethyl-1,4,5,6-tetrahydropyrimidin-2-amine hydrochloride are obtained as a white powder used as such.

Example 15b 9-(2-Isopropoxyethyl)-7,7-dimethyl-2-(morpholin-4-yl)-6,7,8,9-tetrahydro-4H-pyrimido[1,2-a]pyrimidin-4-one

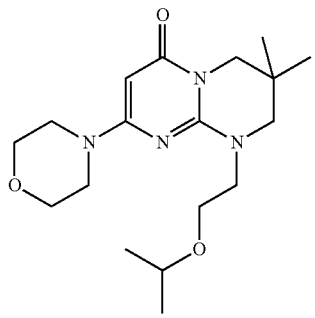 [SMILES: CC(C)OCCN1CC(C)(C)Cn2c1nc(N1CCOCC1)cc2=O]

0.17 g of 7,7-dimethyl-2-(morpholin-4-yl)-6,7,8,9-tetrahydro-4H-pyrimido[1,2-a]-pyrimidin-4-one are solubilized in anhydrous DMF. 0.03 g of 60% NaH are added and stirring is performed for 30 mins. 0.24 g of 2-isopropoxyethyl methanesulfonate are added and the mixture is heated with reflux for 3 h. After returning to RT, the mixture is poured in a water/ice/AcOEt mixture. The organic phase is decanted, washed with a solution saturated with NaCl and then dried with magnesium sulfate. The solvents are evaporated. The crude is purified by flash chromatography on silica gel (CH₂Cl₂/MeOH, 95/5). 0.08 g (yield=35%) of 9-(2-isopropoxyethyl)-7,7-dimethyl-2-(morpholin-4-yl)-6,7,8,9-tetrahydro-4H-pyrimido[1,2-a]pyrimidin-4-one are obtained as a white powder including the following characteristics:

Mass spectrum (method A) ES+/−: Rt: 1.43 min, M/Z=351.

¹H NMR spectrum (400 MHz, δ in ppm, DMSO-d6): 0.96 (s, 6H), 1.07 (d, 6H), 3.19 (s, 2H), 3.36 (br. t, 4H), 3.46 (s, 2H), 3.49-3.66 (m, 9H), 4.85 (s, 1H)

2-isopropoxyethyl methanesulfonate may be prepared as described by Mitsuya, Morihiro et al. in Bioorganic & Medicinal Chemistry, 1999, Vol. 7, No. 11, p 2555-2568.

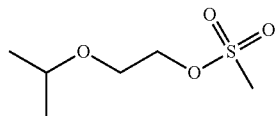

7,7-dimethyl-2-(morpholin-4-yl)-6,7,8,9-tetrahydro-4H-pyrimido[1,2-a]pyrimidin-4-one may be prepared as described in Example 14b.

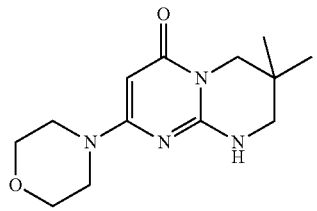 [SMILES: CC1(C)CNc2nc(N3CCOCC3)cc(=O)n2C1]

Example 16b 1-(2-Isopropoxyethyl)-8'-(morpholin-4-yl)-1',2'-dihydro-spiro[cyclopropane-1,3'-pyrimido[1,2-a]pyrimidin]-6'-one

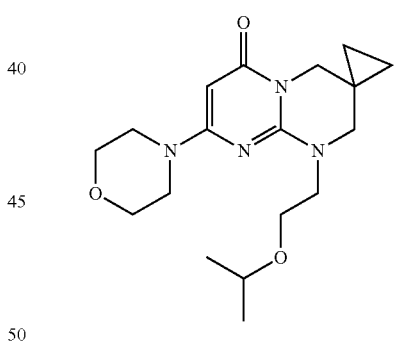

0.1 g of 8'-chloro-1'-(2-isopropoxyethyl)-1',2'-dihydro-6'H-spiro[cyclopropane-1,3'-pyrimido[1,2-a]pyrimidin]-6'-one in 0.59 mL of morpholine are heated in the microwave oven to 80° C. for 2 h. The crude is purified by flash chromatography on silica gel SiO₂ (100% CH₂Cl₂ to 92/8 CH₂Cl₂/MeOH). 0.07 g (yield=63%) of 1-(2-isopropoxyethyl)-8'-(morpholin-4-yl)-1',2'-dihydro-spiro[cyclopropane-1,3'-pyrimido[1,2-a]pyrimidin]-6'-one are obtained as a white solid including the following characteristics:

Mass spectrum (method A) ES+/−: Rt: 1.38 min, M/Z=349.

¹H NMR spectrum (400 MHz, δ in ppm, DMSO-d6): 0.61 (d, 4H), 1.06 (d, 6H), 3.30 (s, 2H), 3.36 (t, 4H), 3.48-3.65 (m, 11H), 4.85 (s, 1H)

8'-chloro-1'-(2-isopropoxyethyl)-1',2'-dihydro-6'H-spiro[cyclopropane-1,3'-pyrimido-[1,2-a]pyrimidin]-6'-one may be prepared in the following way.

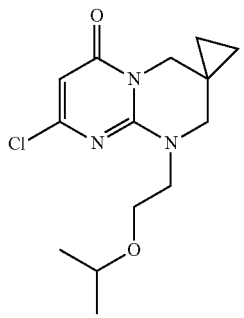 [SMILES: CC(C)OCCN1CC2(CC2)Cn2c1nc(Cl)cc2=O]

0.1 g of 8'-chloro-1',2'-dihydro-6'H-spiro[cyclopropane-1,3'-pyrimido[1,2-a]-pyrimidin]-6'-one are suspended in 10 mL of $CH_3CN$, 0.2 g of cesium carbonate and 0.17 g of 2,2-isopropoxyethyl methanesulfonate are added. The mixture is heated to 65° C. for 72 h. Water, ethyl acetate are added and then after decantation, the organic phase is dried with magnesium sulfate and then evaporated. The crude is purified by flash chromatography on silica gel $SiO_2$ ($CH_2Cl_2$/MeOH, 99/1). 0.1 g (yield=71%) of 8'-chloro-1'-(2-isopropoxyethyl)-1',2'-dihydro-6'H-spiro[cyclopropane-1,3'-pyrimido[1,2-a]pyrimidin]-6'-one are obtained as a white powder including the following characteristics:

Mass spectrum (method A) ES+/−: Rt: 2.57 min, M/Z=298.

2-isopropoxyethyl methanesulfonate may be prepared as described by Mitsuya, Morihiro et al. in Bioorganic & Medicinal Chemistry, 1999, Vol. 7, No. 11, p 2555-2568.

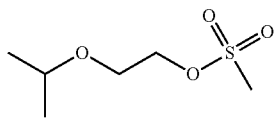

8'-chloro-1,2'-dihydro-6'H-spiro[cyclopropane-1,3'-pyrimido[1,2-a]pyrimidin]-6'-one may be prepared in the following way.

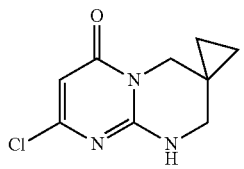

0.32 g of 8'-hydroxy-1',2'-dihydro-spiro[cyclopropane-1,3'-pyrimido[1,2-a]-pyrimidin]-6'-one are suspended in 15 mL de 1,2-dichloroethane. 0.76 mL of $POCl_3$ are added and then the medium is heated to 65° C. for 2 h. The medium is dry concentrated. The residue is taken up in 50 mL of EtOAc and 10 mL of $H_2O$ and then cooled in an ice bath. Concentrated NaOH is added up to pH 7. The aqueous phase is extracted with EtOAc, and then the organic phase is dried on magnesium sulfate. After evaporation of the solvent, 0.2 g (yield=57%) of 8'-chloro-1',2'-dihydro-6'H-spiro[cyclopropane-1,3'-pyrimido[1,2-a]pyrimidin]-6'-one are obtained as a brown solid used as such.

8'-hydroxy-1',2'-dihydro-spiro[cyclopropane-1,3'-pyrimido[1,2-a]pyrimidin]-6'-one may be prepared in the following way.

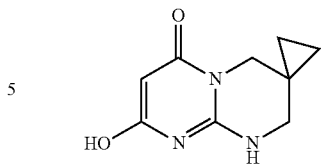

1.1 g of sodium are added in a fractionated way to 15 mL of MeOH. After total dissolution, 1.6 g of 5,7-diazaspiro[2.5]oct-5-en-6-amine hydrobromide solubilized beforehand in 5 mL of MeOH, and then 8 mL of ethyl malonate are added. The mixture is heated to 100° C., after 4 h of heating, the medium is dry concentrated. The obtained oil is taken up in ether. The precipitate is filtered and then the residue is taken up in 7 mL of $H_2O$ and acidified with concentrated HCl up to pH 3-4. The formed precipitate is filtered, washed with ether and dried in the oven in vacuo. 1.5 g (yield=60%) of 8'-hydroxy-1',2'-dihydro-spiro[cyclopropane-1,3'-pyrimido[1,2-a]pyrimidin]-6'-one are obtained as a beige solid used as such.

5,7-diazaspiro[2.5]oct-5-en-6-amine hydrobromide may be prepared in the following way.

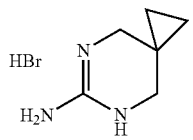

0.6 g of cyclopropane-1,1-diyldimethanamine hydrochloride are solubilized in 6 mL of water, 0.48 g of $K_2CO_3$ are added and cooling is performed to 0° C. and then 0.37 g of BrCN are added and cold stirring is maintained for 3 h. The reaction mixture containing the 5,7-diazaspiro[2.5]oct-5-en-6-amine hydrobromide is freeze-dried and then used as such for the following.

Cyclopropane-1,1-diyldimethanamine dihydrochloride may be prepared in the following way.

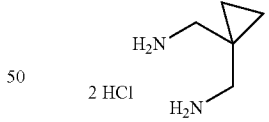

5.9 g of 1,1-bis(azidomethyl)cyclopropane is diluted in 123 mL of THF, 41.4 g of PPh3 solubilized beforehand in 62 mL of THF are added dropwise. After 30 mins of stirring at RT, 2.8 mL of water are added and the mixture is heated to 40° C. for 2 h. The reaction medium is dry evaporated and then the residue is taken up in 125 mL of $CH_2Cl_2$. The 1,1-bis(azidomethyl)cyclopropane is extracted as a salt with a 10% HCl solution. The obtained precipitate is filtered and then dried in the oven. 4.5 g (yield=67%) of cyclopropane-1,1-diyldimethanamine dihydrochloride are obtained as a white powder used as such.

1,1-bis(azidomethyl)cyclopropane may be prepared in the following way.

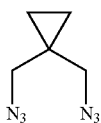

10 g of 1,1-diylbis(methylene)dimethanesulfonate are solubilized in 130 mL of DMSO, 8.2 g of NaN₃ are added and the mixture is heated to 60° C. under nitrogen for 4 h. The reaction medium is poured into a 1,300 mL of water/ice, the aqueous phase is extracted with 500 mL of CH$_2$Cl$_2$ and the gathered organic phases are then washed with water, a solution saturated with NaCl and then dried on magnesium sulfate and concentrated (not dry concentrated: risk of explosion!). The 1,1-bis(azidomethyl)-cyclopropane is used as such for the following.

Cyclopropane-1,1-diylbis(methylene)dimethanesulfonate may be prepared in the following way.

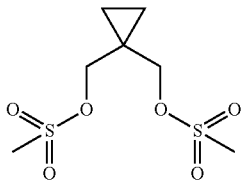

5 g of cyclopropane-1,1-diyldimethanol are solubilized in 31 mL of pyridine. Cooling is performed down to 0-5° C., and then 10.3 mL of mesyl chloride are added dropwise, stirring is performed for 2 h. Add 40.46 mL of H$_2$O+12.24 mL of concentrated HCl in order to precipitate the compound. The precipitate is filtered and dried in the oven. 10 g (yield=80%) of cyclopropane-1,1-diylbis(methylene)dimethanesulfonate are obtained as a white powder:

Example 17b (8S)-9-(2-Methanesulfonyl-ethyl)-2-morpholin-4-yl-8-trifluoromethyl-6,7,8,9-tetrahydro-pyrimido[1,2-a]pyrimidin-4-one

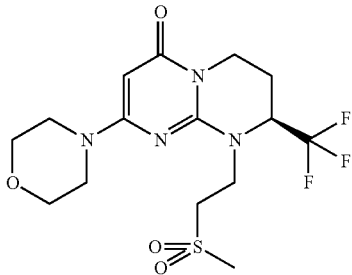 [SMILES: CS(=O)(=O)CCN1c2nc(N3CCOCC3)cc(=O)n2CC[C@H]1C(F)(F)F]

To 0.300 g (0.834 mmol) of (8S)-2-chloro-9-(2-methanesulfonyl-ethyl)-8-trifluoromethyl-6,7,8,9-tetrahydro-pyrimido[1,2-a]pyrimidin-4-one, in solution in 15 cm³ of acetonitrile, are added at a temperature close to 20° C., 0.221 g (2.085 mmol) of sodium carbonate and 0.727 g (8.34 mmol) of morpholine. After 1 h of stirring at 150° C. in a microwave appliance, the reaction medium is dry concentrated under reduced pressure (2.7 kPa) and then diluted in 30 cm³ of dichloromethane and washed three times with 15 cm³ of distilled water and then 15 cm³ of solution saturated with sodium chloride. The organic phase is dried on anhydrous magnesium sulfate, filtered and dry concentrated under reduced pressure (2.7 kPa) in order to obtain 440 mg of a colorless oil which is purified by flash chromatography on silica [eluent: dichloromethane/methanol/acetonitrile (96/2/2 by volume)]. After concentration of the fractions under reduced pressure (2.7 kPa), 298 mg of (8S)-9-(2-methanesulfonyl-ethyl)-2-morpholin-4-yl-8-trifluoromethyl-6,7,8,9-tetrahydro-pyrimido[1,2-a]pyrimidin-4-one are obtained as a white solid melting at 96° C. and including the following characteristics:

$[\alpha]_D^{25}$ at 589 nm=+22.7 (c=1.914 mg/0.5 mL DMSO)
Mass spectrum (method A) ES+/−: [M+H]$^+$: m/z 411. Rt (min)=0.55.

$^1$H NMR spectrum (400 MHz, δ in ppm, DMSO-d6): 2.13 (m, 1H); 2.34 (m, 1H); 3.04 (s, 3H); 3.17 (m, 1H); 3.36-3.46 (m, 5H); 3.58-3.72 (m, 6H); 4.18 (m, 1H); 4.37 (m, 1H); 4.66 (m, 1H); 5.01 (s, 1H).

(8S)-2-Chloro-9-(2-methanesulfonyl-ethyl)-8-trifluoromethyl-6,7,8,9-tetrahydro-pyrimido[1,2-a]pyrimidin-4-one may be prepared in the following way.

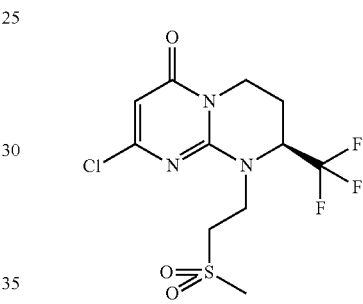

To 0.300 g (1.183 mmol) of (8S)-2-chloro-8-trifluoromethyl-6,7,8,9-tetrahydro-pyrimido[1,2-a]pyrimidin-4-one, in solution in 15 cm³ of acetonitrile, are added at a temperature close to 20° C., 0.251 g (1.183 mmol) of potassium phosphate and 0.150 g (1.42 mmol) of methyl vinyl sulfone. After 45 minutes of stirring at 90° C. in a microwave appliance, the reaction medium is dry concentrated under reduced pressure (2.7 kPa) and then diluted in 30 cm³ of dichloromethane and washed three times with 15 cm³ of distilled water and then with 15 cm³ of solution saturated with sodium chloride. The organic phase is dried on anhydrous magnesium sulfate, filtered and dry concentrated under reduced pressure (2.7 kPa) in order to obtain 390 mg of a colorless oil which is purified by flash chromatography on silica [eluent: ethyl acetate/cyclohexane (50/50 by volume)]. After concentration of the fractions under reduced pressure (2.7 kPa), 300 mg of (8S)-2-chloro-9-(2-methanesulfonyl-ethyl)-8-trifluoromethyl-6,7,8,9-tetrahydro-pyrimido[1,2-a]pyrimidin-4-one are obtained as a white solid including the following characteristics:

Mass spectrum ES+/−: [M+H]$^+$: m/z 360. Rt (min)=0.65, method A.

$^1$H NMR spectrum (400 MHz, δ in ppm, DMSO-d6): 2.19 (m, 1H); 2.41 (m, 1H); 3.09 (s, 3H); 3.28 (m partly hidden, 1H); 3.44 (m, 1H); 3.59-3.75 (m, 2H); 4.22 (m, 1H); 4.37 (m, 1H); 4.78 (m, 1H); 5.98 (s, 1H).

(8S)-2-chloro-8-trifluoromethyl-6,7,8,9-tetrahydro-pyrimido[1,2-a]pyrimidin-4-one may be prepared as described in Example 1b.

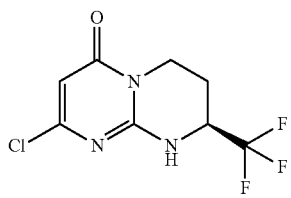 [SMILES: O=c1cc(Cl)nc2n1CC[C@@H](C(F)(F)F)N2]

Example 18b

Pharmaceutical Composition

Tablets are prepared with the following formulation:

| | |
|---|---|
| Product of Example 13b | 0.2 g |
| Excipient for a tablet completed at | 1 g |
| (detail of the excipient: lactose, talcum, starch, magnesium stearate). | |

Example 13b is taken as an example of a pharmaceutical preparation, this preparation may be made if desired with other products as examples in the present application.

Pharmacological Part:

Study of the Phosphorylation of Phosphatidylinositol (PI) with Vps34 In Vitro

This test is based on the detection of the ADP produced during phosphorylation of PI with Bps34 in the presence of ATP. ADP is detected by TR-FRET (Time resolved—Fluorescence Resonance Energy transfer) by using the Transcreener kit marketed by Cisbio (HTRF® Transcreener® ADP, reference 62ADPPEB).

The molecules are diluted with a dilution step of 3 in pure dimethylsulfoxide (DMSO Sigma Fluka 41647), and then diluted in a second step in 10% DMSO in water. 2 µL of molecules are added in 95-well plates (Corning Costar 3694) followed by 8 µL of a PI (Sigma P5766)/Vps34 (Invitrogen PV5126) mixture in a buffer A: Hepes 50 mM, $MnCl_2$ 5 mM, CHAPS 0.1%, TCEP 2 mM, pH 7.1. The reaction is started with 10 µL of an ATP solution (Sigma A7699) in a buffer A and lasts for 1 hour at room temperature. The concentrations during the reaction are 1% DMSO, 10 µM ATP, 55 µg/mL PI, about 3 nM of Vps34 and comprised between 0.51 nM and 10 µM for the molecules. The enzyme amount is adapted to each batch so as to form about 2 µM of ADP during the reaction. In parallel, an ADP and ATP range giving the possibility of calibration results is prepared according to the indications of the kit. Controls not containing any enzyme (negative control) or not containing any molecules (positive control) are also prepared in parallel. The reaction is then blocked and revealed by the Transcreener kit by using 10 µL of each of the two reagents and by following the indications of the kit. Fluorescence emission is detected on a Rubystar apparatus at 620 and 665 nm. The signal ratio is calculated by dividing the 665 nm signal by the 620 nm signal and then by multiplying by 10,000. The signal ratios are converted into an ADP concentration by using the calibration range and according to the instructions of the kit. The percentages of inhibition of the molecules are calculated relatively to the positive controls according to the formula (1−signal ratio of the molecule/signal ratio of the positive control)×100. The absolute CI50s (an inhibitory concentration giving 50% inhibition) are calculated according to a 4 parameter logistic model. With 2 independent experiments it is possible to calculate the average of the CI50s.

| Table of pharmacological results | |
|---|---|
| Example | VPS34 CI 50 (nM) |
| 1a | A |
| 2a | A |
| 3a | A |
| 4a | B |
| 5a | B |
| 6a | A |
| 7a | C |
| 8a | C |
| 9a | B |
| 1b | A |
| 2b | A |
| 3b | A |
| 4b | B |
| 5b | A |
| 6b | B |
| 7b | A |
| 8b | A |
| 9b | C |
| 10b | B |
| 11Ab | A |
| 11Bb | C |
| 12b | B |
| 13b | B |
| 14b | C |
| 15b | C |
| 16b | B |
| 17b | A |

The above results are such that:
A < 10 nM
10 nM < B < 100 nM
C > 100 nM

The invention claimed is:

1. A compound of formula (Ia):

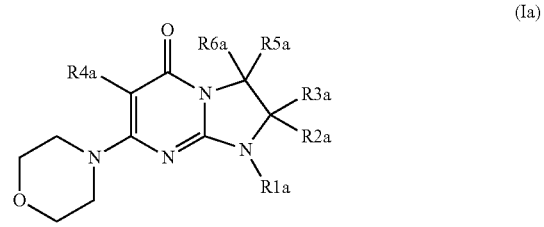

wherein:

R1a represents a linear or branched alkyl, alkenyl or alkynyl radical, a cycloalkyl radical or a heterocycloalkyl radical, containing from 1 to 7 carbon atoms, all these radicals being optionally substituted with one or several radicals, either identical or different, selected from halogen atoms and the radicals R7a, —S(O)xa-R7a with xa representing the integer 0, 1 or 2, —SO₂NR5aR7a, —CN, —OR5a, —NR5aR6a, —NR5a-COR7a, —NR5a-CO₂—R7a, —NR5a-SO₂—R7a, —NHCONR5aR6a, —COR7a, —CO₂R5a and —CONR5aR6a;

R2a represents a hydrogen atom, an alkyl radical or a cycloalkyl;

R3a represents an alkyl radical, a cycloalkyl or phenyl radical optionally substituted with one or several radicals either identical or different selected from halogen atoms and radicals —OR5a and —NR5aR6a;

R2a and R3a may optionally form with the carbon atom to which they are bound a cyclic radical containing 3 to 10 members and optionally one or several other heteroatoms selected from O, S and —NR5a, this cyclic radical being optionally substituted with one or several radicals either identical or different, selected from halogen atoms, oxo, R5a, —OR5a and —NR5aR6a radicals;

R4a represents a hydrogen atom, an alkyl radical, a halogen atom or a —CN radical;

with R5a and R6a either identical or different representing a hydrogen atom or an alkyl, cycloalkyl or heterocycloalkyl radical and R7a, either identical or different from R5a and R6a, represents an alkyl, cycloalkyl or heterocycloalkyl radical, the alkyl, cycloalkyl, heterocycloalkyl radicals above, which R5a, R6a and R7a may represent, being themselves optionally substituted with one or several radicals, either identical or different, selected from halogen atoms, —OR8a and —NR8aR9a with R8a and R9a either identical or different representing a hydrogen atom or an alkyl, cycloalkyl or heterocycloalkyl radical;

said products of formula (Ia) being in all the racemic, enantiomeric and diastereoisomeric possible isomeric forms, as well as addition salts with inorganic and organic acids or with inorganic and organic bases of said products of formula (Ia).

2. The compound of claim 1, having the following formulae:

(2S)-1-(2-Ethylbutyl)-2-methyl-7-(morpholin-4-yl)-2-(trifluoromethyl)-2,3-dihydroimidazo[1,2-a]pyrimidin-5 (1H)-one (2S)-1-Cyclopropyl-2-methyl-7-(morpholin-4-yl)-2-(trifluoromethyl)-2,3-dihydroimidazo[1,2-a]pyrimidin-5 (1H)-one (2S)-1-Cyclopentyl-2-methyl-7-(morpholin-4-yl)-2-(trifluoromethyl)-2,3-dihydroimidazo[1,2-a]pyrimidin-5 (1H)-one (S)-1-(2-Isopropoxy-ethyl)-2-methyl-7-(morpholin-4-yl)-2-(trifluoromethyl)-2,3-dihydroimidazo[1,2-a]pyrimidin-5(1H)-one (S)-1-(2-Hydroxy-2-methyl-propyl)-2-methyl-7-(morpholin-4-yl)-2-(trifluoromethyl)-2,3-dihydroimidazo[1,2-a]pyrimidin-5(1H)-one (S)-1-(2-Methoxy-2-methyl-propyl)-2-methyl-7-(morpholin-4-yl)-2-(trifluoromethyl)-2,3-dihydroimidazo[1,2-a]pyrimidin-5(1H)-one 1-(2-Isopropoxyethyl)-2,2-dimethyl-7-(morpholin-4-yl)-2,3-dihydroimidazo[1,2-a]pyrimidin-5(1H)-one 1'-(2-Methoxyethyl)-7'-morpholin-4-ylspiro[cyclopentane-1,2'-imidazo[1,2-a]pyrimidin]-5'-one 1'-(2-Isopropoxyethyl)-7'-morpholin-4-ylspiro[cyclopentane-1,2'-imidazo[1,2-a]pyrimidin]-5'-one as well as addition salts with inorganic and organic acids or with inorganic and organic bases of said compound.

3. The compound of formula (Ib):

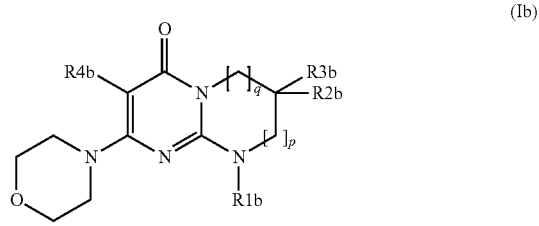

(Ib)

wherein:

p=0 or 1 and q=1 or 2 such that:

if p=0 then q=2;

if p=1 then q=1

R1b represents a linear or branched alkyl, alkenyl, or alkynyl radical, a cycloalkyl radical or a heterocycloalkyl radical, containing from 1 to 7 carbon atoms, all these radicals being optionally substituted with one or several radicals, either identical or different, selected from halogen atoms and the radicals R7b, —S(O)xb-R7b with xb representing the integer 0, 1 or 2, —SO₂NR5bR7b, —CN, —OR5b, —NR5bR6b, —NR5b-COR7b, —NR5b-CO₂—R7b, —NR5b-SO₂—R7b, —NHCONR5bR6b, —COR7b, —CO₂R5b and —CONR5bR6b;

R2b represents a hydrogen atom, an alkyl radical or a cycloalkyl radical;

R3b represents an alkyl radical, a cycloalkyl or phenyl radical optionally substituted with one or several radicals, either identical or different, selected from halogen atoms and from —OR5b and —NR5bR6b radicals;

R2b and R3b may optionally form with the carbon atom to which they are bound, a cyclic radical containing from 3 to 10 members and optionally one or several other heteroatoms selected from O, S and —NR5b, this cyclic radical being optionally substituted with one or several radicals, either identical or different, selected from halogen atoms, oxo, R5b, —OR5b and —NR5bR6b radicals;

R4b represents a hydrogen atom, an alkyl radical, a halogen atom or a —CN radical;

with R5b and R6b either identical or different, representing a hydrogen atom or an alkyl, cycloalkyl or heterocycloalkyl radical and R7b, either identical or different from R5b and R6b, representing an alkyl, cycloalkyl or heterocycloalkyl radical, the above alkyl, cycloalkyl, heterocycloalkyl radicals which are R5b and R6b and R7b may represent, being themselves optionally substituted with one or several radicals, either identical or different, selected from halogen atoms, —OR8b et —NR8bR9b with R8b and R9b either identical or different, representing a hydrogen atom or an alkyl, cycloalkyl, or heterocycloalkyl radical;

said compound of formula (Ib) being in all the racemic, enantiomeric and diastereoisomeric possible isomeric forms, as well as addition salts with inorganic and organic acids or with inorganic and organic bases of said compound of formula (Ib).

4. The compound of claim 3, having the following formulae:

(8S)-9-(2-Ethylbutyl)-2-(morpholin-4-yl)-8-(trifluoromethyl)-6,7,8,9-tetrahydro-4H-pyrimido[1,2-a]pyrimidin-4-one (8S)-9-(Cyclopropylmethyl)-2-(morpholin-4-yl)-8-(trifluoromethyl)-6,7,8,9-tetrahydro-4H-pyrimido[1,2-a]pyrimidin-4-one (8S)-9-Cyclopentyl-2-(morpholin-4-yl)-8-(trifluoromethyl)-6,7,8,9-tetrahydro-4H-pyrimido[1,2-a]pyrimidin-4-one (8S)-9-(2-Hydroxyethyl)-2-(morpholin-4-yl)-8-(trifluoromethyl)-6,7,8,9-tetrahydro-4H-pyrimido[1,2-a]pyrimidin-4-one (S)-9-(2-Isopropoxy-ethyl)-2-(morpholin-4-yl)-8-trifluoromethyl-6,7,8,9-tetrahydro-4H-pyrimido[1,2-a]pyrimidin-4-one (S)-2-(Morpholin-4-yl)-9-[2-(2,2,2-trifluoro-ethoxy)-ethyl]-8-(trifluoromethyl)-6,7,8,9-tetrahydro-4H-pyrimido[1,2-a]pyrimidin-4-one
(8S)-3-Fluoro-9-(2-isopropoxy-ethyl)-2-(morpholin-4-yl)-8-(trifluoromethyl)-6,7,8,9-tetrahydro-4H-pyrimido[1,2-a]pyrimidin-4-one
(8S)-9-(2-Hydroxy-2-methylpropyl)-2-(morpholin-4-yl)-8-(trifluoromethyl)-6,7,8,9-tetrahydro-4H-pyrimido[1,2-a]pyrimidin-4-one
(S)-9-(2-Hydroxy-2-methyl-propyl)-3-methyl-2-(morpholin-4-yl)-8-trifluoromethyl-6,7,8,9-tetrahydro-4H-pyrimido[1,2-a]pyrimidin-4-one
(S)-9-(2-Methoxy-2-methyl-propyl)-2-(morpholin-4-yl)-8-trifluoromethyl-6,7,8,9-tetrahydro-4H-pyrimido[1,2-a]pyrimidin-4-one
(8S)-8-Methyl-2-(morpholin-4-yl)-9-(2-(propan-2-yloxy)ethyl)-8-(trifluoromethyl)-6,7,8,9-tetrahydro-4H-pyrimido[1,2-a]pyrimidin-4-one
(8R)-8-Methyl-2-(morpholin-4-yl)-9-(2-(propan-2-yloxy)ethyl)-8-(trifluoromethyl)-6,7,8,9-tetrahydro-4H-pyrimido[1,2-a]pyrimidin-4-one
9-(2-Methoxyethyl)-8,8-dimethyl-2-(morpholin-4-yl)-6,7,8,9-tetrahydro-4H-pyrimido[1,2-a]pyrimidin-4-one
9-(2-Isopropoxyethyl)-8,8-dimethyl-2-(morpholin-4-yl)-6,7,8,9-tetrahydro-4H-pyrimido[1,2-a]pyrimidin-4-one
9-(2-Methoxyethyl)-7,7-dimethyl-2-(morpholin-4-yl)-6,7,8,9-tetrahydro-4H-pyrimido[1,2-a]pyrimidin-4-one
9-(2-Isopropoxyethyl)-7,7-dimethyl-2-(morpholin-4-yl)-6,7,8,9-tetrahydro-4H-pyrimido[1,2-a]pyrimidin-4-one
1'-(2-Isopropoxyethyl)-8'-(morpholin-4-yl)-1',2'-dihydro-spiro[cyclopropane-1,3'-pyrimido[1,2-a]pyrimidin]-6'-one
(8S)-9-(2-Methanesulfonyl-ethyl)-2-morpholin-4-yl-8-trifluoromethyl-6,7,8,9-tetrahydro-pyrimido[1,2-a]pyrimidin-4-one as well as the addition salts with the inorganic and organic acid or with the inorganic and organic bases of said compound of formula (Ib).

5. A method for preparing the compound of claim 1 according to the scheme 1a as defined hereafter:

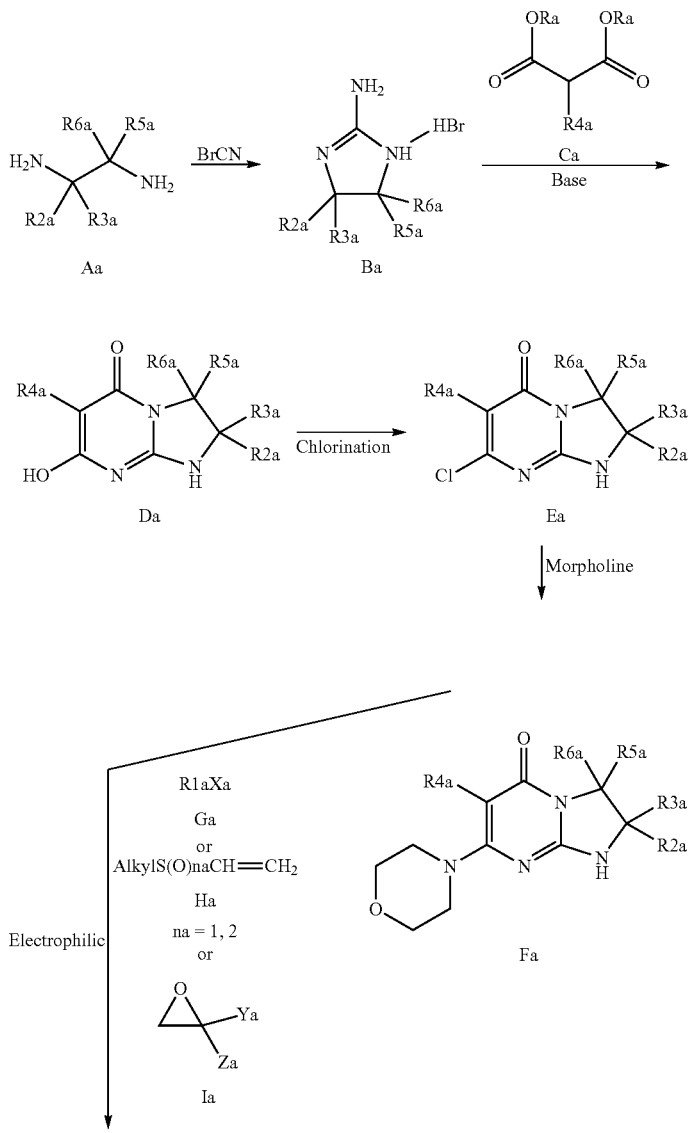

Scheme 1a:

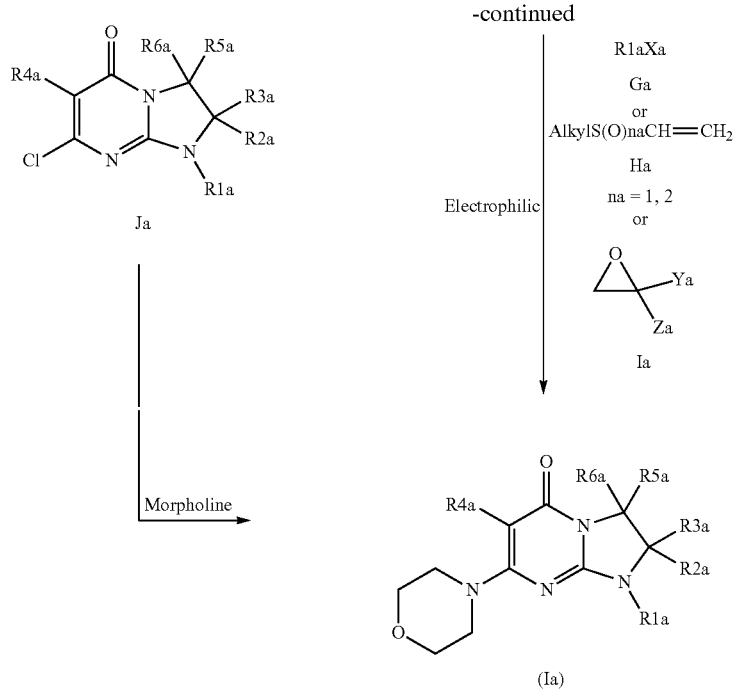
wherein the substituents R1a, R2a, R3a, R4a, R5a and R6a have the meanings indicated in claim 1; Ra represents an alkyl radical; Xa represents Cl, Br, I, OMs, OTs or OTf; and Ya and Za represent independently a hydrogen or a linear alkyl radical.
6. A method for preparing the compound of claim 3, according to scheme 1b as defined hereafter:
Scheme 1b:
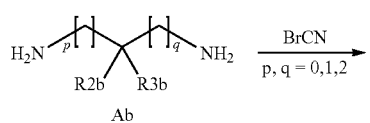
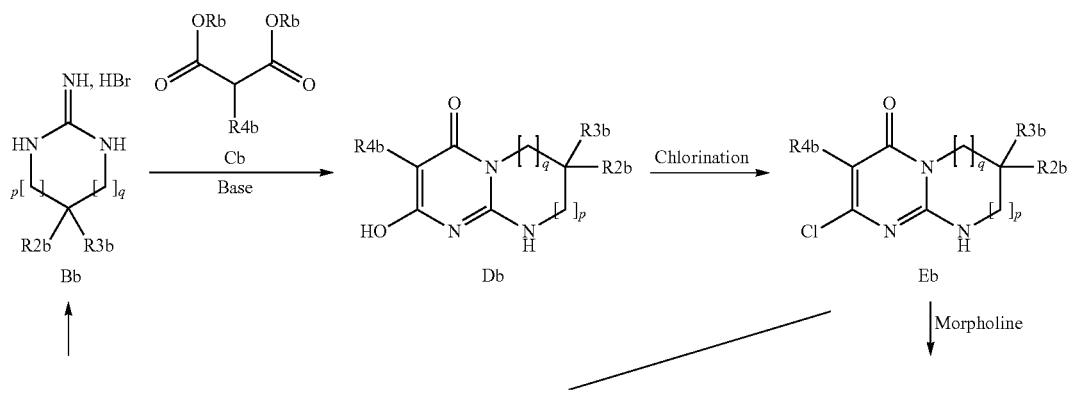

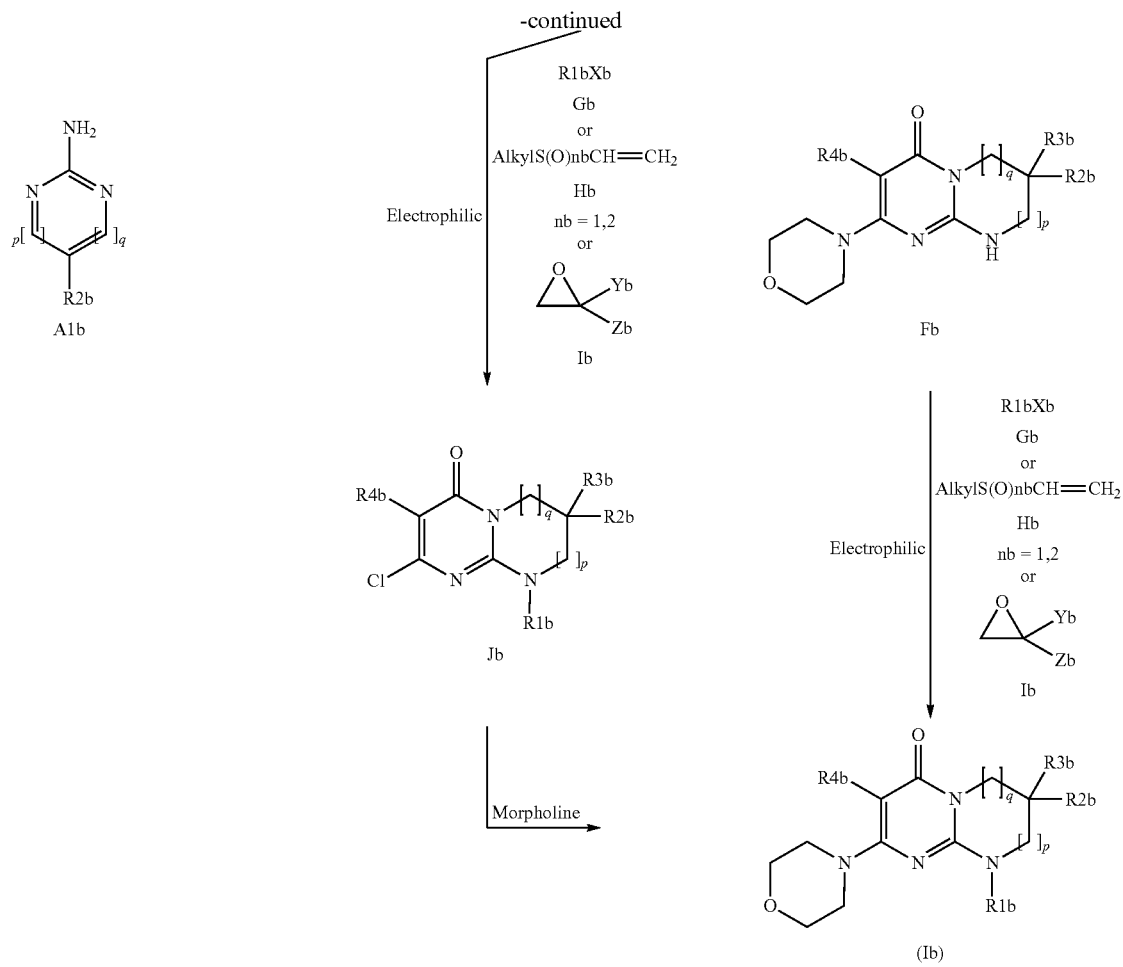

wherein the substituents p, q, R1b, R2b, R3b and R4b have the meanings indicated in claim 5; Rb represents an alkyl radical; Xb represents Cl, Br, I, OMs, OTs or OTf; and Yb and Zb represent independently a hydrogen or a linear alkyl radical.

7. A pharmaceutical composition comprising at least one of the compounds of formula (Ia) or (Ib) as defined in claim 1 or 3, and pharmaceutically acceptable salts thereof.

8. A pharmaceutical composition containing, as an active ingredient, at least one of the compounds of formula (Ia) or (Ib) as defined in claim 1 or 3, or a pharmaceutically acceptable salt of said compounds and a pharmaceutically acceptable carrier.

9. A method for treating cancers, capable of being modulated by inhibition of the Vps34/PIK3C3 route, comprising the administration to a patient of at least one of the compounds of formula (Ia) or (Ib) as defined in claim 1 or 3.

10. The method according to claim 9, for treating solid or liquid tumors.

11. The method according to claim 9, for treating cancers resistant to cytotoxic agents.

12. The method according to claim 9, wherein the cancers are chosen among primary tumors and/or metastases including gastric, liver, kidney, ovarian, colon, prostate, lung cancers (NSCLC and SCLC), glioblastomas, thyroid, bladder, breast cancers, melanoma, lymphoid or myeloid hematopoietic tumors, sarcomas, cancers of the brain, of the larynx, of the lymphatic system, cancers of bones and of the pancreas, harmartomas.

13. A cancer chemotherapy method comprising the administration, in combination with radiotherapy or anti-tumoral agents, of at least one of the compounds of formula (Ia) or (Ib) as defined in claim 1 or 3 to a patient, wherein said cancer is capable of being modulated by inhibition of the Vps34/PIK3C3 route.

14. A method for treating type II glycogenosis (or Pompe's disease) comprising the administration to a patient of at least one of the compounds of formula (Ia) or (Ib) as defined in claim 1 or 3.

\* \* \* \* \*